US012644145B2

(12) United States Patent
Chiu et al.

(10) Patent No.: US 12,644,145 B2
(45) Date of Patent: Jun. 2, 2026

(54) METHODS FOR DETECTING AND SEQUENCING A TARGET NUCLEIC ACID

(71) Applicant: The Regents of the University of California, Oakland, CA (US)

(72) Inventors: Charles Chiu, San Francisco, CA (US); Andrea Granados, San Francisco, CA (US); Jennifer A. Doudna, Berkeley, CA (US); Lucas B. Harrington, Berkeley, CA (US); Janice S. Chen, Berkeley, CA (US); Xianding Deng, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 1388 days.

(21) Appl. No.: 17/319,907

(22) Filed: May 13, 2021

(65) Prior Publication Data

US 2021/0269858 A1     Sep. 2, 2021

Related U.S. Application Data

(63) Continuation of application No. PCT/US2019/062033, filed on Nov. 18, 2019.

(60) Provisional application No. 62/769,410, filed on Nov. 19, 2018.

(51) Int. Cl.

| | |
|---|---|
| *C12Q 1/68* | (2018.01) |
| *C12Q 1/6806* | (2018.01) |
| *C12Q 1/6869* | (2018.01) |
| *C12Q 1/689* | (2018.01) |
| *C12Q 1/70* | (2006.01) |

(52) U.S. Cl.
CPC ......... *C12Q 1/6806* (2013.01); *C12Q 1/6869* (2013.01); *C12Q 1/689* (2013.01); *C12Q 1/701* (2013.01)

(58) Field of Classification Search
None
See application file for complete search history.

(56) References Cited

U.S. PATENT DOCUMENTS

| | | | | | |
|---|---|---|---|---|---|
| 9,850,484 | B2 * | 12/2017 | Joung | ............... | C12N 15/1031 |
| 10,253,365 | B1 * | 4/2019 | Doudna | ............... | C12Q 1/6876 |
| 10,738,303 | B2 * | 8/2020 | Joung | ............... | C12N 15/1031 |
| 11,118,224 | B2 * | 9/2021 | Doudna | ..................... | C12N 9/22 |
| 11,447,824 | B2 * | 9/2022 | Doudna | ............... | C12Q 1/6876 |
| 2016/0208241 | A1 * | 7/2016 | Tsai | ..................... | C12Q 1/6869 |
| 2016/0362739 | A1 * | 12/2016 | Brown | ................ | C12Q 1/6869 |
| 2017/0088833 | A1 * | 3/2017 | Joung | ............... | C12N 15/1031 |
| 2018/0237770 | A1 * | 8/2018 | May | ..................... | A61K 38/465 |
| 2019/0211404 | A1 * | 7/2019 | Ponnaluri | ............ | C12Q 1/6869 |
| 2019/0241954 | A1 * | 8/2019 | Doudna | .................. | C12N 15/11 |
| 2019/0300935 | A1 * | 10/2019 | Crawford | .................. | C12N 9/22 |
| 2020/0299768 | A1 * | 9/2020 | Doudna | ................. | C12N 15/11 |
| 2020/0399697 | A1 * | 12/2020 | Doudna | ............... | C12Q 1/6823 |
| 2021/0010065 | A1 * | 1/2021 | Salk | ..................... | C12Q 1/6818 |
| 2021/0269858 | A1 * | 9/2021 | Chiu | ..................... | C12Q 1/701 |
| 2021/0388437 | A1 * | 12/2021 | Doudna | ............... | C12Q 1/6876 |
| 2023/0068726 | A1 * | 3/2023 | Doudna | ............. | C12N 15/1065 |
| 2023/0159986 | A1 * | 5/2023 | Chiu | .................... | C12Q 1/6895 |
| | | | | | 435/6.11 |

FOREIGN PATENT DOCUMENTS

| | | | | | |
|---|---|---|---|---|---|
| WO | WO-2016186953 | A1 * | 11/2016 | .......... | C12N 15/902 |
| WO | WO-2017059313 | A1 * | 4/2017 | ........ | C12N 15/1031 |
| WO | WO-2018227025 | A1 * | 12/2018 | ............. | C12N 15/11 |
| WO | WO-2019104058 | A1 * | 5/2019 | ............. | C12N 15/11 |
| WO | WO-2021050565 | A1 * | 3/2021 | .......... | C07K 14/195 |
| WO | WO-2021216868 | A1 * | 10/2021 | .......... | C12Q 1/6806 |

OTHER PUBLICATIONS

Gao et al., 2016. Type V CRISPR-Cas Cpf1 endonuclease employs a unique mechanism for crRNA-mediated target DNA recognition. Cell research, 26(8), pp. 901-913. (Year: 2016).*
Kim et al., 2016. A simple, flexible and high-throughput cloning system for plant genome editing via CRISPR-Cas system. Journal of integrative plant biology, 58(8), pp. 705-712. (Year: 2016).*
Pattanayak et al., 2013. High-throughput profiling of off-target DNA cleavage reveals RNA-programmed Cas9 nuclease specificity. Nature biotechnology, 31(9), pp. 839-843. (Year: 2013).*
Swarts et al., Structural basis for guide RNA processing and seed-dependent DNA targeting by CRISPR-Cas12a. Mol. Cell 66, 221-233.e4 (2017). (Year: 2017).*
Tang et al., 2017. A CRISPR-Cpf1 system for efficient genome editing and transcriptional repression in plants. Nature plants, 3(3), 17018, pp. 1-21. (Year: 2017).*
Tsai et al., Smith, M.L., 2017. Amplification-free, CRISPR-Cas9 targeted enrichment and SMRT sequencing of repeat-expansion disease causative genomic regions. BioRxiv, 203919, pp. 1-26. (Year: 2017).*
Tsai et al., 2017. CIRCLE-seq: a highly sensitive in vitro screen for genome-wide CRISPR-Cas9 nuclease off-targets. Nature methods, 14(6), pp. 607-614. (Year: 2017).*
Zetsche et al., 2015. Cpf1 is a single RNA-guided endonuclease of a class 2 CRISPR-Cas system. Cell 163, 759-771. (Year: 2015).*

(Continued)

*Primary Examiner* — Gary Benzion
*Assistant Examiner* — Olayinka A Oyeyemi
(74) *Attorney, Agent, or Firm* — Gavrilovich, Dodd & Lindsey LLP

(57) ABSTRACT

The present disclosure provides methods for characterizing a target DNA present in a sample. The methods involve contacting the sample with a type V CRISPR/Cas effector protein and one or more guide RNAs, where the contacting generates a cleavage product comprising a 5' overhang; and ligating a double-stranded nucleic acid adapter to the cleavage product, to generate a ligation product. The ligation product includes the target DNA, which can be sequenced. The sample can be subjected to one or more amplification steps prior to the contacting step, with primers that provide for amplification of nucleic acids of, e.g., specific pathogens, categories of pathogens, two or more different pathogens, or two or more different categories of pathogens.

32 Claims, 39 Drawing Sheets

Specification includes a Sequence Listing.

(56)                    References Cited

OTHER PUBLICATIONS

Chen et al., Apr. 27, 2018. CRISPR-Cas 12a target binding unleashes indiscriminate single-stranded DNase activity. Science, 360(6387), pp. 436-439. (Year: 2018).*

Gootenberg et al., Apr. 27, 2018. Multiplexed and portable nucleic acid detection platform with Cas13, Cas12a, and Csm6. Science, 360(6387), pp. 439-444 or pp. 1-6. (Year: 2018).*

Kim et al., Aug. 2016. A simple, flexible and high-throughput cloning system for plant genome editing via CRISPR-Cas system. Journal of integrative plant biology, 58(8), pp. 705-712. (Year: 2016).*

Li et al. (1), Epub Mar. 12, 2018. CRISPR-Cas12a has both cis-and trans-cleavage activities on single-stranded DNA. Cell research, 28(4), pp. 491-493. (Year: 2018).*

Li et al. (2), Epub Apr. 24, 2018. CRISPR-Cas12a-assisted nucleic acid detection. Cell Discovery, 4(20): pp. 1-4. (Year: 2018).*

Chen et al., "CRISPR-Cas12a target binding unleashes indiscriminate single-stranded DNase activity," Science, 360, No. 6387, pp. 436-439, Apr. 27, 2018 (ePub Feb. 15, 2018).

Young, Lee, International Search Report (corrected), PCT/US2019062033, United States Patent & Trademark Office, Apr. 24, 2020.

Young, Lee, Written Opinion, PCT/US2019062033, United States Patent & Trademark Office, Apr. 7, 2020.

* cited by examiner

| | V2-V3 | | | | V3-V4 | | | | V4-V5 | | | |
|---|---|---|---|---|---|---|---|---|---|---|---|---|
| LbCas12a-crRNA | + | + | + | + | + | + | + | + | + | + | + | + |
| T4 DNA ligase | - | - | + | + | - | - | + | + | - | - | + | + |
| clicker (+ phosphorylation) | - | + | + | - | - | + | + | - | - | + | + | - |
| clicker (- phosphorylation) | - | - | - | + | - | - | - | + | - | - | - | + |

FIG. 5

Table 2. crRNA and clicker sequences used in the study

| | |
|---|---|
| JSC1001_preV1crRNA-Lb | UAAUUUCUACUAAGUGUAGAUAUCAUGGCUCAGAUUGAACG |
| JSC1002_V2-V3crRNA-Lb | UAAUUUCUACUAAGUGUAGAUCAACCCGAAGGCCUUCUUCA |
| JSC1003_V3-V4crRNA-Lb | UAAUUUCUACUAAGUGUAGAUCGCCCAGUAAUUCCGAUUAA |
| JSC1004_V4-V5crRNA-Lb | UAAUUUCUACUAAGUGUAGAUCGGCGUGGACUACCAGGGUA |
| JSC1006_V5-V6crRNA2-Lb | UAAUUUCUACUAAGUGUAGAUAUUCGAUGCAACGCGAAGAA |
| JSC1007_V6-V7crRNA-Lb | UAAUUUCUACUAAGUGUAGAUACAACACGAGCUGACGACAG |
| JSC1344_universal clicker | AGCTGACGTGTACTCCAGCGTCTCATCTATGCGTCAGCAGAGAATTCTGCT |
| JSC1357_preV1 dA clicker | ccagCGTTCAGCAGAATCTCTGCTGACGCATAGATGAGACGCTGGAGTACACGTCAGCTA |
| JSC1358_V2-V3 dA clicker | gtaTGAAGAAGCAGAATCTCTGCTGACGCATAGATGAGACGCTGGAGTACACGTCAGCTA |
| JSC1359_V3-V4 dA clicker | cgTTAATCGAGCAGAATCTCTGCTGACGCATAGATGAGACGCTGGAGTACACGTCAGCTA |
| JSC1360_V4-V5 dA clicker | gaTACCCTAGCAGAATCTCTGCTGACGCATAGATGAGACGCTGGAGTACACGTCAGCTA |
| JSC1361_V5-V6 dA clicker | ggTTCTTCAGCAGAATCTCTGCTGACGCATAGATGAGACGCTGGAGTACACGTCAGCTA |
| JSC1362_V6-V7 dA clicker | tggCTGTCGAGCAGAATCTCTGCTGACGCATAGATGAGACGCTGGAGTACACGTCAGCTA |

FIG. 6A

*Alicyclobacillus acidoterrestris Cas12b*

```
      1 mavksikvkl rlddmpeira glwklhkevn agvryytewl sllrqenlyr
rspngdgeqe
     61 cdktaeecka ellerlrarq venghrgpag sddellqlar qlyellvpqa
igakgdaqgi
    121 arkflsplad kdavgglgia kagnkprwvr mreagepgwe eekekaetrk
sadrtadvlr
    181 aladfglkpl mrvytdsems svewkplrkg qavrtwdrdm fqqaiermms
weswngrvgq
    241 eyaklveqkn rfeqknfvgq ehlvhlvnql qqdmkeaspg leskeqtahy
vtgralrgsd
    301 kvfekwgkla pdapfdlyda eiknvqrrnt rrfgshdlfa klaepeygal
wredasfltr
    361 yavynsilrk lnhakmfatf tlpdatahpi wtrfdklggn lhqytflfne
fgerrhairf
    421 hkllkvengv arevddtvp ismseqldnl lprdpnepla lyfrdygaeq
hftgefggak
    481 iqcrrdqlah mhrrrgardv ylnvsvrvqs qseargerrp pyaavfrlvg
dnhrafvhfd
    541 klsdylaehp ddgklgsegl lsglrvmsvd lglrtsasis vfrvarkdel
kpnskgrvpf
    601 ffpikgndnl vavhersqll klpgeteskd lraireerqr tlrqlrtqla
ylrllvrcgs
    661 edvgrrersw aklieqpvda anhmtpdwre afenelqklk slhgicsdke
wmdavyesvr
    721 rvwrhmgkqv rdwrkdvrsg erpkirgyak dvvggnsieq ieylerqykf
lkswsffgkv
    781 sgqviraekg srfaitlreh idhakedrlk kladriimea lgyvyalder
gkgkwvakyp
    841 pcqlilleel seyqfnndrp psennqlmqw shrgvfqell nqaqvhdllv
gtmyaafssr
    901 fdartgapgi rcrrvparct qehnpepfpw wlnkfvveht ldacplradd
liptgegelf
    961 vspfsaeegd fhqihadlna aqnlqqrlws dfdisqirlr cdwgevdgel
vliprltgkr
   1021 tadsysnkvf ytntgvtyye rergkkrrkv faqeklseee aellveadea
reksvvlmrd
   1081 psgiinrgnw trqkefwsmv nqriegylvk qirsvplqd sacentgdi
```

FIG. 6B

*Alicyclobacillus contaminans Cas12b*

```
       1 mgfntaellr kveeemrkts vgfdtdnpfs hritrrairg wdriseawrr
lppdapesey
      61 ieafkdiqrk nprkigsepl fknlaapgvr sellnnpqvl itfakynelg
rqlakakqfa
     121 qktlphpvfh pvwvrydklg gnlhhyqiep avhandthkv kfsslllpqe
dgsyaevkdv
     181 tvslapslqf ptglvhpkvt tpprtglvtv mdeeagkpvv cyrdrghdal
vpvafggakl
     241 qfnrahlsag yrkgvlsagg ggsiyfnvtl dvqvpnerdv sktfsfsrdr
dlvslkaeel
     301 krymetkplg mpqvrmsvd lgvrygaais vfevkpfaev rkdklhypit
gcegfvaehe
     361 rsvilklpge gvrtagkqse rkqalaaira emsilrkwlr vsqvteedra
kavrgllede
     421 rgggwtmdpg edsdhqplqg flhearlavg elvnlvhlsp aeweravier
hrrleritas
     481 hlrvfqtmrk vwgkrrneda ahtggislah iehliqqrkl firwsthart
ygevrrlpkh
     541 egfakrlqkh tnhvkedrik kladmivmas rgyrfldkra rwvktrhapc
dlilfedlsr
     601 yrftmdrppt ensqlmnwsh rellktvkmq aalfgigvgt vpaaftsrfd
aqtgapqlrc
     661 krvtkqdkek tpfwliqfae itgvnvtnve pgqlipvdgg ewfvspkgpr
aadglkcvha
     721 dinaahnlqr rfwiprlpsv kcrryveaeg faavpsstaf mkvhgkgafv
svdgefyeyq
     781 kgrrvavnra drtsstlded egdigeemlv ssngagefvr mfydesgyvg
ygrwmdskvf
     841 wgkvrqivhr aiqdqvekra aargengats sr
```

FIG. 6C

*Desulfovibrio inopinatus Cas12b*

```
      1 mptrtinlkl vlgknpenat lrralfsthr lvnqatkrie eflllcrges
yrtvdnegke
     61 aeiprhavqe ealafakaaq rhngcistye dqeildvlrq lyerlvpsvn
enneagdaga
    121 anawvsplms aesegglsvy dkvldpppvw mklkeekapg weaasqiwiq
sdeggsllnk
    181 pgspprwirk lrsgqpwqdd fvsdqkkkqd eltkgnapli kqlkemgllp
lvnpffrhll
    241 dpegkgvspw drlavraava hfisweswnh rtraeynslk lrrdefeaas
defkddftll
    301 rqyeakrhst lksialadds npyrigvrsl rawnrvreew idkgateeqr
vtilsklqtq
    361 lrgkfgdpdl fnwlaqdrhv hlwsprdsvt plvrinavdk vlrrrkpyal
mtfahprfhp
    421 rwilyeapgg snlrqyaldc tenalhitlp llvddahgtw iekkirvpla
psgqiqdltl
    481 eklekkknrl yyrsgfqqfa glaggaevlf hrpymehder seesllerpg
avwfkltldv
    541 atqappnwld gkgrvrtppe vhhfktalsn kskhtrtlqp glrvlsvdlg
mrtfascsvf
    601 ellegkpetg rafpvaders mdspnklwak hersfkltlp getpsrkeee
ersiaraely
    661 alkrdiqrlk sllrlgeedn dnrrdalleq ffkgwgeedv vpgqafprsl
fqglgaapfr
    721 stpelwrqhc qtyydkaeac lakhisdwrk rtrprptsre mwyktrsyhg
gksiwmleyl
    781 davrklllsw slrgrtygai nrqdtarfgs lasrllhhln slkedriktg
adsivgaarg
    841 yiplphgkgw eqryepcqli lfedlaryrf rvdrprrens qlmqwnhrai
vaettmqael
    901 ygqiventaa gfssrfhaat qapgvrcrfl lerdfdndlp kpyllrelsw
mlgntkvese
    961 eeklrllsek irpgslvpwd gqegfatlhp krqtlcviha dmnaaqnlqr
rffgrcqeaf
   1021 rlvcqphgdd vlrlastpga rllgalqqle ngqgafelvr dmgstsqmnr
fvmkslgkkk
   1081 ikplqdnngd deledvlsvl peeddtgrit vfrdssgiff pcnvwipakq
fwpavramiw
   1141 kvmashslg
```

FIG. 6D

*Desulfonatronum thiodismutans Cas12b*

```
    1 mvlgrkddta elrralwtth ehvnlavaev ervllrcrgr sywtldrrgd
pvhvpesqva
   61 edalamarea qrrngwpvvg edeelllair ylyeqivpsc llddlgkplk
gdagkiqtny
  121 agplfdsdtc rrdegkdvac cgpfhevagk ylgalpewat piskqefdgk
dashlrfkat
  181 ggddaffrvs iekanawyed panqdalknk aynkddwkke kdkgisswav
kyiqkqlglg
  241 qdprtevrrk lwlelgllpl fipvfdktmv gnlwnrlavr lalahllswe
swnhravgdq
  301 alarakrdel aalflgmedg faglreyelr rnesikqhaf epvdrpyvvs
gralrswtrv
  361 reewlrhgdt qesrknicnr lqdrlrgkfg dpdvfhwlae dgqealwker
dcvtsfslln
  421 dadgllekrk gyalmtfada rlhprwamye apggsnlrty qirktenglw
advvllsprn
  481 esaaveektf nvrlapsgql snvsfdqigk gskmvgrcry qsanqqfegl
lggaeilfdr
  541 krianeqhga tdlaskpghv wfkltldvrp qapqgwldgk grpalppeak
hfktalsnks
  601 kfadqvrpgl rvlsvdlgvr sfaacsvfel vrggpdqgty fpaadgrtvd
dpeklwakhe
  661 rsfkitlpge npsrkeeiar raameelrsl ngdirrikai lrlsvlqedd
prtehlrlfm
  721 eaivddpaks alnaelfkgf gddrfrstpd lwkqhchffh dkaekvvaer
fsrwrtetrp
  781 kssswqdwre rrgyaggksy wavtyleavr glilrwnmrg rtygevnrqd
kkqfgtvasa
  841 llhhinqlke driktgadmi iqaargfvpr kngagwvqvh epcrlllfed
laryrfrtdr
  901 srrensrlmr wshreivnev gmqgelyglh vdtteagfss rylassgapg
vrcrhlveed
  961 fhdglpgmhl vgeldwllpk dkdrtanear rllggmvrpg mlvpwdggel
fatlnaasgl
 1021 hvihadinaa qnlqrrfwgr cgeairivcn qlsvdgstry emakapkarl
lgalqqlkng
 1081 dapfhltsip nsqkpensyv mtptnagkky ragpgekssg eedelaldiv
eqaeelaggr
 1141 ktffrdpsgv ffapdrwlps eiywsrirrr iwqvtlerns sgrqeraemd
empy
```

FIG. 6E

*Opitutaceae bacterium TAV5* Cas12b

```
   1 mslnriyqgr vaavetqtal akgnvewmpa aggdevlwqh helfqaainy
ylvallalad
  61 knnpvlgpli sqmdnpqspy hvwgsfrrqg rqrtglsqav apyitpgnna
ptldevfrsi
 121 lagnptdrat ldaalmqllk acdgagaiqq egrsywpkfc dpdstanfag
dpamlrreqh
 181 rlllpqvlhd paithdspal gsfdtysiat pdtrtpqltg pkararlega
itlwrvrlpe
 241 saadfdrlas slkkipddds rlnlqgyvgs sakgevqarl falllfrhle
rssftlgllr
 301 satpppknae tpppagvplp aasaadpvrl argkrsfvfr aftslpcwhg
gdnihptwks
 361 fdlaafkyal tvinqieekt kerqkecael etdfdymhgr lakipvkytt
geaepppila
 421 ndlripllre llqnikvdta ltdgeavsyg lqrrtirgfr elrriwrgha
pagtvfssel
 481 keklagelrq fqtdnsttlg svqlfneliq npkywpiwqa pdvetarqwa
dagfaddpla
 541 alvqeaelqe didalkapvk ltpadpeysr rqydfnavsk fgagsrsanr
hepgqtergh
 601 ntfttelaar naadgnrwra thvrihysap rllrdglrrp dtdgnealea
vpwlqpmmea
 661 laplptlpqd ltgmpvflmp dvtlsgerri llnlpvtlep aalveqlgna
grwqnqffgs
 721 redpfalrwp adgavktakg kthipwhqdr dhftvlgvdl gtrdagalal
lnvtacpak
 781 pvhrligead grtwyaslad armirlpged arlfvrgklv qepygergrn
asllewedar
 841 niilrlgqnp dellgadprr hsypeindkl lvalrraqar larlqnrswr
lrdlaesdka
 901 ldeihaerag ekpsplppla rddaikstde allsqrdlir rsfvqianli
lplrgrrwew
 961 rphvevpdch ilaqsdpgtd dtkrlvaqgr gisherieqi eelrrrcqsl
nralrhkpge
1021 rpvlqrpakg eeiadpcpal lekinrlrdq rvdqtahail aaalgvrlra
pskdraerrh
1081 rdihgeyerf rapadfvvie nlsrylssqd rarsentrlm qwchrqivqk
lrqlcetygi
1141 pvlavpaays srfssrdgsa gfravhltpd hrhrmpwsri larlkaheed
gkrlektvld
1201 earavrglfd rldrfnaghv pgkpwrtlla plpggpvfvp lgdatpmqad
lnaalnialr
1261 giaapdrhdi hhrlraenkk rilslrlgtq rekarwpgga pavtlstpnn
gaspedsdal
1321 pervsnlfvd lagvanferv tlegvsqkfa tgrglwasvk qrawnrvarl
netvtdnnrn
1381 eeeddipm
```

FIG. 6F

Tuberibacillus calidus Cas12b

```
      1 matksfilkm ktknnpqlrl slwkthelfn fgvayymdll slfrqkdlym
hndedpdhpv
     61 vlkkeelqer lwmkvretqg kngfhgevsk devletlral yeelvpsavg
ksgeanqlsn
    121 kylypltdpa sqsgkgtans grkprwkklk eagdpswkda yekwekerqe
dpklkilaal
    181 qsfgliplfr pftendhkav isvkwmpksk nqsvrkfdkd mfnqaierfl
sweswnekva
    241 edyektvsiy eslqkelkgl stkafelmer vekayeahlr eltfsnstyr
ignrairgwt
    301 eivkkwmkld psapqgnyld vvkdyqrrhp resgdfklfe llsrpenqaa
wreypeflpl
    361 yvkyrhaegr mktakkqatf tlcdpirhpl wvryeersgt nlnkyrlimn
ekekvvqfdr
    421 liclnadghy eeqedtvpl apsqqfddqi kfssedtgkg khnfsyyhkg
inyelkqtlg
    481 gariqfdreh llrrggvkag nvgriflnvt lniepmqpfs rsgnlqtsvg
kalkvyvdgy
    541 pkvvnfkpke ltehikesek ntltlgvesl ptglrvmsvd lgqrqaaais
ifevvsekpd
    601 dnklfypvkd tdlfavhrts fniklpgekr terrmleqqk rdgairdlsr
klkflknvln
    661 mgklektder ekrvnrwikd rereeenpvy vqefemiskv lysphsvwvd
qlksihrkle
    721 eqlgkeiskw rqsisqgrqg vygislknie diektrrllf rwsmrpenpg
evkqlqpqer
    781 faidqqnhln hlkddrikkl anqivmtalg yrydgkrkkw iakhpacqlv
lfedlsryaf
    841 ydersrlenr nlmrwsrrei pkqvaqiggl ygllvgevga qyssrfhaks
gapgircrvv
    901 kehelylteg gqkvrnqkfl dslvennlie pddarrlepg dlirdqggdk
fatldergel
    961 vithadinaa qnlqkrfwtr thglyrirce srelkdavvl vpsdkdqkek
menlfgigyl
   1021 qpfkqendvy kwvkgekikg kktssqsddk elvseilqea svmadelkgn
rktlfrdpsg
   1081 yvfpkdrwyt ggryfgtleh llkrklaerr lfdggssrrg lfngtdsntn
ve
```

FIG. 6G

*Methylobacterium nodulans* Cas12b

```
      1 mltkqdkqgk ityctnmmev feaklgsadl llnwdhlrgr irdrvdagdi
gsaflklald
     61 vahvlpdgvd dqlaraafhf qsakgakskh adsvqaglrv lsidlgvrsf
atcsvfelkd
    121 tapttgvafp laefrlwavh ersftlelpg envgaagqqw raqadaelrq
lrgglnrhrq
    181 llraatvqkg erdayltdlr eawsakelwp feasllsele rcstvadplw
qdtckraarl
    241 yrtefgavvs ewrsrtrsre drkyagksmw svqhltdvrr flqswslagr
asgdirrldr
    301 erggvfakdl ldhidalkdd rlktgadliv qaargfqrne fgywvqkhap
chvilfedls
    361 ryrmrtdrpr rensqlmqwa hrgvpdmvgm qgeiygiqdr rdpdsarkha
rqplaafcld
    421 tpaafssryh astmtpgirc hplrkrefed qgflellkre negldlngyk
pgdlvplpgg
    481 evfvclnang lsrihadlna aqnlqrrfwt qhgdafrlpc gksavqgqir
waplsmgkrq
    541 agalggfgyl eptghdsgsc qwrktteaew rrlsgaqkdr deaaaaedee
lqgleeelle
    601 rsgervvffr dpsgvvlptd lwfpsaafws ivraktvgrl rshldaqaea
syavaagl
```

FIG. 6H

*Brevibacillus sp. CF112 Cas12b*

```
      1 mpkilrghkw islleqyeen rerelrenmt aandkyritk rqmkgwnely
elwstfpasa
     61 sheqykealk rvqqrlrgrf gdahffqylm eeknrliwkg npqrihyfva
rneltkrlee
    121 akqsatmtlp narkhplwvr fdarggnlqd yyltaeadkp rsrrfvtfsq
liwpsesgwm
    181 ekkdvevela lsrqfyqqvk llkndkgkqk iefkdkgsgs tfnghlggak
lqlergdlek
    241 eeknfedgei gsvylnvvid feplqevkng rvqapygqvl qlirrpnefp
kvttykseql
    301 vewlkaspqh sagveslasg frvmsidlgl raaaatsifs veessdknaa
dfsywiegtp
    361 lvavhhrsym lrlpgeqvek qvmekrderf qlhqrvkfqi rvlaqimrma
nkqygdrwde
    421 ldslkqaveq kkspldqtdr tfwegivcdl tkvlprnead weqavvqihr
kaeeyvqkav
    481 qawrkrfaad erkgiaglsm wnieeleglr klliswsrrs rnpqevnrfe
rghtshqrll
    541 thiqnvkedr lkqlshaivm talgyvyder kqewcaeypa cqvilfenls
qyrsnldrst
    601 kenstlmkwa hrsipkyvhm qaepyglqig dvraeyssrf yaktgtpgir
ckkvrgqdlq
    661 grrfenlqkr lvneqfltee qvkqlrpgdi vpddsgelfm tltdgsgske
vvflqadina
    721 ahnlqkrfwq rynelfkvsc rvivrdeeey lvpktksvqa klgkqlfvkk
sdtawkdvyv
    781 wdsqaklkgk ttfteesesp eqledfqeii eeaeeakqty rtlfrdpsgv
ffpesvwypq
    841 kdfwqevkrk lygklrerfl tkar
```

FIG. 6I

*Bacillus sp. NSP2.1 Cas12b*

```
   1 mairsiklkl kthtgpeaqn lrkgiwrthr llnegvayym kmlllfrqes
tgerpkeelq
  61 eellchireq qqrnqadknt qalpldkale alrqlyellv pssvgqsgda
qiisrkflsp
 121 lvdpnseggk gtskagakpt wqkkkeandp tweqdyekwk krreedptas
vittleeygi
 181 rplfplytnt vtdlawlplq snqfvrtwdr dmlqqaierl lsweswnkrv
qeeyaklkek
 241 maqlneqleg gqewislleq yeenrerelr enmtaandky ritkrqmkgw
nelyelwstf
 301 pasasheqyk ealkrvqqrl rgrfgdahff qylmeeknrl iwkgnpqrih
yfvarneltk
 361 rleeakqsat mtlpnarkhp lwvrfdargg nlqdyyltae adkprsrrfv
tfsqliwpse
 421 sgwmekkdve velalsrqfy qqvkllkndk gkqkiefkdk gsqstfnghl
ggaklqlerg
 481 dlekeeknfe dgelgsvyln vvidfeplqe vkngrvqapy gqvlqlirrp
nefpkvttyk
 541 seqlvewika spqhsagves lasgfrvmsi dlglraaaat sifsveessd
knaadfsywi
 601 eqtplvavhq rsymlrlpqe qvekqvmekr derfqlhqrv kfqirvlaqi
mrmankqygd
 661 rwdeldslkq aveqkkspld qtdrtfwegi vcdltkvlpr neadweqavv
qihrkaeeyv
 721 gkavqawrkr faaderkgla qlsmwnieel eglrklllsw srrtrnpqev
nrferghtsh
 781 qrllthiqnv kedrlkqlsh aivmtalgyv yderkqewca eypacqvilf
enlsqyrsnl
 841 drstkenstl mkwahrsipk yvhmqaepyg iqlgdvraey ssrfyaktgt
pgirckkvrg
 901 qdlqgrrfen lqkrlvneqf lteeqvkqlr pgdlvpddsq elfmtltdgs
gskevvflqa
 961 dinaahnlqk rfwqrynelf kvscrvivrd eeeylvpktk svqaklgkgl
fvkksdtawk
1021 dvyvwdsqak lkgkttftee sespeqledf qeileeaeea kgtyrtlfrd
psgvffpesv
1081 wypqkdfwqe vkrklygklr erfltkar
```

FIG. 6J

*Desulfatirhabdium butyrativorans Cas12b*

```
   1 mplsnnppvt qraytlrlrg adpsdlswre alwhtheavn kgakvfgdwl
ltlrgqldht
  61 ladtkvkggk gkpdrdptpe erkarrilla lswlsveskl gapssyivas
gdepakdrnd
 121 nvvsaleell qsrkvaksel ddwkrdcsas lsaairddav wvnrskvfde
avksvgsslt
 181 reeawdmler ffgsrdaylt pmkdpedkss eteqedkakd lvqkagqwls
srygtsegad
 241 fcrmsdiygk laawadnasq ggsstvddlv selrqhfdtk eskatngldw
liglssytgh
 301 tpnpvhellr qntslnkshl ddlkkkantr aescksklgs kgqrpysdai
lndvesvcgf
 361 tyrvdkdgqp vsvadyskyd vdykwgtarh yifavmldha arrislahkw
ikraeaerhk
 421 feedakrian vpararewld sfckersvts gavepyrirr ravdgwkevv
aawsksdcks
 481 tedrlaaara lqddseidkf gdiqlfeala eddalcvwhk dqeatnepdf
qplidyslai
 541 eaefkkrqfk vpayrhpdel lhpvfcdfgk srwkinydvh knvqapfyrg
lcltlwtgse
 601 ikpvplcwqs krltrdlalg nnhrndaasa vtradrlgra asnvtksdmv
nitglfeqad
 661 wngrlqaprq qleaiavvrd nprlseqern lrmcgmiehi rwlvtfsvkl
qpqgpwcaya
 721 eqhglntnpq ywphadtnrd rkvharlilp rlpglrvlsv dlghryasac
avweavntet
 781 vkeacqnvgr dmpkehdlyl hikvkkqgig kqtevdkttI yrrigadtlp
dgrphpapwa
 841 rldrqflIkl qgeekdarea sneeiwalhq meckldrtkp lidrliasgw
gllkrqmarl
 901 dalkelgwip apdssenlsr edgeakdyre slavddlmfs avrtlrlalq
rhgnrarlay
 961 ylisevklrp ggiqeklden gridllqdal alwhelfssp gwrdeaakql
wdsriatlag
1021 ykapeengdn vsdvayrkkq qvyreqlrnv aktlsqdvit ckelsdawke
rwededgrwk
1081 kllrwfkdwv lpsgtqanna tirnvgglsl srlatitefr rkvqvgfftr
lrpdgtrhel
1141 geqfggktld alellreqrv kqlasriaea algiqseggk gwdggkrprq
rindsrfapc
1201 havvienlan yrpdetrtrl enrrlmtwsa skvhkylsea cqlnglylct
vsawytsrqd
1261 srtgapgirc qdvsvrefmq spfwrkqvkq aeakhdenkg darerflcel
nktwkaktpa
1321 ewkkagfvri plrggeifvs adskspsakg ibadlnaaan iglraltdpd
wpgkwwyvpc
1381 dpvsfeskmd yvkgcaavkv gqplrqpaqt nadgaasklr kgkknrtagt
skekvylwrd
1441 isafplesne igewketsay qndvqyrvir mlkehiksld nrtgdnveg
```

FIG. 6K

Lachnospiraceae bacterium ND2006 (LbCas12a)

MSKLEKFTNCYSLSKTLRFKAIPVGKTQENIDNKRLLVEDEKRAEDYKGVKKLLDRYYLSFINDVLHSIKLKNLNNYISLFRK

KTRTEKENKELENLEINLRKEIAKAFKGNEGYKSLFKKDIIETILPEFLDDKDEIALVNSFNGFTTAFTGFFDNRENMFSEEA

KSTSIAFRCINENLTRYISNMDIFEKVDAIFDKHEVQEIKEKILNSDYDVEDFFEGEFFNFVLTQEGIDVYNAIIGGFVTESGE

KIKGLNEYINLYNQKTKQKLPKFKPLYKQVLSDRESLSFYGEGYTSDEEVLEVFRNTLNKNSEIFSSIKKLEKLFKNFDEYSSA

GIFVKNGPAISTISKDIFGEWNVIRDKWNAEYDDIHLKKKAVVTEKYEDDRRKSFKKIGSFSLEQLQEYADADLSVVEKLK

EIIIQKVDEIYKVYGSSEKLFDADFVLEKSLKKNDAVVAIMKDLLDSVKSFENYIKAFFGEGKETNRDESFYGDFVLAYDILL

KVDHIYDAIRNYVTQKPYSKDKFKLYFQNPQFMGGWDKDKETDYRATILRYGSKYYLAIMDKKYAKCLQKIDKDDVNG

NYEKINYKLLPGPNKMLPKVFFSKKWMAYYNPSEDIQKIYKNGTFKKGDMFNLNDCHKLIDFFKDSISRYPKWSNAYDF

NFSETEKYKDIAGFYREVEEQGYKVSFESASKKEVDKLVEEGKLYMFQIYNKDFSDKSHGTPNLHTMYFKLLFDENNHG

QIRLSGGAELFMRRASLKKEELVVHPANSPIANKNPDNPKKTTTLSYDVYKDKRFSEDQYELHIPIAINKCPKNIFKINTEV

RVLLKHDDNPYVIGIDRGERNLLYIVVVDGKGNIVEQYSLNEIINNFNGIRIKTDYHSLLDKKEKERFEARQNWTSIENIKEL

KAGYISQVVHKICELVEKYDAVIALEDLNSGFKNSRVKVEKQVYQKFEKMLIDKLNYMVDKKSNPCATGGALKGYQITN

KFESFKSMSTQNGFIFYIPAWLTSKIDPSTGFVNLLKTKYTSIADSKKFISSFDRIMYVPEEDLFEFALDYKNFSRTDADYIKK

WKLYSYGNRIRIFRNPKKNNVFDWEEVCLTSAYKELFNKYGINYQQGDIRALLCEQSDKAFYSSFMALMSLMLQMRNSI

TGRTDVDFLISPVKNSDGIFYDSRNYEAQENAILPKNADANGAYNIARKVLWAIGQFKKAEDEKLDKVKIAISNKEWLEY

AQTSVKH (SEQ ID NO: //)

FIG. 6L

Acidaminococcus sp. BV3L6 (AsCas12a)

MTQFEGFTNLYQVSKTLRFELIPQGKTLKHIQEQGFIEEDKARNDHYKELKPIIDRIYKTYADQCLQLVQLDWENLSAAID
SYRKEKTEETRNALIEEQATYRNAIHDYFIGRTDNLTDAINKRHAEIYKGLFKAELFNGKVLKQLGTVTTTEHENALLRSFD
KFTTYFSGFYENRKNVFSAEDISTAIPHRIVQDNFPKFKENCHIFTRLITAVPSLREHFENVKKAIGIFVSTSIEEVFSFPFYN
QLLTQTQIDLYNQLLGGISREAGTEKIKGLNEVLNLAIQKNDETAHIIASLPHRFIPLFKQILSDRNTLSFILEEFKSDEEVIQS
FCKYKTLLRNENVLETAEALFNELNSIDLTHIFISHKKLETISSALCDHWDTLRNALYERRISELTGKITKSAKEKVQRSLKHE
DINLQEIISAAGKELSEAFKQKTSEILSHAHAALDQPLPTTLKKQEEKEILKSQLDSLLGLYHLLDWFAVDESNEVDPEFSAR
LTGIKLEMEPSLSFYNKARNYATKKPYSVEKFKLNFQMPTLASGWDVNKEKNNGAILFVKNGLYYLGIMPKQKGRYKAL
SFEPTEKTSEGFDKMYYDYFPDAAKMIPKCSTQLKAVTAHFQTHTTPILLSNNFIEPLEITKEIYDLNNPEKEPKKFQTAYA
KKTGDQKGYREALCKWIDFTRDFLSKYTKTTSIDLSSLRPSSQYKDLGEYYAELNPLLYHISFQRIAEKEIMDAVETGKLYLF
QIYNKDFAKGHHGKPNLHTLYWTGLFSPENLAKTSIKLNGQAELFYRPKSRMKRMAHRLGEKMLNKKLKDQKTPIPDT
LYQELYDYVNHRLSHDLSDEARALLPNVITKEVSHEIIKDRRFTSDKFFFHVPITLNYQAANSPSKFNQRVNAYLKEHPETP
IIGIDRGERNLIYITVIDSTGKILEQRSLNTIQQFDYQKKLDNREKERVAARQAWSVVGTIKDLKQGYLSQVIHEIVDLMIH
YQAVVVLENLNFGFKSKRTGIAEKAVYQQFEKMLIDKLNCLVLKDYPAEKVGGVLNPYQLTDQFTSFAKMGTQSGFLFY
VPAPYTSKIDPLTGFVDPFVWKTIKNHESRKHFLEGFDFLHYDVKTGDFILHFKMNRNLSFQRGLPGFMPAWDIVFEKN
ETQFDAKGTPFIAGKRIVPVIENHRFTGRYRDLYPANELIALLEEKGIVFRDGSNILPKLLENDDSHAIDTMVALIRSVLQM
RNSNAATGEDYINSPVRDLNGVCFDSRFQNPEWPMDADANGAYHIALKGQLLLNHLKESKDLKLQNGISNQDWLAYI
QELRN (SEQ ID NO: //)

FIG. 6M

Francisella novicida U112 (FnCas12a)

MSIYQEFVNKYSLSKTLRFELIPQGKTLENIKARGLILDDEKRAKDYKKAKQIIDKYHQFFIEEILSSVCISEDLLQNYSDVYFK

LKKSDDDNLQKDFKSAKDTIKKQISEYIKDSEKFKNLFNQNLIDAKKGQESDLILWLKQSKDNGIELFKANSDITDIDEALEI

IKSFKGWTTYFKGFHENRKNVYSSNDIPTSIIYRIVDDNLPKFLENKAKYESLKDKAPEAINYEQIKKDLAEELTFDIDYKTSE

VNQRVFSLDEVFEIANFNNYLNQSGITKFNTIIGGKFVNGENTKRKGINEYINLYSQQINDKTLKKYKMSVLFKQILSDTES

KSFVIDKLEDDSDVVTTMQSFYEQIAAFKTVEEKSIKETLSLLFDDLKAQKLDLSKIYFKNDKSLTDLSQQVFDDYSVIGTAV

LEYITQQIAPKNLDNPSKKEQELIAKKTEKAKYLSLETIKLALEEFNKHRDIDKQCRFEEILANFAAIPMIFDEIAQNKDNLA

QISIKYQNQGKKDLLQASAEDDVKAIKDLLDQTNNLLHKLKIFHISQSEDKANILDKDEHFYLVFEECYFELANIVPLYNKIR

NYITQKPYSDEKFKLNFENSTLANGWDKNKEPDNTAILFIKDDKYYLGVMNKKNNKIFDDKAIKENKGEGYKKIVYKLLP

GANKMLPKVFFSAKSIKFYNPSEDILRIRNHSTHTKNGSPQKGYEKFEFNIEDCRKFIDFYKQSISKHPEWKDFGFRFSDT

QRYNSIDEFYREVENQGYKLTFENISESYIDSVVNQGKLYLFQIYNKDFSAYSKGRPNLHTLYWKALFDERNLQDVVYKLN

GEAELFYRKQSIPKKITHPAKEAIANKNKDNPKKESVFEYDLIKDKRFTEDKFFFHCPITINFKSSGANKFNDEINLLLKEKA

NDVHILSIDRGERHLAYYTLVDGKGNIIKQDTFNIIGNDRMKTNYHDKLAAIEKDRDSARKDWKKINNIKEMKEGYLSQV

VHEIAKLVIEYNAIVVFEDLNFGFKRGRFKVEKQVYQKLEKMLIEKLNYLVFKDNEFDKTGGVLRAYQLTAPFETFKKMGK

QTGIIYYVPAGFTSKICPVTGFVNQLYPKYESVSKSQEFFSKFDKICYNLDKGYFEFSFDYKNFGDKAAKGKWTIASFGSRLI

NFRNSDKNHNWDTREVYPTKELEKLLKDYSIEYGHGECIKAAICGESDKKFFAKLTSVLNTILQMRNSKTGTELDYLISPV

ADVNGNFFDSRQAPKNMPQDADANGAYHIGLKGLMLLGRIKNNQEGKKLNLVIKNEEYFEFVQNRNN (SEQ ID NO:

Porphyromonas macacae (PmCas12a)

MKTQHFFEDFTSLYSLSKTIRFELKPIGKTLENIKKNGLIRRDEQRLDDYEKLKKVIDEYHEDFIANILSSFSFSEEILQSYIQNL

SESEARAKIEKTMRDTLAKAFSEDERYKSIFKKELVKKDIPVWCPAYKSLCKKFDNFTTSLVPFHENRKNLYTSNEITASIPY

RIVHVNLPKFIQNIEALCELQKKMGADLYLEMMENLRNVWPSFVKTPDDLCNLKTYNHLMVQSSISEYNRFVGGYSTE

DGTKHQGINEWINIYRQRNKEMRLPGLVFLHKQILAKVDSSSFISDTLENDDQVFCVLRQFRKLFWNTVSSKEDDAASL

KDLFCGLSGYDPEAIYVSDAHLATISKNIFDRWNYISDAIRRKTEVLMPRKKESVERYAEKISKQIKKRQSYSLAELDDLLAH

YSEESLPAGFSLLSYFTSLGGQKYLVSDGEVILYEEGSNIWDEVLIAFRDLQVILDKDFTEKKLGKDEEAVSVIKKALDSALRL

RKFFDLLSGTGAEIRRDSSFYALYTDRMDKLKGLLKMYDKVRNYLTKKPYSIEKFKLHFDNPSLLSGWDKNKELNNLSVIF

RQNGYYYLGIMTPKGKNLFKTLPKLGAEEMFYEKMEYKQIAEPMLMLPKVFFPKKTKPAFAPDQSVVDIYNKKTFKTGQ

KGFNKKDLYRLIDFYKEALTVHEWKLFNFSFSPTEQYRNIGEFFDEVREQAYKVSMVNVPASYIDEAVENGKLYLFQIYNK

DFSPYSKGIPNLHTLYWKALFSEQNQSRVYKLCGGGELFYRKASLHMQDTTVHPKGISIHKKNLNKKGETSLFNYDLVKD

KRFTEDKFFFHVPISINYKNKKITNVNQMVRDYIAQNDDLQIIGIDRGERNLLYISRIDTRGNLLEQFSLNVIESDKGDLRT

DYQKILGDREQERLRRRQEWKSIESIKDLKDGYMSQVVHKICNMVVEHKAIVVLENLNLSFMKGRKKVEKSVYEKFER

MLVDKLNYLVVDKKNLSNEPGGLYAAYQLTNPLFSFEELHRYPQSGILFFVDPWNTSLTDPSTGFVNLLGRINYTNVGD

ARKFFDRFNAIRYDGKGNILFDLDLSRFDVRVETQRKLWTLTTFGSRIAKSKKSGKWMVERIENLSLCFLELFEQFNIGYR

VEKDLKKAILSQDRKEFYVRLIYLFNLMMQIRNSDGEEDYILSPALNEKNLQFDSRLIEAKDLPVDADANGAYNVARKGL

MVVQRIKRGDHESIHRIGRAQWLRYVQEGIVE (SEQ ID NO: //)

FIG. 60

Moraxella bovoculi 237 (MbCas12a)

MLFQDFTHLYPLSKTVRFELKPIDRTLEHIHAKNFLSQDETMADMHQKVKVILDDYHRDFIADMMGEVKLTKLAEFYDV

YLKFRKNPKDDELQKQLKDLQAVLRKEIVKPIGNGGKYKAGYDRLFGAKLFKDGKELGDLAKFVIAQEGESSPKLAHLAH

FEKFSTYFTGFHDNRKNMYSDEDKHTAIAYRLIHENLPRFIDNLQILTTIKQKHSALYDQIINELTASGLDVSLASHLDGYH

KLLTQEGITAYNTLLGGISGEAGSPKIQGINELINSHHNQHCHKSERIAKLRPLHKQILSDGMSVSFLPSKFADDSEMCQA

VNEFYRHYADVFAKVQSLFDGFDDHQKDGIYVEHKNLNELSKQAFGDFALLGRVLDGYYVDVVNPEFNERFAKAKTDN

AKAKLTKEKDKFIKGVHSLASLEQAIEHYTARHDDESVQAGKLGQYFKHGLAGVDNPIQKIHNNHSTIKGFLERERPAGE

RALPKIKSGKNPEMTQLRQLKELLDNALNVAHFAKLLTTKTTLDNQDGNFYGEFGVLYDELAKIPTLYNKVRDYLSQKPF

STEKYKLNFGNPTLLNGWDLNKEKDNFGVILQKDGCYYLALLDKAHKKVFDNAPNTGKSIYQKMIYKYLEVRKQFPKVF

FSKEAIAINYHPSKELVEIKDKGRQRSDDERLKLYRFILECLKIHPKYDKKFEGAIGDIQLFKKDKKGREVPISEKDLFDKINGI

FSSKPKLEMEDFFIGEFKRYNPSQDLVDQYNIYKKIDSNDNRKKENFYNNHPKFKKDLVRYYYESMCKHEEWEESFEFSK

KLQDIGCYVDVNELFTEIETRRLNYKISFCNINADYIDELVEQGQLYLFQIYNKDFSPKAHGKPNLHTLYFKALFSEDNLAD

PIYKLNGEAQIFYRKASLDMNETTIHRAGEVLENKNPDNPKKRQFVYDIIKDKRYTQDKFMLHVPITMNFGVQGMTIKE

FNKKVNQSIQQYDEVNVIGIDRGERHLLYLTVINSKGEILEQCSLNDITTASANGTQMTTPYHKILDKREIERLNARVGW

GEIETIKELKSGYLSHVVHQISQLMLKYNAIVVLEDLNFGFKRGRFKVEKQIYQNFENALIKKLNHLVLKDKADDEIGSYKN

ALQLTNNFTDLKSIGKQTGFLFYVPAWNTSKIDPETGFVDLLKPRYENIAQSQAFFGKFDKICYNADKDYFEFHIDYAKFT

DKAKNSRQIWTICSHGDKRYVYDKTANQNKGAAKGINVNDELKSLFARHHINEKQPNLVMDICQNNDKEFHKSLMYL

LKTLLALRYSNASSDEDFILSPVANDEGVFFNSALADDTQPQNADANGAYHIALKGLWLLNELKNSDDLNKVKLAIDNQ

TWLNFAQNR (SEQ ID NO: //)

FIG. 6P

Moraxella bovoculi AAX08_00205 (Mb2Cas12a)

MGIHGVPAALFQDFTHLYPLSKTVRFELKPIGRTLEHIHAKNFLSQDETMADMYQKVKVILDDYHRDFIADMMGEVKL

TKLAEFYDVYLKFRKNPKDDGLQKQLKDLQAVLRKESVKPIGSGGKYKTGYDRLFGAKLFKDGKELGDLAKFVIAQEGES

SPKLAHLAHFEKFSTYFTGFHDNRKNMYSDEDKHTAIAYRLIHENLPRFIDNLQILTTIKQKHSALYDQIINELTASGLDVSL

ASHLDGYHKLLTQEGITAYNRIIGEVNGYTNKHNQICHKSERIAKLRPLHKQILSDGMGVSFLPSKFADDSEMCQAVNEF

YRHYTDVFAKVQSLFDGFDDHQKDGIYVEHKNLNELSKQAFGDFALLGRVLDGYYVDVVNPEFNERFAKAKTDNAKAK

LTKEKDKFIKGVHSLASLEQAIEHHTARHDDESVQAGKLGQYFKHGLAGVDNPIQKIHNNHSTIKGFLERERPAGERALP

KIKSGKNPEMTQLRQLKELLDNALNVAHFAKLLTTKTTLDNQDGNFYGEFGVLYDELAKIPTLYNKVRDYLSQKPFSTEKY

KLNFGNPTLLNGWDLNKEKDNFGVILQKDGCYYLALLDKAHKKVFDNAPNTGKNVYQKMVYKLLPGPNKMLPKVFFA

KSNLDYYNPSAELLDKYAKGTHKKGDNFNLKDCHALIDFFKAGINKHPEWQHFGFKFSPTSSYRDLSDFYREVEPQGYQ

VKFVDINADYIDELVEQGKLYLFQIYNKDFSPKAHGKPNLHTLYFKALFSEDNLADPIYKLNGEAQIFYRKASLDMNETTIH

RAGEVLENKNPDNPKKRQFVYDIIKDKRYTQDKFMLHVPITMNFGVQGMTIKEFNKKVNQSIQQYDEVNVIGIDRGER

HLLYLTVINSKGEILEQRSLNDITTASANGTQVTTPYHKILDKREIERLNARVGWGEIETIKELKSGYLSHVVHQINQLMLK

YNAIVVLEDLNFGFKRGRFKVEKQIYQNFENALIKKLNHLVLKDKADDEIGSYKNALQLTNNFTDLKSIGKQTGFLFYVPA

WNTSKIDPETGFVDLLKPRYENIAQSQAFFGKFDKICYNTDKGYFEFHIDYAKFTDKAKNSRQKWAICSHGDKRYVYDKT

ANQNKGAAKGINVNDELKSLFARYHINDKQPNLVMDICQNNDKEFHKSLMCLLKTLLALRYSNASSDEDFILSPVANDE

GVFFNSALADDTQPQNADANGAYHIALKGLWLLNELKNSDDLNKVKLAIDNQTWLNFAQNR (SEQ ID NO: //)

FIG. 6Q

Moraxella bovoculi AAX11_00205 (Mb3Cas12a)

MGIHGVPAALFQDFTHLYPLSKTVRFELKPIGKTLEHIHAKNFLNQDETMADMYQKVKAILDDYHRDFIADMMGEVKL

TKLAEFYDVYLKFRKNPKDDGLQKQLKDLQAVLRKEIVKPIGNGGKYKAGYDRLFGAKLFKDGKELGDLAKFVIAQEGES

SPKLAHLAHFEKFSTYFTGFHDNRKNMYSDEDKHTAIAYRLIHENLPRFIDNLQILATIKQKHSALYDQIINELTASGLDVS

LASHLDGYHKLLTQEGITAYNTLLGGISGEAGSRKIQGINELINSHHNQHCHKSERIAKLRPLHKQILSDGMGVSFLPSKFA

DDSEVCQAVNEFYRHYADVFAKVQSLFDGFDDYQKDGIYVEYKNLNELSKQAFGDFALLGRVLDGYYVDVVNPEFNER

FAKAKTDNAKAKLTKEKDKFIKGVHSLASLEQAIEHYTARHDDESVQAGKLGQYFKHGLAGVDNPIQKIHNNHSTIKGFL

ERERPAGERALPKIKSDKSPEIRQLKELLDNALNVAHFAKLLTTKTTLHNQDGNFYGEFGALYDELAKIATLYNKVRDYLS

QKPFSTEKYKLNFGNPTLLNGWDLNKEKDNFGVILQKDGCYYLALLDKAHKKVFDNAPNTGKSVYQKMIYKLLPGPNK

MLPKVFFAKSNLDYYNPSAELLDKYAQGTHKKGDNFNLKDCHALIDFFKAGINKHPEWQHFGFKFSPTSSYQDLSDFYR

EVEPQGYQVKFVDINADYINELVEQGQLYLFQIYNKDFSPKAHGKPNLHTLYFKALFSEDNLVNPIYKLNGEAEIFYRKAS

LDMNETTIHRAGEVLENKNPDNPKKRQFVYDIIKDKRYTQDKFMLHVPITMNFGVQGMTIKEFNKKVNQSIQQYDEV

NVIGIDRGERHLLYLTVINSKGEILEQRSLNDITTASANGTQMTTPYHKILDKREIERLNARVGWGEIETIKELKSGYLSHVV

HQISQLMLKYNAIVVLEDLNFGFKRGRFKVEKQIYQNFENALIKKLNHLVLKDKADDEIGSYKNALQLTNNFTDLKSIGKQ

TGFLFYVPAWNTSKIDPETGFVDLLKPRYENIAQSQAFFGKFDKICYNADRGYFEFHIDYAKFNDKAKNSRQIWKICSHG

DKRYVYDKTANQNKGATIGVNVNDELKSLFTRYHINDKQPNLVMDICQNNDKEFHKSLMYLLKTLLALRYSNASSDEDF

ILSPVANDEGVFFNSALADDTQPQNADANGAYHIALKGLWLLNELKNSDDLNKVKLAIDNQTWLNFAQNR (SEQ ID

Thiomicrospira sp. XS5 (TsCas12a)

MGIHGVPAATKTFDSEFFNLYSLQKTVRFELKPVGETASFVEDFKNEGLKRVVSEDERRAVDYQKVKEIIDDYHRDFIEES

LNYFPEQVSKDALEQAFHLYQKLKAAKVEEREKALKEWEALQKKLREKVVKCFSDSNKARFSRIDKKELIKEDLINWLVA

QNREDDIPTVETFNNFTTYFTGFHENRKNIYSKDDHATAISFRLIHENLPKFFDNVISFNKLKEGFPELKFDKVKEDLEVDY

DLKHAFEIEYFVNFVTQAGIDQYNYLLGGKTLEDGTKKQGMNEQINLFKQQQTRDKARQIPKLIPLFKQILSERTESQSFI

PKQFESDQELFDSLQKLHNNCQDKFTVLQQAILGLAEADLKKVFIKTSDLNALSNTIFGNYSVFSDALNLYKESLKTKKAQ

EAFEKLPAHSIHDLIQYLEQFNSSLDAEKQQSTDTVLNYFIKTDELYSRFIKSTSEAFTQVQPLFELEALSSKRRPPESEDEG

AKGQEGFEQIKRIKAYLDTLMEAVHFAKPLYLVKGRKMIEGLDKDQSFYEAFEMAYQELESLIPIYNKARSYLSRKPFKAD

KFKINFDNNTLLSGWDANKETANASILFKKDGLYYLGIMPKGKTFLFDYFVSSEDSEKLKQRRQKTAEEALAQDGESYFE

KIRYKLLPGASKMLPKVFFSNKNIGFYNPSDDILRIRNTASHTKNGTPQKGHSKVEFNLNDCHKMIDFFKSSIQKHPEWG

SFGFTFSDTSDFEDMSAFYREVENQGYVISFDKIKETYIQSQVEQGNLYLFQIYNKDFSPYSKGKPNLHTLYWKALFEEAN

LNNVVAKLNGEAEIFFRRHSIKASDKVVHPANQAIDNKNPHTEKTQSTFEYDLVKDKRYTQDKFFFHVPISLNFKAQGVS

KFNDKVNGFLKGNPDVNIIGIDRGERHLLYFTVVNQKGEILVQESLNTLMSDKGHVNDYQQKLDKKEQERDAARKSWT

TVENIKELKEGYLSHVVHKLAHLIIKYNAIVCLEDLNFGFKRGRFKVEKQVYQKFEKALIDKLNYLVFKEKELGEVGHYLTAY

QLTAPFESFKKLGKQSGILFYVPADYTSKIDPTTGFVNFLDLRYQSVEKAKQLLSDFNAIRFNSVQNYFEFEIDYKKLTPKRK

VGTQSKWVICTYGDVRYQNRRNQKGHWETEEVNVTEKLKALFASDSKTTTVIDYANDDNLIDVILEQDKASFFKELLWL

LKLTMTLRHSKIKSEDDFILSPVKNEQGEFYDSRKAGEVVWPKDADANGAYHIALKGLWNLQQINQWEKGKTLNLAIKN

QDWFSFIQEKPYQE  (SEQ ID NO: //)

FIG. 6S

Butyrivibrio sp. NC3005 (BsCas12a)

MGIHGVPAAYYQNLTKKYPVSKTIRNELIPIGKTLENIRKNNILESDVKRKQDYEHVKGIMDEYHKQLINEALDNYMLPSL

NQAAEIYLKKHVDVEDREEFKKTQDLLRREVTGRLKEHENYTKIGKKDILDLLEKLPSISEEDYNALESFRNFYTYFTSYNKV

RENLYSDEEKSSTVAYRLINENLPKFLDNIKSYAFVKAAGVLADCIEEEEQDALFMVETFNMTLTQEGIDMYNYQIGKVN

SAINLYNQKNHKVEEFKKIPKMKVLYKQILSDREEVFIGEFKDDETLLSSIGAYGNVLMTYLKSEKINIFFDALRESEGKNVY

VKNDLSKTTMSNIVFGSWSAFDELLNQEYDLANENKKKDDKYFEKRQKELKKNKSYTLEQMSNLSKEDISPIENYIERISE

DIEKICIYNGEFEKIVVNEHDSSRKLSKNIKAVKVIKDYLDSIKELEHDIKLINGSGQELEKNLVVYVGQEEALEQLRPVDSLY

NLTRNYLTKKPFSTEKVKLNFNKSTLLNGWDKNKETDNLGILFFKDGKYYLGIMNTTANKAFVNPPAAKTENVFKKVDY

KLLPGSNKMLPKVFFAKSNIGYYNPSTELYSNYKKGTHKKGPSFSIDDCHNLIDFFKESIKKHEDWSKFGFEFSDTADYRDI

SEFYREVEKQGYKLTFTDIDESYINDLIEKNELYLFQIYNKDFSEYSKGKLNLHTLYFMMLFDQRNLDNVVYKLNGEAEVFY

RPASIAENELVIHKAGEGIKNKNPNRAKVKETSTFSYDIVKDKRYSKYKFTLHIPITMNFGVDEVRRFNDVINNALRTDDN

VNVIGIDRGERNLLYVVVINSEGKILEQISLNSIINKEYDIETNYHALLDEREDDRNKARKDWNTIENIKELKTGYLSQVVN

VVAKLVLKYNAIICLEDLNFGFKRGRQKVEKQVYQKFEKMLIEKLNYLVIDKSREQVSPEKMGGALNALQLTSKFKSFAEL

GKQSGIIYYVPAYLTSKIDPTTGFVNLFYIKYENIEKAKQFFDGFDFIRFNKKDDMFEFSFDYKSFTQKACGIRSKWIVYTN

GERIIKYPNPEKNNLFDEKVINVTDEIKGLFKQYRIPYENGEDIKEIIISKAEADFYKRLFRLLHQTLQMRNSTSDGTRDYIIS

PVKNDRGEFFCSEFSEGTMPKDADANGAYNIARKGLWVLEQIRQKDEGEKVNLSMTNAEWLKYAQLHLL          (SEQ ID

AacCas12b

MAVKSIKVKLRLDDMPEIRAGLWKLHKEVNAGVRYYTEWLSLLRQENLYRRSPNGDGEQECDKTAEECKAELLERLRA
RQVENGHRGPAGSDDELLQLARQLYELLVPQAIGAKGDAQQIARKFLSPLADKDAVGGLGIAKAGNKPRWVRMREAG
EPGWEEEKEKAETRKSADRTADVLRALADFGLKPLMRVYTDSEMSSVEWKPLRKGQAVRTWDRDMFQQAIERMMS
WESWNQRVGQEYAKLVEQKNRFEQKNFVGQEHLVHLVNQLQQDMKEASPGLESKEQTAHYVTGRALRGSDKVFEK
WGKLAPDAPFDLYDAEIKNVQRRNTRRFGSHDLFAKLAEPEYQALWREDASFLTRYAVYNSILRKLNHAKMFATFTLPD
ATAHPIWTRFDKLGGNLHQYTFLFNEFGERRHAIRFHKLLKVENGVAREVDDVTVPISMSEQLDNLLPRDPNEPIALYFR
DYGAEQHFTGEFGGAKIQCRRDQLAHMHRRRGARDVYLNVSVRVQSQSEARGERRPPYAAVFRLVGDNHRAFVHFD
KLSDYLAEHPDDGKLGSEGLLSGLRVMSVDLGLRTSASISVFRVARKDELKPNSKGRVPFFFPIKGNDNLVAVHERSQLLK
LPGETESKDLRAIREERQRTLRQLRTQLAYLRLLVRCGSEDVGRRERSWAKLIEQPVDAANHMTPDWREAFENELQKLK
SLHGICSDKEWMDAVYESVRRVWRHMGKQVRDWRKDVRSGERPKIRGYAKDVVGGNSIEQIEYLERQYKFLKSWSFF
GKVSGQVIRAEKGSRFAITLREHIDHAKEDRLKKLADRIIMEALGYVYALDERGKGKWVAKYPPCQLILLEELSEYQFNND
RPPSENNQLMQWSHRGVFQELINQAQVHDLLVGTMYAAFSSRFDARTGAPGIRCRRVPARCTQEHNPEPFPWWLN
KFVVEHTLDACPLRADDLIPTGEGEIFVSPFSAEEGDFHQIHADLNAAQNLQQRLWSDFDISQIRLRCDWGEVDGELVLI
PRLTGKRTADSYSNKVFYTNTGVTYYERERGKKRRKVFAQEKLSEEEAELLVEADEAREKSVVLMRDPSGIINRGNWTR
QKEFWSMVNQRIEGYLVKQIRSRVPLQDSACENTGDI (SEQ ID NO: //)

FIG. 6U crRNA repeat sequences

Figure 6U:
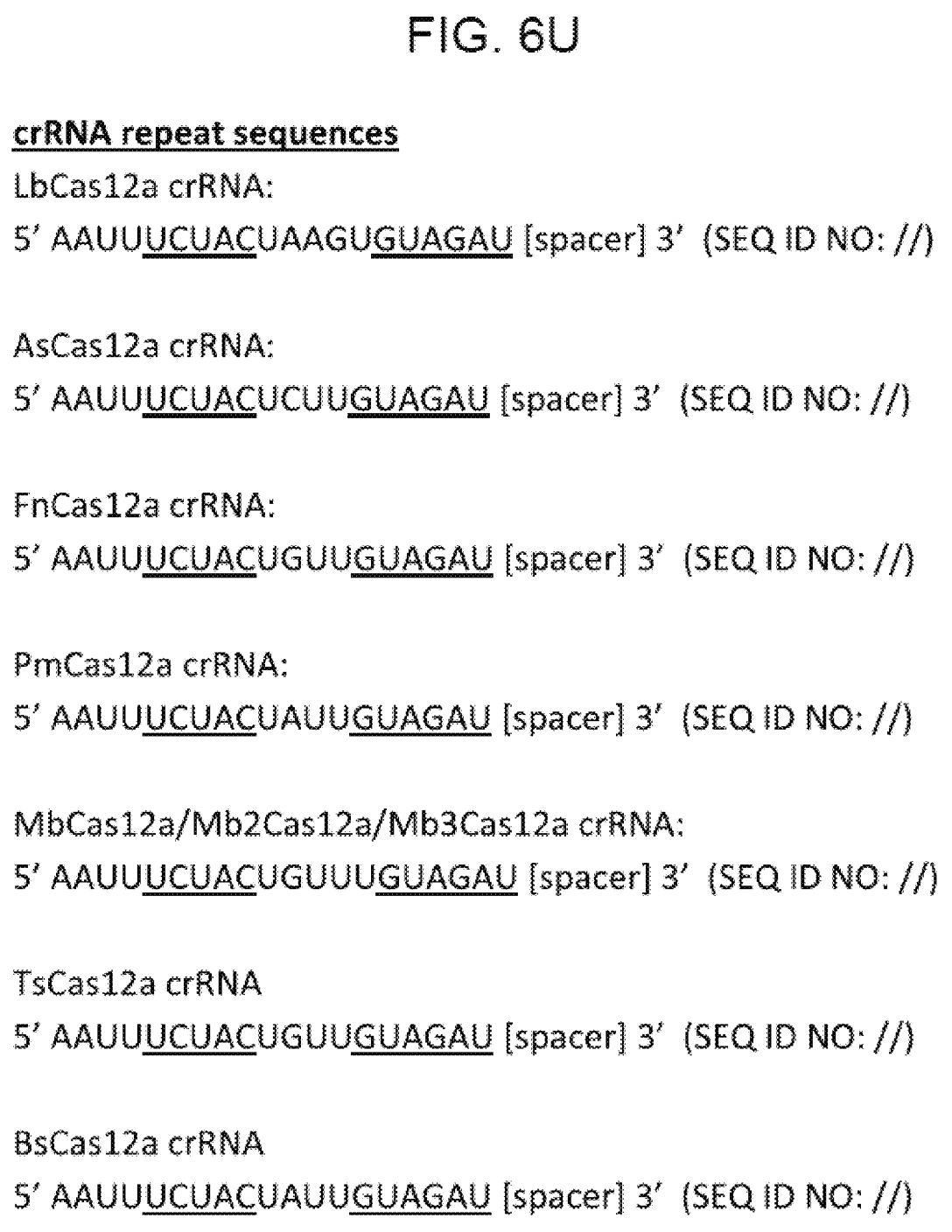

LbCas12a crRNA:

5' AAUU<u>UCUAC</u>UAAGU<u>GUAGAU</u> [spacer] 3'  (SEQ ID NO: //)

AsCas12a crRNA:

5' AAUU<u>UCUAC</u>UCUU<u>GUAGAU</u> [spacer] 3'  (SEQ ID NO: //)

FnCas12a crRNA:

5' AAUU<u>UCUAC</u>UGUU<u>GUAGAU</u> [spacer] 3'  (SEQ ID NO: //)

PmCas12a crRNA:

5' AAUU<u>UCUAC</u>UAUU<u>GUAGAU</u> [spacer] 3'  (SEQ ID NO: //)

MbCas12a/Mb2Cas12a/Mb3Cas12a crRNA:

5' AAUU<u>UCUAC</u>UGUUU<u>GUAGAU</u> [spacer] 3'  (SEQ ID NO: //)

TsCas12a crRNA

5' AAUU<u>UCUAC</u>UGUU<u>GUAGAU</u> [spacer] 3'  (SEQ ID NO: //)

BsCas12a crRNA

5' AAUU<u>UCUAC</u>UAUU<u>GUAGAU</u> [spacer] 3'  (SEQ ID NO: //)

FIG. 6V

AacCas12b single guide RNA (sgRNA)

5'
GUCUAGAGGACAGAAUUUUUCAACGGGUGUGCCAAUGGCCACUUUCCAGGUGGCAAAGCCCGU
UGAGCUUCUCAAAUCUGAGAAGUGGCAC [spacer] 3' (SEQ ID NO: //)

PAMs

LbCas12a PAM: 5'-TTTN-3'

AsCas12a PAM: 5'-TTTN-3'

FnCas12a PAM: 5'-TTTN-3'

PmCas12a PAM: 5'-TTN-3'

MbCas12a/Mb2Cas12a/Mb3Cas12a PAM: 5'-TTN-3'

TsCas12a PAM: 5'-TTN-3'

BsCas12a PAM: 5'-TTN-3'

AacCas12b PAM: 5'-TTN-3'

FIG. 7A

>CasX1
MEKRINKIRKKLSADNATKPVSRSGPMKTLLVRVMTDDLKKRLEKRRKKPEVMPQVISNNAANN
LRMLLDDYTKMKEAILQVYWQEFKDDHVGLMCKFAQPASKKIDQNLKPEMDEKGNLTTAGFAC
SQCGQPLFVYKLEQVSEKGKAYTNYFGRCNVAEHEKLILLAQLKPEKDSDEAVTYSLGKFGQRA
LDFYSIHVTKESTHPVKPLAQIAGNRYASGPVGKALSDACMGTIASFLSKYQDIIIEHQKVVKG
NQKRLESLRELAGKENLEYPSVTLPPQPHTKEGVDAYNEVIARVRMWVNLNLWQKLKLSRDDAK
PLLRLKGFPSFPVVERRENEVDWWNTINEVKKLIDAKRDMGRVFWSGVTAEKRNTILEGYNYLP
NENDHKKREGSLENPKKPAKRQFGDLLLYLEKKYAGDWGKVFDEAWERIDKKIAGLTSHIEREE
ARNAEDAQSKAVLTDWLRAKASFVLERLKEMDEKEFYACEIQLQKWYGDLRGNPFAVEAENRVV
DISGFSIGSDGHSIQYRNLLAWKYLENGKREFYLLMNYGKKGRIRFTDGTDIKKSGKWQGLLYG
GGKAKVIDLTFDPDDEQLIILPLAFGTRQGREFIWNDLLSLETGLIKLANGRVIEKTIYNKKIG
RDEPALFVALIFERREVVDPSNIKPVNLIGV<u>D</u>RGENIPAVIALTDPEGCPLPEFKDSSGGPTDI
LRIGEGYKEKQRAIQAAKEVEQRRAGGYSRK<u>F</u>ASKSRNLADDMVRNSARDLFYHAVTHDAVLVF
<u>E</u>NLSRGFGRQGKRTFMTERQYTKMEDWLTAKLAYEGLTSKTYLSKTLAQYTSKTCSNCGFTITT
ADYDGMLVRLKKTSDGWATTLNNKELKAEGQITYYNRYKRQTVEKELSAELDRLSEESGNNDIS
KWTKGRRDEALFLLKKRFSHRPVQEQFVCLDCGHEVHA<u>D</u>EQAALNIARSWLFLNSNSTEFKSYK
SGKQPFVGAWQAFYKRRLKEVWKPNA   (SEQ ID NO: //)

FIG. 7B

>CasX2

MQEIKRINKIRRRLVKDSNTKKAGKTGPMKTLLVRVMTPDLRERLENLRKKPENIPQPISNTSR
ANLNKLLTDYTEMKKAILHVYWEEFQKDPVGLMSRVAQPAPKNIDQRKLIPVKDGNERLTSSGF
ACSQCCQPLYVYKLEQVNDKGKPHTNYFGRCNVSEHERLILLSPHKPEANDELVTYSLGKFGQR
ALDFYSIHVTRESNHPVKPLEQIGGNSCASGPVGKALSDACMGAVASFLTKYQDIILEHQKVIK
KNEKRLANLKDIASANGLAFPKITLPPQPHTKEGIEAYNNVVAQIVIWVNLNLWQKLKIGRDEA
KPLQRLKGFPSFPLVERQANEVDWWDMVCNVKKLINEKKEDGKVFWQNLAGYKRQEALLPYLSS
EEDRKKGKKFARYQFGDLLLHLEKKHGEDWGKVVDEAWERIDKKVEGLSKHIKLEEERRSEDAQ
SKAALTDWLRAKASFVIEGLKEADKDEFCRCELKLQKWYGDLRGKPFAIEAENSILDISGFSKQ
YNCAFIWQKDGVKKLNLYLIINYFKGGKLRFKKIKPEAFEANRFYTVINKKSGEIVPMEVNENF
DDPNLIILPLAFGKRQGREFIWNDLLSLETGSLKLANGRVIEKTLYNRRTRQDEPALFVALTFE
RREVLDSSNIKPMNLIGIDRGENIPAVIALTDPEGCPLSRFKDSLGNPTHILRIGESYKEKQRT
IQAAKEVEQRRAGGYSRKYASKAKNLADDMVRNTARDLLYYAVTQDAMLIFENLSRGFGRQGKR
TFMAERQYTRMEDWLTAKLAYEGLPSKTYLSKTLAQYTSKTCSNCGFTITSADYDRVLEKLKKT
ATGWMTTINGKELKVECQITYYNRYKRQNVVKDLSVELDRLSEESVNNDISSWTKGRSGEALSL
LKKRFSHRPVQEKFVCLNCGFETHADEQAALNIARSWLFLRSQEYKKYQTNKTTGNTDKRAFVE
TWQSFYRKKLKEVWKPAV  (SEQ ID NO: //)

FIG. 8 unique ARDB genes

| aac2i | bl2e | ereb | mfpa | teta | vanxa |
|---|---|---|---|---|---|
| aac2ia | bl2f | erma | mpha | tetb | vanxb |
| aac2ib | bl3 | ermb | mphb | tetc | vanxd |
| aac2ic | ble | ermc | mphc | tetd | vph |
| aac2id | blt | ermd | msra | tete | |
| aac3ia | bmr | erme | norm | tetg | |
| aac3iia | cara | ermf | oleb | teth | |
| aac3iib | catal | ermg | opcm | tetj | |
| aac3iii | catal1 | ermh | opra | tetk | |
| aac3iv | catal2 | ermn | oprd | tetl | |
| aac3ix | catal3 | ermo | oprj | tetm | |
| aac3vi | catal4 | ermq | oprm | teto | |
| aac3vii | catal5 | ermr | oprn | tetpa | |
| aac3viii | catal6 | erms | otra | tetpb | |
| aac3x | cata2 | ermt | otrb | tetq | |
| aac6i | cata3 | ermu | pbpla | tets | |
| aac6ia | cata4 | ermv | pbplb | tett | |
| aac6ib | cata6 | ermw | pbp2 | tetu | |
| aac6ic | cata7 | ermx | pbp2b | tetv | |
| aac6ie | cata8 | fusb | pbp2x | tetw | |
| aac6if | cata9 | fush | pmra | tetx | |
| aac6ig | catbl | ksga | qac | tety | |
| aac6iia | catb2 | lmra | qaca | tetz | |
| aac6iib | catb3 | lmrb | qacb | tlrc | |
| aad9ib | catb5 | lnua | qnra | tmrb | |
| aadd | ceoa | lnub | qnrb | tolc | |
| acra | ceob | lsa | qnrs | tsnr | |
| acrb | cml | maca | rosa | vana | |

FIG. 8 (Cont.)

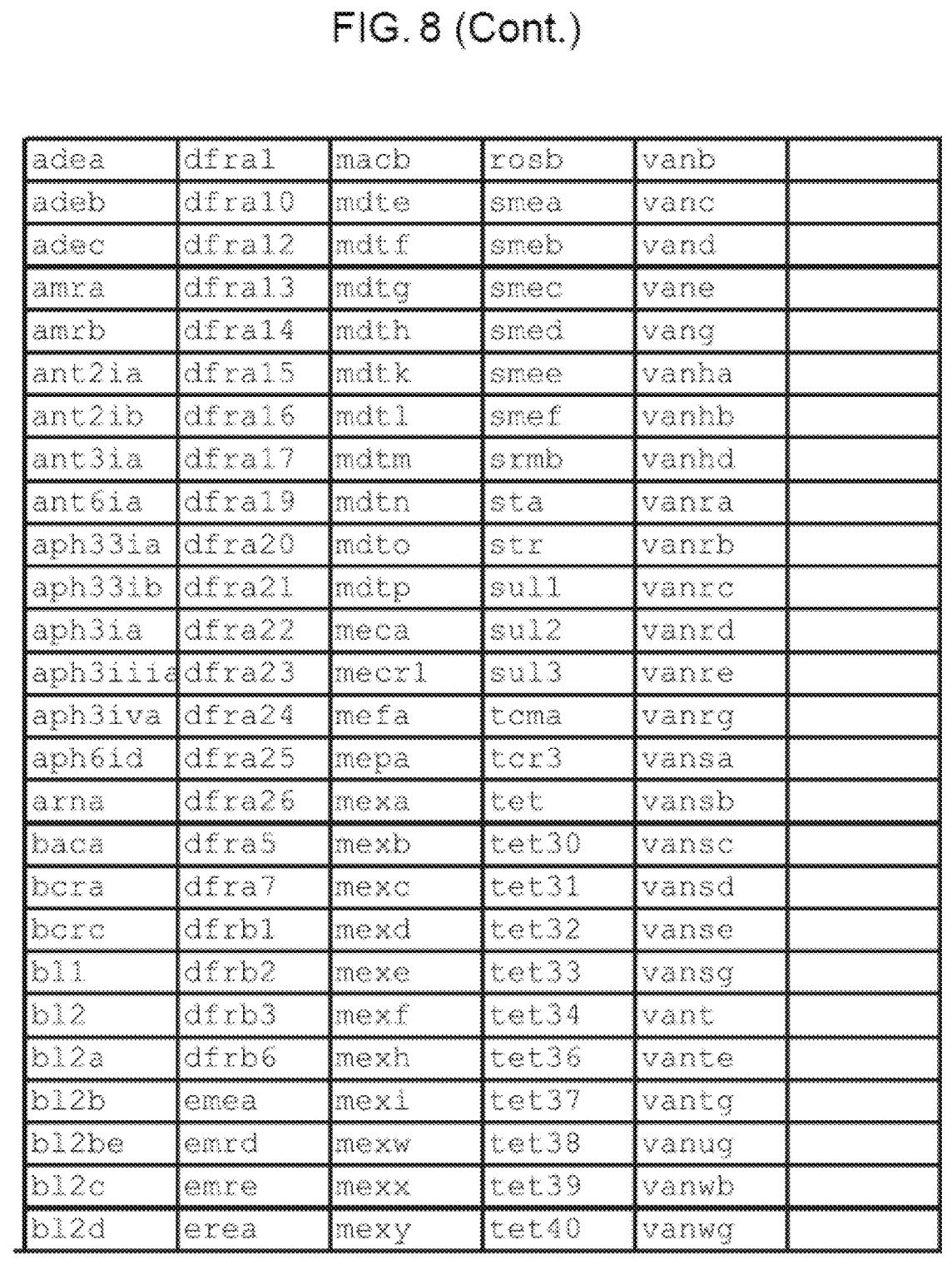

| adea | dfra1 | macb | rosb | vanb | |
|---|---|---|---|---|---|
| adeb | dfra10 | mdte | smea | vanc | |
| adec | dfra12 | mdtf | smeb | vand | |
| amra | dfra13 | mdtg | smec | vane | |
| amrb | dfra14 | mdth | smed | vang | |
| ant2ia | dfra15 | mdtk | smee | vanha | |
| ant2ib | dfra16 | mdtl | smef | vanhb | |
| ant3ia | dfra17 | mdtm | srmb | vanhd | |
| ant6ia | dfra19 | mdtn | sta | vanra | |
| aph33ia | dfra20 | mdto | str | vanrb | |
| aph33ib | dfra21 | mdtp | sul1 | vanrc | |
| aph3ia | dfra22 | meca | sul2 | vanrd | |
| aph3iiia | dfra23 | mecr1 | sul3 | vanre | |
| aph3iva | dfra24 | mefa | tcma | vanrg | |
| aph6id | dfra25 | mepa | tcr3 | vansa | |
| arna | dfra26 | mexa | tet | vansb | |
| baca | dfra5 | mexb | tet30 | vansc | |
| bcra | dfra7 | mexc | tet31 | vansd | |
| bcrc | dfrb1 | mexd | tet32 | vanse | |
| bl1 | dfrb2 | mexe | tet33 | vansg | |
| bl2 | dfrb3 | mexf | tet34 | vant | |
| bl2a | dfrb6 | mexh | tet36 | vante | |
| bl2b | emea | mexi | tet37 | vantg | |
| bl2be | emrd | mexw | tet38 | vanug | |
| bl2c | emre | mexx | tet39 | vanwb | |
| bl2d | erea | mexy | tet40 | vanwg | |

FIG. 11

| Virus | Viral titer (copies/ml)[a] | Primer type[b] | Viral RPM (ONT MinION nanopore) | # of reads | Fold change (ONT MinION nanopore)[c] | Viral RPM (Illumina MiSeq) | Fold Change (Illumina MiSeq)[d] |
|---|---|---|---|---|---|---|---|
| ZIKV | 10 | RH | 0 | 141,549 | | 0 | |
| ZIKV | 10 | ArboV-SP | 8 | 378,382 | >8.0 | 3.1 | >3.1 |
| ZIKV | 10 | RH | 0 | 131,662 | | 0.68 | |
| ZIKV | 10 | ArboV-SP | 28 | 393,179 | >28 | 11.2 | 16.4 |
| EBOV | 10 | RH | 1 | 810,439 | | 0.27 | |
| EBOV | 10 | EBOV-SP | 14 | 1,140,463 | 14 | 15 | 55 |
| EBOV | 10 | HFV-SP | 2 | 489,000 | 2.0 | 2 | 7.4 |
| EBOV | 100 | RH | 0 | 645,349 | | 8 | |
| EBOV | 100 | EBOV-SP | 108 | 608,429 | >108 | 130 | 16 |
| EBOV | 100 | HFV-SP | 31 | 386,053 | >31 | 53.6 | 6.7 |
| ZIKV | 100 | RH | 31 | 252,145 | | 16 | |
| ZIKV | 100 | ZIKV-SP | 341 | 259,154 | 11 | 247 | 15 |

FIG. 11 (Cont.)

| DENV | 100 | RH | 42 | 307,846 | | 38 | |
|---|---|---|---|---|---|---|---|
| DENV | 100 | DENV-SP | 82 | 763,017 | 1.5 | 199 | 5.2 |
| DENV | 100 | ArboV-SP | 103 | 202,737 | 2.5 | 141 | 3.7 |
| EBOV | 1,000 | RH | 216 | 244,554 | | 358 | |
| EBOV | 1,000 | EBOV-SP | 6,117 | 472,770 | 28 | 7,563 | 21 |
| ZIKV | 1,000 | RH | 208 | 125,000 | | 88 | |
| ZIKV | 1,000 | ZIKV-SP | 1,570 | 70,000 | 7.5 | 1,238 | 19 |
| ZIKV | 1,000 | ArboV-SP | 1,325 | 81,499 | 6.3 | 740.7 | 11 |
| DENV | 1,000 | RH | 322 | 433,949 | | 240 | |
| DENV | 1,000 | DENV-SP | 1,431 | 338,789 | 4.4 | 1,511 | 6.3 |
| DENV | 1,000 | ArboV-SP | 699 | 520,593 | 2.2 | 945 | 4.0 |

[a] determined by quantitative RT-PCR
[b] EBOV-SP/ZIKV-SP/ZIKV-SP/DENV-SP, target virus-specific spiked primers at 4 µM concentration and mixed with RH at 10:1 ratio; ArboV-SP, arbovirus panel spiked primers at 10 µM concentration; HFV-SP, hemorrhagic fever virus panel spiked primers at 20 µM concentration
[c] median fold change was 7.8
[d] median fold change was 9.2

Abbreviations: RPM, reads per million; ONT, Oxford Nanopore Technologies; RH, random hexamer; SP, spiked primers

FIG. 12

| Sample Type | Virus | Strain / subtype | Viral titer (copies/ml) | Primer type[a] | Fold enrichment | # of viral reads (RH primers)[b] | Genome coverage (RH primers)[b] | # of viral reads (spiked primers)[b] | Genome coverage (spiked primers) | % increase in coverage[c] |
|---|---|---|---|---|---|---|---|---|---|---|
| Viral Culture | ZIKV | Uganda MR766 | 100 | ZIKV-SP | 10.0 | 31 | 23.70% | 309 | 67.2% | 43.5% |
| | ZIKV | Uganda MR766 | 100 | ZIKV-SP | 15.4 | 13 | 4.30% | 200 | 44.3% | 40.0% |
| | ZIKV | Uganda MR766 | 1,000 | ZIKV-SP | 19.2 | 64 | 46.20% | 1229 | 95.6% | 49.4% |
| | HIV-1 | Group M, CRF01 | 100 | HIV-SP | 10.5 | 17 | 12.30% | 179 | 66.4% | 54.1% |
| | DENV | type 1 | 100 | DENV-SP | 5.2 | 69 | 29% | 359 | 80.9% | 51.9% |
| | DENV | type 1 | 1,000 | DENV-SP | 8.3 | 382 | 67.50% | 2411 | 97.2% | 30.0% |
| | EBOV | Ebola Kikwit-95 | 100 | EBOV-SP | 10.5 | 200 | 7.50% | 2095 | 84.9% | 77.4% |
| | EBOV | Ebola Kikwit-95 | 1,000 | EBOV-SP | 21.0 | 385 | 45.20% | 8095 | 90.3% | 45.1% |
| | Mean (SD) | | | | | | | | | 49 (±13.8)% |

FIG. 12 (Cont.)

| Clinical Serum Sample | | | | | | | | | |
|---|---|---|---|---|---|---|---|---|---|
| HIV | CRF01, #8 | 1,000 | HIV-SP | 6.0 | 55 | 21% | 330 | 92% | 71.0% |
| HIV | CRF01, #9 | 1,000 | HIV-SP | 3.1 | 76 | 44.80% | 234 | 83% | 38.2% |
| HIV | CRF01, #18 | 10,000 | HIV-SP | 2.6 | 138 | 67% | 358 | 88% | 21.0% |
| HIV | URF-0201, #22 | 1,000 | HIV-SP | 2.3 | 74 | 47.80% | 167 | 74.6% | 26.8% |
| HIV | URF-0122, #20 | 1,000 | HIV-SP | 8.8 | 11 | 13.50% | 97 | 81.4% | 47.9% |
| HCV | Genotype 2 | 1,000 | HCV-SP | 5.0 | 14 | 11.40% | 70 | 54% | 42.6% |
| HCV | Genotype 4 | 10,000 | HCV-SP | 1.7 | 411 | 33.30% | 707 | 82.6% | 49.5% |
| HCV | Genotype 6 | 1,000 | HCV-SP | 3.0 | 30 | 16.40% | 91 | 55% | 38.6% |
| Mean (SD) | | | | | | | | | 42% (±15.3%) |
| Overall mean % increase in coverage | | | | | | | | | 45.4% (±14.5%) | a EBOV-SP/ZIKV-SP/DENV-SP/HIV-SP/HCV-SP, target virus-specific spiked primers at 4 µM concentration and mixed with RH at 10:1 ratio b number of reads normalized by fold enrichment for purposes of comparison c using spiked primers relative to random hexamer primers only Abbreviations: RH, random hexamer; SP, spiked primers; CRF, HIV circulating recombinant form; URF, HIV unique recombinant form

FIG. 13

| Virus | Clinical sample type | Primer type[a] | # of preprocessed reads[b] | # of viral reads (RH primers) | Viral RPM (RH primers) | Genome coverage (RH primers) | # of viral reads (spiked primers) | Viral RPM (spiked primers) | Genome coverage (spiked primers) | % increase in coverage[c] | Fold change |
|---|---|---|---|---|---|---|---|---|---|---|---|
| Usutu | serum | ArboV-SP | 122,517,964 | 114 | 0.9 | 5.5% | 845 | 6.8 | 23.0% | 17.5 | 7.5 |
| SLEV | CSF | ZIKV-SP | 500,000 | 96 | 192 | 67.2% | 288 | 576 | 92.8% | 25.6 | 3 |
| Powassan | CSF | ArboV-SP | 11,268,014 | 88 | 7.8 | 39.6% | 1,007 | 114.6 | 82.6% | 43 | 14.7 | a ZIKV-SP, target virus-specific spiked primers at 4 μM concentration and mixed with RH at 10:1 ratio; ArboV-SP, arbovirus panel spiked primers at 10 μM concentration b same # of preprocessed reads analyzed from the RH and spiked primer runs for purposes of comparison c using spiked primers relative to random hexamer primers only Abbreviations: RH, random hexamer; RPM, reads per million; SLEV, St. Louis encephalitis virus; CSF, cerebrospinal fluid

METHODS FOR DETECTING AND SEQUENCING A TARGET NUCLEIC ACID

CROSS-REFERENCE

This application is a continuation of International Application No. PCT/US2019/062033, filed Nov. 18, 2019, which application claims the benefit of U.S. Provisional Patent Application No. 62/769,410, filed Nov. 19, 2018, which applications are incorporated herein by reference in their entirety.

STATEMENT REGARDING FEDERALLY SPONSORED RESEARCH

This invention was made with government support under 0950971 awarded by the National Science Foundation and under AI120977 and HL105704 awarded by the National Institutes of Health. The government has certain rights in the invention

INCORPORATION BY REFERENCE OF SEQUENCE LISTING

Accompanying this filing is a Sequence Listing entitled "Sequence-Listing_ST25.txt", created on Dec. 24, 2025 and having 6,425,783 bytes of data, machine formatted on IBM-PC, MS-Windows operating system. The sequence listing is hereby incorporated herein by reference in its entirety for all purposes.

INTRODUCTION

Bacterial adaptive immune systems employ CRISPRs (clustered regularly interspaced short palindromic repeats) and CRISPR-associated (Cas) proteins for RNA-guided nucleic acid cleavage. The CRISPR-Cas systems thereby confer adaptive immunity in bacteria and archaea via RNA-guided nucleic acid interference. To provide anti-viral immunity, processed CRISPR array transcripts (crRNAs) assemble with Cas protein-containing surveillance complexes that recognize nucleic acids bearing sequence complementarity to the virus derived segment of the crR-NAs, known as the spacer.

Class 2 CRISPR-Cas systems are streamlined versions in which a single Cas protein (an effector protein, e.g., a type V Cas effector protein such as Cpf1) bound to RNA is responsible for binding to and cleavage of a targeted sequence. The programmable nature of these minimal systems has facilitated their use as a versatile technology that continues to revolutionize the field of genome manipulation.

SUMMARY

The present disclosure provides methods for characterizing a target DNA present in a sample. The methods involve contacting the sample with a type V CRISPR/Cas effector protein and one or more guide RNAs, where the contacting step generates a cleavage product comprising a 5' overhang; and ligating a double-stranded nucleic acid adapter to the cleavage product, to generate a ligation product. The ligation product includes the target DNA, which can be sequenced. The sample can be subjected to one or more amplification steps prior to the contacting step, with primers that provide for amplification of nucleic acids of, e.g., specific pathogens, categories of pathogens, two or more different pathogens, or two or more different categories of pathogens.

BRIEF DESCRIPTION OF THE DRAWINGS

FIG. 5 provides Table 2, which provides examples of crRNA and clicker sequences (from top to bottom: SEQ ID NO:29 to 38, 17383, and 39 to 40 in order of appearance.

FIG. 6A-6V provide amino acid sequences of various Type V CRISPR/Cas effector proteins (depicted are Cas12b sequences) (FIG. 6A-6J; from top to bottom: SEQ ID NO:41 to SEQ ID NO:50); amino acid sequences of various Type V CRISPR/Cas effector proteins (depicted are Cas12a and Cas12b sequences) (FIG. 6K-6T; from top to bottom: SEQ ID NO:51 to SEQ ID NO:60); and example guide RNA sequences (e.g., crRNA repeat sequences and an example single guide RNA sequence) and example PAM sequences (FIG. 6U (SEQ ID NO:61 to 67) and FIG. 6V (SEQ ID NO:68)).

FIG. 7A-7B provide amino acid sequences of Type V CRISPR/Cas effector proteins (depicted are Cas12e sequences) (A) SEQ ID NO:69: (B) SEQ ID NO:7.

FIG. 8 provides a list of target antibiotic resistance genes.

FIG. 1A-10B provide an algorithm for primer design and a sequencing workflow.

FIG. 11 provides a table showing detection of targeted viruses using MSSPE.

FIG. 12 provides a table showing viral genome coverage using MSSPE.

FIG. 13 provides a table showing detection of untargeted emerging or novel viruses using MSSPE.

DEFINITIONS

Figure 1:
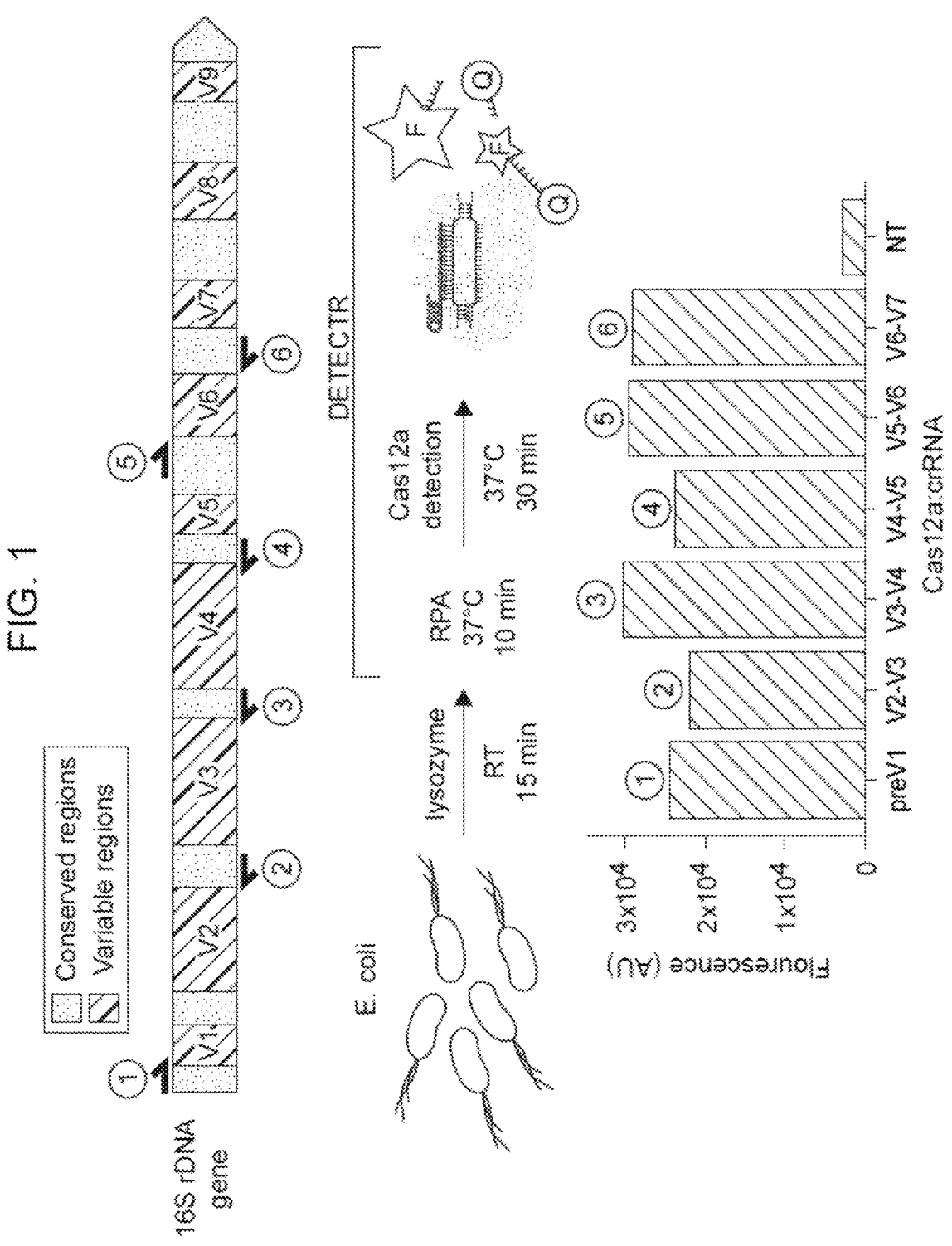
FIG. 1 depicts detection of *Escherichia coli* DNA using a Cas12a effector protein and guide RNAs targeting conserved regions of 16S rDNA. Using this system (referred to as "DETECTR", *E. coli* DNA can be detected within 30 minutes.
Figure 2:
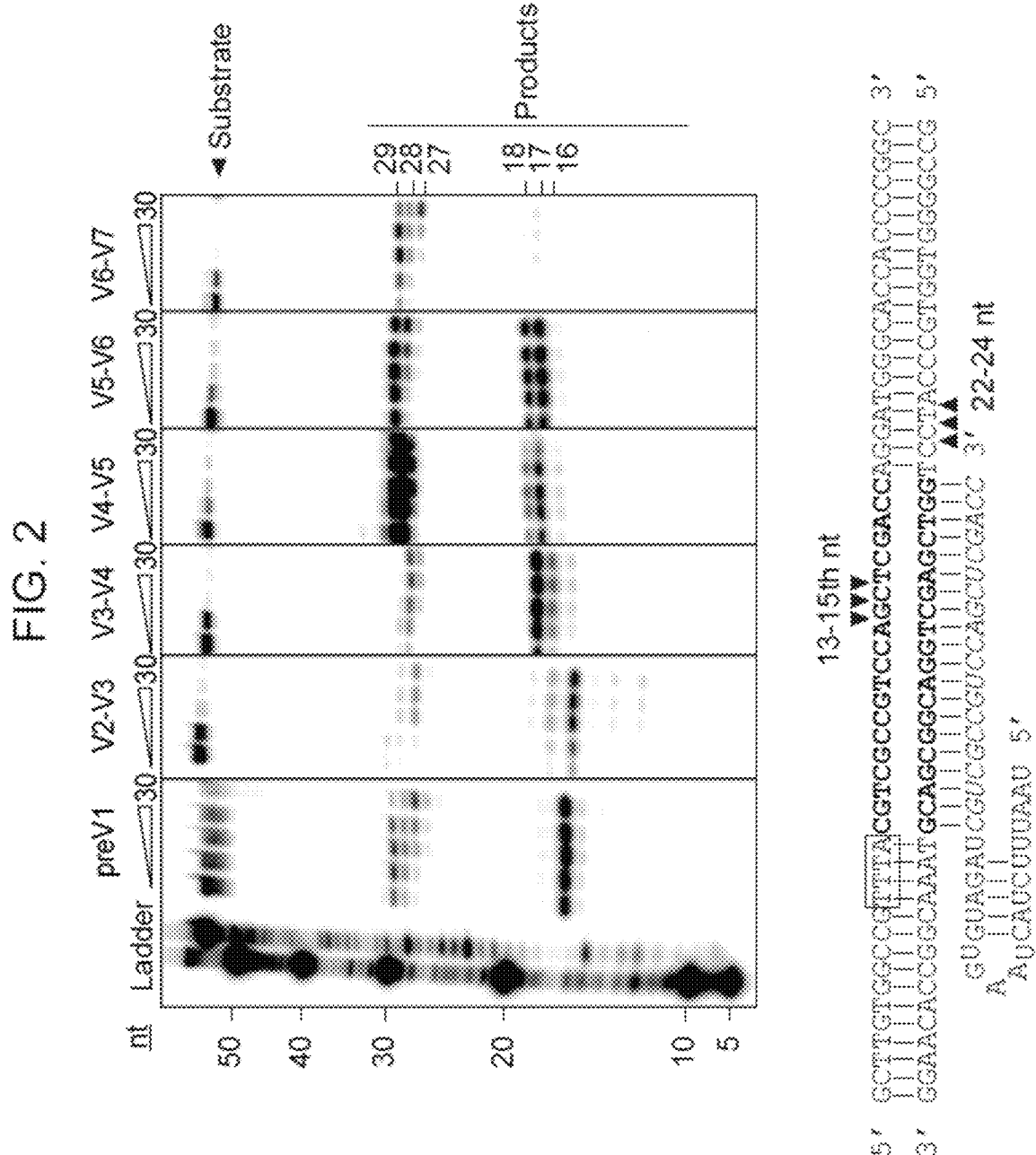
FIG. 2 depicts cleavage site mapping of 16S rDNA target sequences. Substrates were 5' radiolabelled and mapped on a denaturing polyacrylamide gel electrophoresis (PAGE) gel to identify cleavage sites. LbCas12a leaves an 8-10 nucleotide 5' overhang. (SEQ ID NO:19, 17379 and 17380 in order of appearance).

The terms "polynucleotide" and "nucleic acid," used interchangeably herein, refer to a polymeric form of nucleotides of any length, either ribonucleotides or deoxyribonucleotides. Thus, terms "polynucleotide" and "nucleic acid" encompass single-stranded DNA; double-stranded DNA; multi-stranded DNA; single-stranded RNA; double-stranded RNA; multi-stranded RNA; genomic DNA; cDNA; DNA-RNA hybrids; and a polymer comprising purine and pyrimidine bases or other natural, chemically or biochemically modified, non-natural, or derivatized nucleotide bases.

The term "oligonucleotide" refers to a polynucleotide of between 4 and 100 nucleotides of single- or double-stranded nucleic acid (e.g., DNA, RNA, or a modified nucleic acid). However, for the purposes of this disclosure, there is no upper limit to the length of an oligonucleotide. Oligonucleotides are also known as "oligomers" or "oligos" and can be isolated from genes, transcribed (in vitro and/or in vivo), or chemically synthesized. The terms "polynucleotide" and "nucleic acid" should be understood to include, as applicable to the embodiments being described, single-stranded (such as sense or antisense) and double-stranded polynucleotides.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine/adenosine) (A) pairing with thymidine/thymidine T), A pairing with uracil/uridine (U), and guanine/guanosine) (G) pairing with cytosine/cytidine (C). In addition, for hybridization between two RNA molecules (e.g., dsRNA), and for hybridization of a DNA molecule with an RNA molecule (e.g., when a DNA target nucleic acid base pairs with a guide RNA, etc.): G can also base pair with U. For example, G/U base-pairing is partially responsible for the degeneracy (i.e., redundancy) of the genetic code in the context of tRNA anti-codon base-pairing with codons in mRNA. Thus, in the context of this disclosure, a G (e.g., of a protein-binding segment (e.g., dsRNA duplex) of a guide RNA molecule; of a target nucleic acid (e.g., target DNA) base pairing with a guide RNA) is considered complementary to both a U and to C. For example, when a G/U base-pair can be made at a given nucleotide position of a protein-binding segment (e.g., dsRNA duplex) of a guide RNA molecule, the position is not considered to be non-complementary, but is instead considered to be complementary.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more).

It is understood that the sequence of a polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure, a 'bulge', and the like). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. The remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Example methods include BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), e.g., using default settings, which uses the algorithm of Smith and Waterman (Adv. Appl. Math., 1981, 2, 482-489).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to an RNA-binding domain of a polypeptide, binding to a target nucleic acid, and the like) refers to a non-covalent interaction between macromolecules (e.g., between a protein and a nucleic acid; between a guide RNA and a target nucleic acid; and the like). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant ($K_d$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_d$.

By "binding domain" it is meant a protein domain that is able to bind non-covalently to another molecule. A binding domain can bind to, for example, an RNA molecule (an RNA-binding domain) and/or a protein molecule (a protein-binding domain). In the case of a protein having a protein-binding domain, it can in some cases bind to itself (to form homodimers, homotrimers, etc.) and/or it can bind to one or more regions of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various methods and computer programs (e.g., BLAST, T-COFFEE, MUSCLE, MAFFT, Phyre2, etc.), available over the world wide web at sites including ncbi.nlm.nili.gov/BLAST, ebi.ac.uk/Tools/msa/tcoffee/, ebi.ac.uk/Tools/msa/muscle/, maff.cbrc.jp/alignment/software/, http://www.sbg.bio.ic.a-c.uk/~phyre2/. See, e.g., Altschul et al. (1990), *J. Mol. Biol.* 215:403-10.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a type V CRISPR/Cas effector polypeptide" includes a plurality of such polypeptides and reference to "the guide RNA" includes reference to one or more guide RNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods for characterizing a target DNA that is present in a sample. The methods involve contacting the sample with a type V CRISPR/Cas effector protein and one or more guide RNAs, where the contacting step generates a protospacer-adjacent motif (PAM)-distal cleavage product comprising a 5' overhang; and ligating a double-stranded nucleic acid adapter to the cleavage product, to generate a ligation product. The double-stranded nucleic acid adapter comprises a 5' overhang that comprises a stretch of from 3 to 15 contiguous nucleotides that are complementary to a contiguous stretch of nucleotides of the same length in the 5' overhang of the PAM-distal cleavage product. The ligation product includes the target DNA, which can be sequenced. The sample can be subjected to one or more amplification steps prior to the contacting step, with primers that provide for amplification of nucleic acids of, e.g., specific pathogens, categories of pathogens, two or more different pathogens, or two or more different categories of pathogens. The pre-amplified sample can also be contacted with a ssDNA reporter molecule that provides a readout when the type V CRISPR/Cas effector contacts the target DNA. The present disclosure provides a kit comprising components for carrying out a method of the present disclosure.

A kit or method of the present disclosure finds use in a wide variety of areas, including, e.g., infectious disease identification, and the like.

Methods for Characterizing a Target DNA

The present disclosure provides methods for characterizing a target DNA that is present in a sample. The methods involve contacting the sample with a type V CRISPR/Cas effector protein and one or more guide RNAs, where the contacting step generates a protospacer-adjacent motif (PAM)-distal cleavage product comprising a 5' overhang; and ligating a double-stranded nucleic acid adapter to the cleavage product, to generate a ligation product. The double-stranded nucleic acid adapter comprises a 5' overhang that comprises a stretch of from 3 to 15 contiguous nucleotides that are complementary to a contiguous stretch of nucleotides of the same length in the 5' overhang of the PAM-distal cleavage product. The ligation product includes the target DNA, which can be sequenced. The sample can be subjected to one or more amplification steps prior to the contacting step, with primers that provide for amplification of nucleic acids of, e.g., specific pathogens, categories of pathogens, two or more different pathogens, or two or more different categories of pathogens. The sample can also be subjected to one or more nucleic acid modification steps before contacting the sample with a type V CRISPR/Cas effector protein and/or prior to ligation. The sample can also be contacted with a ssDNA reporter molecule (a labelled single-stranded detector DNA), a guide RNA, and a type V CRISPR/Cas effector protein, such that, upon contact with a target DNA present in the sample, a signal is produced. For example, in some cases, a method of the present disclosure comprises: a) contacting a sample comprising (or suspected of comprising) a target nucleic acid with: i) a type V CRISPR/Cas effector polypeptide; ii) a guide RNA; and iii) a labelled single-stranded detector DNA, where the labelled single-stranded detector DNA produces a signal when the target nucleic acid is present in the sample, and where the contacting step generates a PAM-distal cleavage product comprising a 5' overhang; and b) and ligating a double-stranded nucleic acid adapter to the cleavage product, to generate a ligation product. In some cases, a method of the present disclosure comprises: a) contacting a sample comprising (or suspected of comprising) a target nucleic acid with one or more amplification primers or primer pairs, thereby generating an amplification product(s); b) contacting the sample comprising the amplification product(s) with: i) a type V CRISPR/Cas effector polypeptide; ii) a guide RNA; and iii) a labelled single-stranded detector DNA, where the labelled single-stranded detector DNA produces a signal when the target nucleic acid is present in the sample, and where the contacting step generates a PAM-distal cleavage product comprising a 5' overhang; and c) and ligating a double-stranded nucleic acid adapter to the cleavage product, to generate a ligation product. In some cases, a method of the present disclosure comprises: a) contacting a sample comprising (or suspected of comprising) a target ribonucleic acid with a reverse transcriptase, thereby generating a target DNA; b) contacting the sample comprising the comprising the target DNA with: i) a type V CRISPR/Cas effector polypeptide; ii) a guide RNA; and iii) a labelled single-stranded detector DNA, where the labelled single-stranded detector DNA produces a signal when the target nucleic acid is present in the sample, and where the contacting step generates a PAM-distal cleavage product comprising a 5' overhang; and c) and ligating a double-stranded nucleic acid adapter to the cleavage product, to generate a ligation product. In some cases, a method of the present disclosure comprises: a) contacting a sample comprising (or suspected of comprising) a target ribonucleic acid with a reverse transcriptase, thereby generating a target DNA; b) contacting the sample comprising the target DNA with one or more amplification primers or primer pairs, thereby generating an amplification product(s); c) contacting the sample comprising the amplification product(s) with: i) a type V CRISPR/Cas effector polypeptide; ii) a guide RNA; and iii) a labelled single-stranded detector DNA, where the labelled single-stranded detector DNA produces a signal when the target nucleic acid is present in the sample, and where the contacting step generates a PAM-distal cleavage product comprising a 5' overhang; and d) and ligating a double-stranded nucleic acid adapter to the cleavage product, to generate a ligation product.

As noted above, in some cases, the ligation product is sequenced; e.g., the target DNA present in the ligation product is sequenced. The contacting, ligating, and sequencing steps can be carried out in a single reaction container (also referred to herein as a "reaction vessel"). Thus, in a single reaction container, a target DNA can be both detected and sequenced. In some cases, the contacting and ligating steps are carried out in a first reaction container, and the sequencing step is carried out in a second reaction container.

Figure 3:
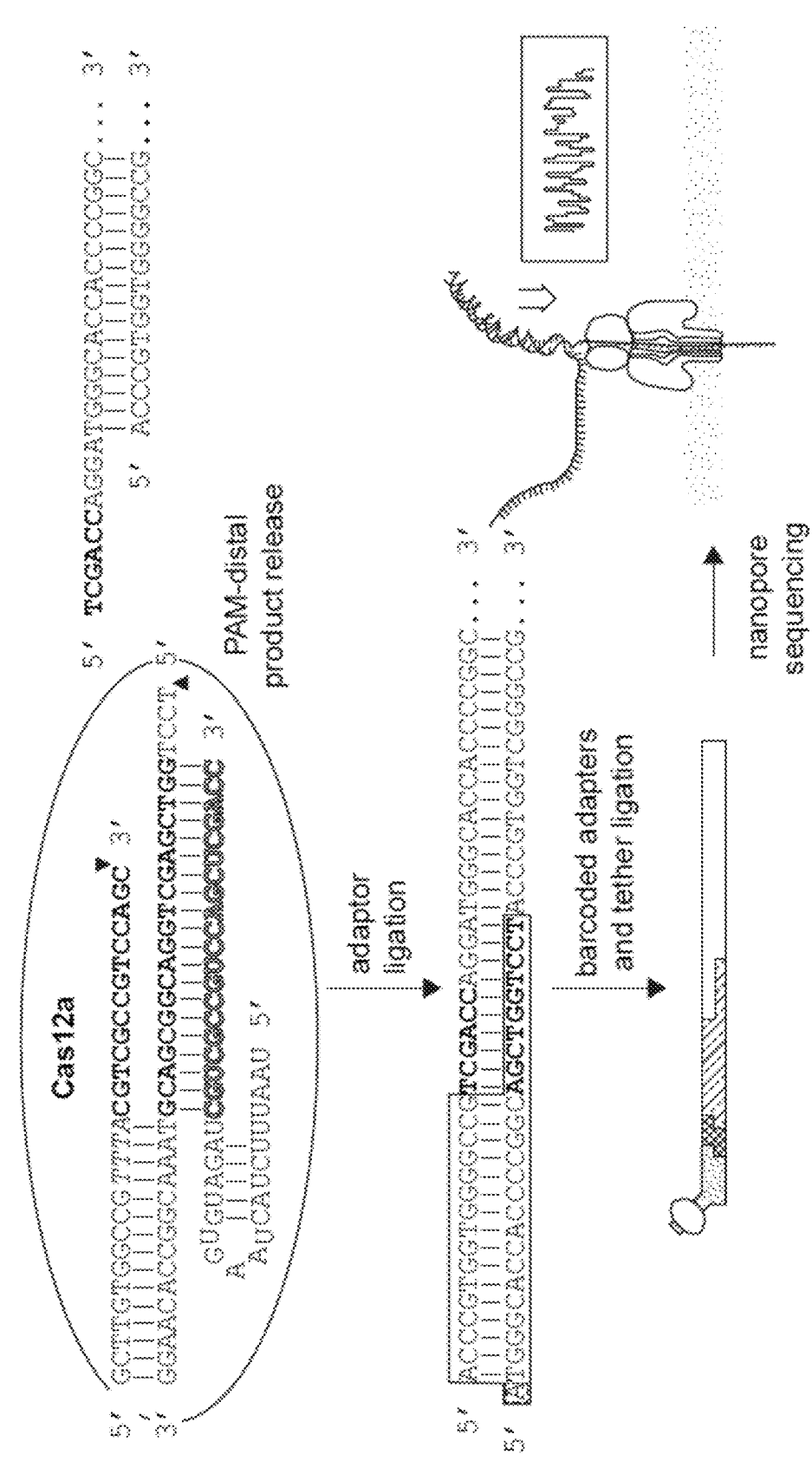
FIG. 3 is a schematic depiction of Cas12 cleavage and adapter ligation for nanopore sequencing. Following Cas12a cleavage (depicted are SEQ ID NO:22, 17381 and 17382) and DNA detection, the PAM-distal product containing a 5' overhang is released from the complex (SEQ ID NO:24 and 25), which is simultaneously ligated to a "dicker" molecule (also referred to herein as an "adapter") that can be directly coupled with next-generation sequencing protocols. The "clicker" contains a sequence complementary to the cleaved product for selective ligation and a 3' dA for adapter ligation (e.g., ligation to further adapters)(SEQ ID NO:27 and 28).
Figure 4:
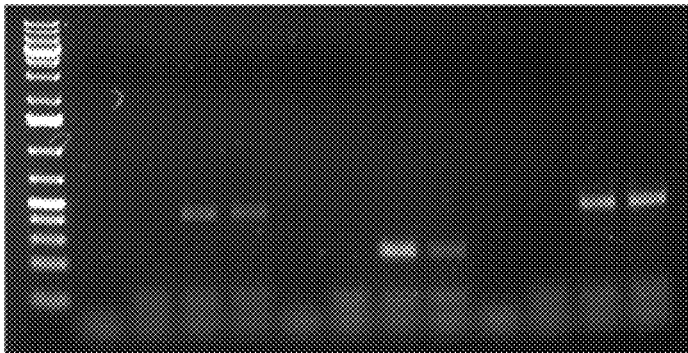
FIG. 4 depicts polymerase chain reaction (PCR) verification of clicker ligation using polymerase chain reaction (PCR). 16S rDNA sequences were amplified from genomic *E. coli* DNA and treated with the conditions indicated in the figure. The strand of the clicker molecule containing the 3' dA and complementary sequence was phosphorylated. Cas12-crRNA cleavage and clicker ligation were performed in a single step, in the presence of 1× binding buffer and 1×T4 ligase buffer at room temperature for 1 hour. Cleavage/ligation was verified by PCR amplification using a forward primer specific to the clicker and a reverse primer specific to the cleaved product.

Cleavage of a target DNA with a type V CRISPR/Cas effector polypeptide (e.g., a Cas12 polypeptide) generates a cleavage product having a 5' overhang of from about 4 nucleotides to about 12 nucleotides in length. This 5' overhang can provide a point of hybridization for an adapter molecule (e.g., a double-stranded nucleic acid adapter) having a 5' overhang with a nucleotide sequence that is at least partially complementary to the nucleotide sequence of the 5' overhang of the type V CRISPR/Cas effector polypeptide cleavage product. The adapter molecule can be ligated to the type V CRISPR/Cas effector polypeptide cleavage product, generating a type V CRISPR/Cas effector polypeptide cleavage product/adapter hybrid nucleic acid. The type V CRISPR/Cas effector polypeptide cleavage product/adapter hybrid nucleic acid can be ligated to one or more additional adapters, e.g., an adapter that provides a bar code, an adapter that allows for next-generation sequencing, and the like. For example, the one or more additional adapters can include a nucleotide sequence specific for coupling to a sequencing platform; such an adapter may also include a barcode sequence. In some cases, the additional adapter comprises a nucleotide sequence that is at least 70% identical to a support-bound oligonucleotide conjugated to a solid support; in some cases, the solid support is coupled to a sequencing platform. In some cases, the additional adapter comprises a binding site for a sequencing primer. Ligation of various adapters to a type V CRISPR/Cas effector polypeptide cleavage product is depicted schematically in FIG. 3.

The contacting step of a subject method can be carried out in a composition comprising divalent metal ions. The contacting step can be carried out in an acellular environment, e.g., outside of a cell. The contacting step can be carried out inside a cell. The contacting step can be carried out in a cell in vitro. The contacting step can be carried out in a cell ex vivo. The contacting step can be carried out in a cell in vivo.

As noted above, nucleic acid(s) present in a sample can be subjected to one or more nucleic acid modification steps before contacting the sample with a type V CRISPR/Cas effector protein and/or prior to ligation. For example, in some cases, a dsDNA can be subjected to dephosphorylation prior to cleavage with a type V CRISPR/Cas effector protein. The dephosphorylation step would avoid sequencing of dsDNA not cleaved by the type V CRISPR/Cas effector protein. As another example, in some cases, a dsDNA is cleaved with a type V CRISPR/Cas effector protein and, prior to ligation with a double-stranded nucleic acid adapter, the cleavage product is subjected to Klenow repair of overhangs, e.g., to fill in a 3' overhang.

The guide RNA can be provided as RNA or as a nucleic acid encoding the guide RNA (e.g., a DNA such as a recombinant expression vector). The Type V CRISPR/Cas effector protein (e.g., a Cas12 protein such as Cas12a, Cas12b, Cas12c, Cas12d, Cas12e) can be provided as a protein or as a nucleic acid encoding the protein (e.g., an mRNA, a DNA such as a recombinant expression vector). In some cases, two or more (e.g., 3 or more, 4 or more, 5 or more, or 6 or more) guide RNAs can be provided by (e.g., using a precursor guide RNA array, which can be cleaved by the Type V CRISPR/Cas effector protein into individual ("mature") guide RNAs).

In some cases (e.g., when contacting with a guide RNA and a Type V CRISPR/Cas effector protein (e.g., a Cas12 protein such as Cas12a, Cas12b, Cas12c, Cas12d, Cas12e)), the sample is contacted for 2 hours or less (e.g., 1.5 hours or less, 1 hour or less, 40 minutes or less, 30 minutes or less, 20 minutes or less, 10 minutes or less, or 5 minutes or less, or 1 minute or less) prior to the ligating step. For example, in some cases, the sample is contacted for 40 minutes or less prior to the ligating step. In some cases, the sample is contacted for 20 minutes or less prior to the ligating step. In some cases, the sample is contacted for 10 minutes or less prior to the ligating step. In some cases, the sample is contacted for 5 minutes or less prior to the ligating step. In some cases, the sample is contacted for 1 minute or less prior to the ligating step. In some cases, the sample is contacted for from 50 seconds to 60 seconds prior to the ligating step. In some cases, the sample is contacted for from 40 seconds to 50 seconds prior to the ligating step. In some cases, the sample is contacted for from 30 seconds to 40 seconds prior to the ligating step. In some cases, the sample is contacted for from 20 seconds to 30 seconds prior to the ligating step. In some cases, the sample is contacted for from 10 seconds to 20 seconds prior to the ligating step.

A method of the present disclosure for characterizing a target DNA (single-stranded or double-stranded) in a sample can provide for characterization of a target DNA with a high degree of sensitivity. In some cases, a method of the present disclosure can be used to characterize a target DNA present in a sample comprising a plurality of DNAs (including the target DNA and a plurality of non-target DNAs), where the target DNA is present at one or more copies per $10^7$ non-target DNAs (e.g., one or more copies per $10^6$ non-target DNAs, one or more copies per $10^5$ non-target DNAs, one or more copies per $10^4$ non-target DNAs, one or more copies per $10^3$ non-target DNAs, one or more copies per $10^2$ non-target DNAs, one or more copies per 50 non-target DNAs, one or more copies per 20 non-target DNAs, one or more copies per 10 non-target DNAs, or one or more copies per 5 non-target DNAs). In some cases, a method of the present disclosure can be used to characterize a target DNA present in a sample comprising a plurality of DNAs (including the target DNA and a plurality of non-target DNAs), where the target DNA is present at one or more copies per $10^{18}$ non-target DNAs (e.g., one or more copies per $10^{15}$ non-target DNAs, one or more copies per $10^{12}$ non-target DNAs, one or more copies per $10^9$ non-target DNAs, one or more copies per $10^6$ non-target DNAs, one or more copies per $10^5$ non-target DNAs, one or more copies per $10^4$ non-target DNAs, one or more copies per $10^3$ non-target DNAs, one or more copies per $10^2$ non-target DNAs, one or more copies per 50 non-target DNAs, one or more copies per 20 non-target DNAs, one or more copies per 10 non-target DNAs, or one or more copies per 5 non-target DNAs).

In some cases, a method of the present disclosure can characterize a target DNA present in a sample, where the target DNA is present at from one copy per $10^7$ non-target DNAs to one copy per 10 non-target DNAs (e.g., from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 10 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 10 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, a method of the present disclosure can characterize a target DNA present in a sample, where the target DNA is present at from one copy per $10^{18}$ non-target DNAs to one copy per 10 non-target DNAs (e.g., from 1 copy per $10^{18}$ non-target DNAs to 1 copy per $10^2$ non-target DNAs, from 1 copy per $10^{15}$ non-target DNAs to 1 copy per $10^2$ non-target DNAs, from 1 copy per $10^{12}$ non-target DNAs to 1 copy per $10^2$ non-target DNAs, from 1 copy per $10^9$ non-target DNAs to 1 copy per $10^2$ non-target DNAs, from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 10 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 10 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, a method of the present disclosure can characterize a target DNA present in a sample, where the target DNA is present at from one copy per $10^7$ non-target DNAs to one copy per 100 non-target DNAs (e.g., from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 100 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 100 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, the target DNA is present in the sample at a concentration of 10 nM or less, e.g., from about 1 attomolar (aM) to about 100 aM, from about 100 aM to about 500 aM, from about 500 aM to about 1 femtomolar (fM), from about 1 fM to about 100 fM, from about 100 fM to about 500 fM, from about 500 fM to about 1 picomolar (pM), from about 1 pM to about 100 pM, from about 100 pM to about 500 pM, from about 500 pM to about 1 nanomolar (nM), from about 1 nM to about 100 nM, from about 100 nM to about 500 nM, or from about 500 nM to about 1 μM, or more than 1 μM.

In some cases, the target DNA is present in the sample at a concentration of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, Type V CRISPR/Cas Effector Proteins As noted above, a method of the present disclosure includes use of a Type V CRISPR/Cas effector polypeptide, where a sample that comprises, or is suspected of comprising, a target DNA is contacted with a Type V CRISPR/Cas effector polypeptide and one or more guide RNAs. Type V CRISPR/Cas effector proteins are a subtype of Class 2 CRISPR/Cas effector proteins. For examples of type V CRISPR/Cas systems and their effector proteins (e.g., Cas12 family proteins such as Cas12a), see, e.g., Shmakov et al., Nat Rev Microbiol. 2017 March; 15(3):169-182: "Diversity and evolution of class 2 CRISPR-Cas systems." Examples include, but are not limited to: Cas12 family (Cas12a, Cas12b, Cas12c), C2c4, C2c8, C2c5, C2c10, and C2c9; as well as CasX (Cas12e) and CasY (Cas12d). Also see, e.g., Koonin et al., Curr Opin Microbiol. 2017 June; 37:67-78: "Diversity, classification and evolution of CRISPR-Cas systems."

In some cases, a type V CRISPR/Cas effector protein suitable for use in a method of the present disclosure is a Cas12 protein (e.g., Cas12a, Cas12b, Cas12c). In some cases, a suitable type V CRISPR/Cas effector protein is a Cas12 protein such as Cas12a, Cas12b, Cas12c, Cas12d, Cas12e, Cas12d, or Cas12e. In some cases, a suitable type V CRISPR/Cas effector protein is a Cas12a protein. In some cases, a suitable type V CRISPR/Cas effector protein is a Cas12b protein. In some cases, a suitable type V CRISPR/Cas effector protein is a Cas12c protein. In some cases, a suitable type V CRISPR/Cas effector protein is a Cas12d protein. In some cases, a suitable type V CRISPR/Cas effector protein is a Cas12e protein. In some cases, a suitable type V CRISPR/Cas effector protein is protein selected from: Cas12 (e.g., Cas12a, Cas12b, Cas12c, Cas12d, Cas12e), C2c4, C2c8, C2c5, C2c00, and C2c9. In some cases, a suitable type V CRISPR/Cas effector protein is protein selected from: C2c4, C2c8, C2c5, C2c00, and C2c9. In some cases, a suitable type V CRISPR/Cas effector protein is protein selected from: C2c4, C2c8, and C2c5. In some cases, a suitable type V CRISPR/Cas effector protein is protein selected from: C2c10 and C2c9.

In some cases, a suitable type V CRISPR/Cas effector protein is a naturally-occurring protein (e.g., naturally occurs in prokaryotic cells). In other cases, the Type V CRISPR/Cas effector protein is not a naturally-occurring polypeptide (e.g., the effector protein is a variant protein, a chimeric protein, includes a fusion partner, and the like). Examples of naturally occurring Type V CRISPR/Cas effector proteins include, but are not limited to, those depicted in FIG. 6 (e.g., FIG. 6A-6T). Any Type V CRISPR/Cas effector protein can be suitable for the compositions (e.g., nucleic acids, kits, etc.) and methods of the present disclosure (e.g., as long as the Type V CRISPR/Cas effector protein forms a complex with a guide RNA and exhibits ssDNA cleavage activity of non-target ssDNAs once it is activated (by hybridization of and associated guide RNA to its target DNA).

In some cases, a type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a Cas12 protein (e.g., Cas12a, Cas12b, Cas12c) (e.g., a Cas12 protein depicted in any one of FIG. 6A-6T). For example, In some cases, a type V CRISPR/Cas effector protein comprises an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a Cas12 protein (e.g., Cas12a, Cas12b, Cas12c) (e.g., a Cas12 protein depicted in FIG. 6). In some cases, a type V CRISPR/Cas effector protein comprises an amino acid sequence having 80% or more sequence identity (e.g., 85% or more, 90% or more, 95% or more, 97% or more, 98% or more, 99% or more, or 100% sequence identity) with a Cas12 protein (e.g., Cas12a, Cas12b, Cas12c) (e.g., a Cas12 protein depicted in any one of FIG. 6A-6T). In some cases, a type V CRISPR/Cas effector protein comprises an amino acid sequence having 90% or more sequence identity (e.g., 95% or more, 97% or more, 98% or more, 99% or more, or 100% sequence identity) with a Cas12 protein (e.g., Cas12a, Cas12b, Cas12c) (e.g., a Cas12 protein depicted in FIG. 6). In some cases, a type V CRISPR/Cas effector protein comprises a Cas12 amino acid sequence (e.g., Cas12a, Cas12b, Cas12c) depicted in any one of FIG. 6A-6T.

In some cases, a type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a Cas12a protein (e.g., a Cas12a protein depicted in any FIG. 6). For example, in some cases, a type V CRISPR/Cas effector protein comprises an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a Cas12a protein (e.g., a Cas12a protein depicted in FIG. 6). In some cases, a type V CRISPR/Cas effector protein comprises an amino acid sequence having 80% or more sequence identity (e.g., 85% or more, 90% or more, 95% or more, 97% or more, 98% or more, 99% or more, or 100% sequence identity) with a Cas12a protein (e.g., a Cas12a protein depicted in FIG. 6). In some cases, a type V CRISPR/Cas effector protein comprises an amino acid sequence having 90% or more sequence identity (e.g., 95% or more, 97% or more, 98% or more, 99% or more, or 100% sequence identity) with a Cas12a protein (e.g., a Cas12a protein depicted in FIG. 6). In some cases, a type V CRISPR/Cas effector protein comprises a Cas12a amino acid sequence depicted in FIG. 6.

In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Lachnospiraceae bacterium ND2006 Cas12a protein amino acid sequence depicted in FIG. 6. In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the *Acidaminococcus* spBV3L6 Cas12a protein amino acid sequence depicted in FIG. 6. In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the *Francisella novicida* U112 Cas12a protein amino acid sequence depicted in FIG. 6. In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the *Porphyromonas macacae* Cas12a protein amino acid sequence depicted in FIG. 6. In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the *Moraxella bovoculi* 237 Cas12a protein amino acid sequence depicted in FIG. 6. In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the *Moraxella bovoculi* AAX08_00205 Cas12a protein amino acid sequence depicted in FIG. 6. In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the *Moraxella bovoculi* AAX11_00205 Cas12a protein amino acid sequence depicted in FIG. 6. In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the *Thiomicrospira* sp. XSS Cas12a protein amino acid sequence depicted in FIG. 6. In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the *Butyrivibrio* sp. NC3005 Cas12a protein amino acid sequence depicted in FIG. 6. In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the AACCas12b amino acid sequence depicted in FIG. 6.

In some cases, a type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a Cas12b protein (e.g., a Cas12b protein depicted in FIG. 6). For example, in some cases, a type V CRISPR/Cas effector protein comprises an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a Cas12b protein (e.g., a Cas12b protein depicted in FIG. 6). In some cases, a type V CRISPR/Cas effector protein comprises an amino acid sequence having 80% or more sequence identity (e.g., 85% or more, 90% or more, 95% or more, 97% or more, 98% or more, 99% or more, or 100% sequence identity) with a Cas12b protein (e.g., a Cas12b protein depicted in FIG. 6). In some cases, a type V CRISPR/Cas effector protein comprises an amino acid sequence having 90% or more sequence identity (e.g., 95% or more, 97% or more, 98% or more, 99% or more, or 100% sequence identity) with a Cas12b protein (e.g., a Cas12b protein depicted in FIG. 6). In some cases, a type V CRISPR/Cas effector protein comprises a Cas12b amino acid sequence depicted in FIG. 6.

In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12b amino acid sequence depicted in FIG. 6A.

In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12b amino acid sequence depicted in FIG. 6B.

In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12b amino acid sequence depicted in FIG. 6C.

In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12b amino acid sequence depicted in FIG. 6D.

In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12b amino acid sequence depicted in FIG. 6E.

In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12b amino acid sequence depicted in FIG. 6F.

In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12b amino acid sequence depicted in FIG. 6G.

In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12b amino acid sequence depicted in FIG. 6H.

In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12b amino acid sequence depicted in FIG. 6I.

In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12b amino acid sequence depicted in FIG. 6J.

In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12e amino acid sequence depicted in FIG. 7A.

In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12e amino acid sequence depicted in FIG. 7B.

In some cases, a type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a Cas12, C2c4, C2c8, C2c5, C2c10, or C2c9 protein. For example, in some cases, a type V CRISPR/Cas effector protein comprises an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a Cas12, C2c4, C2c8, C2c5, C2c10, or C2c9 protein. In some cases, a type V CRISPR/Cas effector protein comprises an amino acid sequence having 80% or more sequence identity (e.g., 85% or more, 90% or more, 95% or more, 97% or more, 98% or more, 99% or more, or 100% sequence identity) with a Cas12, C2c4, C2c8, C2c5, C2c10, or C2c9 protein. In some cases, a type V CRISPR/Cas effector protein comprises an amino acid sequence having 90% or more sequence identity (e.g., 95% or more, 97% or more, 98% or more, 99% or more, or 100% sequence identity) with a Cas12, C2c4, C2c8, C2c5, C2c10, or C2c9 protein. In some cases, a type V CRISPR/Cas effector protein comprises a Cas12, C2c4, C2c8, C2c5, C2c10, or C2c9 amino acid sequence.

In some cases, a type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a Cas12, C2c4, C2c8, or C2c5 protein. For example, In some cases, a type V CRISPR/Cas effector protein comprises an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a Cas12, C2c4, C2c8, or C2c5 protein. In some cases, a type V CRISPR/Cas effector protein comprises an amino acid sequence having 80% or more sequence identity (e.g., 85% or more, 90% or more, 95% or more, 97% or more, 98% or more, 99% or more, or 100% sequence identity) with a Cas12, C2c4, C2c8, or C2c5 protein. In some cases, a type V CRISPR/Cas effector protein comprises an amino acid sequence having 90% or more sequence identity (e.g., 95% or more, 97% or more, 98% or more, 99% or more, or 100% sequence identity) with a Cas12, C2c4, C2c8, or C2c5 protein. In some cases, a type V CRISPR/Cas effector protein comprises a Cas12, C2c4, C2c8, or C2c5 amino acid sequence.

In some cases, a type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a C2c4, C2c8, or C2c5 protein. For example, in some cases, a type V CRISPR/Cas effector protein comprises an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a C2c4, C2c8, or C2c5 protein. In some cases, a type V CRISPR/Cas effector protein comprises an amino acid sequence having 80% or more sequence identity (e.g., 85% or more, 90% or more, 95% or more, 97% or more, 98% or more, 99% or more, or 100% sequence identity) with a C2c4, C2c8, or C2c5 protein. In some cases, a type V CRISPR/Cas effector protein comprises an amino acid sequence having 90% or more sequence identity (e.g., 95% or more, 97% or more, 98% or more, 99% or more, or 100% sequence identity) with a C2c4, C2c8, or C2c5 protein. In some cases, a type V CRISPR/Cas effector protein comprises a C2c4, C2c8, or C2c5 amino acid sequence.

In some cases, a type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a Cas12, C2c10, or C2c9 protein. For example, In some cases, a type V CRISPR/Cas effector protein comprises an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a Cas12, C2c10, or C2c9 protein. In some cases, a type V CRISPR/Cas effector protein comprises an amino acid sequence having 80% or more sequence identity (e.g., 85% or more, 90% or more, 95% or more, 97% or more, 98% or more, 99% or more, or 100% sequence identity) with a Cas12, C2c10, or C2c9 protein. In some cases, a type V CRISPR/Cas effector protein comprises an amino acid sequence having 90% or more sequence identity (e.g., 95% or more, 97% or more, 98% or more, 99% or more, or 100% sequence identity) with a Cas12, C2c10, or C2c9 protein. In some cases, a type V CRISPR/Cas effector protein comprises a Cas12, C2c10, or C2c9 amino acid sequence.

In some cases, a type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a C2c10 or C2c9 protein. For example, In some cases, a type V CRISPR/Cas effector protein comprises an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a C2c10 or C2c9 protein. In some cases, a type V CRISPR/Cas effector protein comprises an amino acid sequence having 80% or more sequence identity (e.g., 85% or more, 90% or more, 95% or more, 97% or more, 98% or more, 99% or more, or 100% sequence identity) with a C2c10 or C2c9 protein. In some cases, a type V CRISPR/Cas effector protein comprises an amino acid sequence having 90% or more sequence identity (e.g., 95% or more, 97% or more, 98% or more, 99% or more, or 100% sequence identity) with a C2c10 or C2c9 protein. In some cases, a type V CRISPR/Cas effector protein comprises a C2c10 or C2c9 amino acid sequence.

In some cases, a subject type V CRISPR/Cas effector protein (e.g., a Cas12 protein such as Cas12a, Cas12b, Cas12c, Cas12d, Cas12e) is fused to (conjugated to) a heterologous polypeptide. In some cases, a heterologous polypeptide (a fusion partner) provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an endoplasmic reticulum (ER) retention signal, and the like). In some cases, a type V CRISPR/Cas effector protein (e.g., a Cas12 protein) does not include a NLS so that the protein is not targeted to the nucleus (which can be advantageous, e.g., when it desirable to cleave non-target ssDNAs in the cytosol). In some cases, the heterologous polypeptide can provide a tag (i.e., the heterologous polypeptide is a detectable label) for ease of tracking and/or purification (e.g., a fluorescent protein, e.g., a green fluorescent protein (GFP), a yellow fluorescent protein (YFP), a red fluorescent protein (RFP), a cyan fluorescent protein (CFP), mCherry, tdTomato, and the like; a histidine tag, e.g., a 6×His tag; a hemagglutinin (HA) tag; a FLAG tag; a Myc tag; and the like).

In some cases, a type V CRISPR/Cas effector protein (e.g., a Cas12 protein such as Cas12a, Cas12b, Cas12c, Cas12d, Cas12e) includes (is fused to) a nuclear localization signal (NLS) (e.g., in some cases 2 or more, 3 or more, 4 or more, or 5 or more NLSs). Thus, in some cases, a type V CRISPR/Cas effector protein includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus.

In some cases, a type V CRISPR/Cas effector protein (e.g., a Cas12 protein such as Cas12a, Cas12b, Cas12c, Cas12d, Cas12e) includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases, a type V CRISPR/Cas effector protein includes (is fused to) between 2 and 5 NLSs (e.g., 2-4, or 2-3 NLSs).

Non-limiting examples of NLSs include an NLS sequence derived from: the NLS of the SV40 virus large T-antigen, having the amino acid sequence PKKKRKV (SEQ ID NO:1); the NLS from nucleoplasmin (e.g., the nucleoplasmin bipartite NLS with the sequence KRPAATKK-AGQAKKKK (SEQ ID NO:2)); the c-myc NLS having the amino acid sequence PAAKRVKLD (SEQ ID NO:3) or RQRRNELKRSP (SEQ ID NO:4); the hRNPA1 M9 NLS having the sequence NQSSNFGPMKGGNFGGRSSGP-YGGGGQYFAKPRNQGGY (SEQ ID NO:5); the sequence RMRIZFKNKGKDTAELRRRRVEVSVELRKAKKDEQ-ILKRRNV (SEQ ID NO:6) of the IBB domain from importin-alpha; the sequences VSRKRPRP (SEQ ID NO:7) and PPKKARED (SEQ ID NO:8) of the myoma T protein; the sequence PQPKKKPL (SEQ ID NO:9) of human p53; the sequence SALIKKKKKMAP (SEQ ID NO:10) of mouse c-abl IV; the sequences DRLRR (SEQ ID NO:11) and PKQKKRK (SEQ ID NO:12) of the influenza virus NS1; the sequence RKLKKKIKKL (SEQ ID NO:13) of the Hepatitis virus delta antigen; the sequence REKKKFLKRR (SEQ ID NO:14) of the mouse Mx1 protein; the sequence KRKGDEVDGVDEVAKKKSKK (SEQ ID NO:15) of the human poly(ADP-ribose) polymerase; and the sequence RKCLQAGMNLEARKTKK (SEQ ID NO:16) of the steroid hormone receptors (human) glucocorticoid. In general, NLS (or multiple NLSs) are of sufficient strength to drive accumulation of the protein in a detectable amount in the nucleus of a eukaryotic cell. Detection of accumulation in the nucleus may be performed by any suitable technique.

Protospacer Adjacent Motif (PAM)

A Type V CRISPR/Cas effector protein binds to target DNA at a target sequence defined by the region of complementarity between the DNA-targeting RNA and the target DNA. As is the case for many CRISPR/Cas endonucleases, site-specific binding (and/or cleavage) of a double stranded target DNA occurs at locations determined by both (i) base-pairing complementarity between the guide RNA and the target DNA; and (ii) a short motif (referred to as the protospacer adjacent motif (PAM)) in the target DNA.

In some cases, the PAM for a Type V CRISPR/Cas effector protein is immediately 5' of the target sequence (e.g., of the non-complementary strand of the target DNA— the complementary strand hybridizes to the guide sequence of the guide RNA while the non-complementary strand does not directly hybridize with the guide RNA and is the reverse complement of the non-complementary strand). In some cases (e.g., when Cas12a or Cas12b as described herein is used), the PAM sequence is 5'-TTN-3'. In some cases, the PAM sequence is 5'-TTTN-3'. (e.g., see FIG. 6V).

In some cases, different Type V CRISPR/Cas effector proteins (i.e., Type V CRISPR/Cas effector proteins from various species) may be advantageous to use in the various provided methods in order to capitalize on a desired feature (e.g., specific enzymatic characteristics of different Type V CRISPR/Cas effector proteins). Type V CRISPR/Cas effector proteins from different species may require different PAM sequences in the target DNA. Thus, for a particular Type V CRISPR/Cas effector protein of choice, the PAM sequence requirement may be different than the 5'-TTN-3' or 5'-TTTN-3' sequence described above. Various methods (including in silico and/or wet lab methods) for identification of the appropriate PAM sequence are known in the art and are routine, and any convenient method can be used.

Guide RNA

A nucleic acid molecule (e.g., a natural crRNA) that binds to a type V CRISPR/Cas effector protein (e.g., a Cas12 protein such as Cas12a, Cas12b, Cas12c, Cas12d, Cas12e), forming a ribonucleoprotein complex (RNP), and targets the complex to a specific target sequence within a target DNA is referred to herein as a "guide RNA." It is to be understood that in some cases, a hybrid DNA/RNA can be made such that a guide RNA includes DNA bases in addition to RNA bases—but the term "guide RNA" is still used herein to encompass such hybrid molecules. A subject guide RNA includes a guide sequence (also referred to as a "spacer") (that hybridizes to target sequence of a target DNA) and a constant region (e.g., a region that is adjacent to the guide sequence and binds to the type V CRISPR/Cas effector protein). A "constant region" can also be referred to herein as a "protein-binding segment." In some cases, e.g., for Cas12a, the constant region is 5' of the guide sequence.

Guide Sequence

The guide sequence has complementarity with (hybridizes to) a target sequence of the target DNA. In some cases, the guide sequence is 15-28 nucleotides (nt) in length (e.g., 15-26, 15-24, 15-22, 15-20, 15-18, 16-28, 16-26, 16-24, 16-22, 16-20, 16-18, 17-26, 17-24, 17-22, 17-20, 17-18, 18-26, 18-24, or 18-22 nt in length). In some cases, the guide sequence is 18-24 nucleotides (nt) in length. In some cases, the guide sequence is at least 15 nt long (e.g., at least 16, 18, 20, or 22 nt long). In some cases, the guide sequence is at least 17 nt long. In some cases, the guide sequence is at least 18 nt long. In some cases, the guide sequence is at least 20 nt long.

In some cases, the guide sequence has 80% or more (e.g., 85% or more, 90% or more, 95% or more, or 100% complementarity) with the target sequence of the target DNA. In some cases, the guide sequence is 100%6 complementary to the target sequence of the target DNA. In some cases, the target DNA includes at least 15 nucleotides (nt) of complementarity with the guide sequence of the guide RNA.

Guide sequences suitable for use in connection with detection of viral pathogens can be designed based on the nucleotide sequence of a viral pathogen. Guide sequences suitable for use in connection with detection of bacterial pathogens can be designed based on the nucleotide sequence of a bacterial pathogen. Guide sequences suitable for use in connection with detection of fungal pathogens can be designed based on the nucleotide sequence of a fungal pathogen. Guide sequences suitable for use in connection with detection of protozoan pathogens can be designed based on the nucleotide sequence of a protozoan pathogen. Guide sequences suitable for use in connection with detection of antibiotic resistance genes can be designed based on the nucleotide sequence of an antibiotic resistance gene.

Constant Region

Examples of constant regions for guide RNAs that can be used with a type V CRISPR/Cas effector protein (e.g., a Cas12 protein such as Cas12a, Cas12b, Cas12c, Cas12d, Cas12e) are presented in FIG. 6.

In some cases, a subject guide RNA includes a nucleotide sequence having 70% or more identity (e.g., 80% or more, 85% or more, 90% or more, 95% or more, 98% or more, 99% or more, or 100% identity) with any one of the crRNA repeat sequences set forth in FIG. 6. In some cases, a subject guide RNA includes a nucleotide sequence having 90% or more identity (e.g., 95% or more, 98% or more, 99% or more, or 100% identity) with any one of the crRNA repeat sequences set forth in FIG. 6. In some cases, a subject guide RNA includes a crRNA nucleotide sequence set forth in FIG. 6.

In some cases, the guide RNA includes a double stranded RNA duplex (dsRNA duplex). In some cases, a guide RNA includes a dsRNA duplex with a length of from 2 to 12 bp (e.g., from 2 to 10 bp, 2 to 8 bp, 2 to 6 bp, 2 to 5 bp, 2 to 4 bp, 3 to 12 bp, 3 to 10 bp, 3 to 8 bp, 3 to 6 bp, 3 to 5 bp, 3 to 4 bp, 4 to 12 bp, 4 to 10 bp, 4 to 8 bp, 4 to 6 bp, or 4 to 5 bp). In some cases, a guide RNA includes a dsRNA duplex that is 2 or more bp in length (e.g., 3 or more, 4 or more, 5 or more, 6 or more, or 7 or more bp in length). In some cases, a guide RNA includes a dsRNA duplex that is longer than the dsRNA duplex of a corresponding wild type guide RNA. In some cases, a guide RNA includes a dsRNA duplex that is shorter than the dsRNA duplex of a corresponding wild type guide RNA.

In some cases, the constant region of a guide RNA is 15 or more nucleotides (nt) in length (e.g., 18 or more, 20 or more, 21 or more, 22 or more, 23 or more, 24 or more, 25 or more, 26 or more, 27 or more, 28 or more, 29 or more, 30 or more, 31 or more nt, 32 or more, 33 or more, 34 or more, or 35 or more nt in length). In some cases, the constant region of a guide RNA is 18 or more nt in length.

In some cases, the constant region of a guide RNA has a length in a range of from 12 to 100 nt (e.g., from 12 to 90, 12 to 80, 12 to 70, 12 to 60, 12 to 50, 12 to 40, 15 to 100, 15 to 90, 15 to 80, 15 to 70, 15 to 60, 15 to 50, 15 to 40, 20 to 100, 20 to 90, 20 to 80, 20 to 70, 20 to 60, 20 to 50, 20 to 40, 25 to 100, 25 to 90, 25 to 80, 25 to 70, 25 to 60, 25 to 50, 25 to 40, 28 to 100, 28 to 90, 28 to 80, 28 to 70, 28 to 60, 28 to 50, 28 to 40, 29 to 100, 29 to 90, 29 to 80, 29 to 70, 29 to 60, 29 to 50, or 29 to 40 nt). In some cases, the constant region of a guide RNA has a length in a range of from 28 to 100 nt. In some cases, the region of a guide RNA that is 5' of the guide sequence has a length in a range of from 28 to 40 nt.

In some cases, the constant region of a guide RNA is truncated relative to (shorter than) the corresponding region of a corresponding wild type guide RNA. In some cases, the constant region of a guide RNA is extended relative to (longer than) the corresponding region of a corresponding wild type guide RNA. In some cases, a subject guide RNA is 30 or more nucleotides (nt) in length (e.g., 34 or more, 40 or more, 45 or more, 50 or more, 55 or more, 60 or more, 65 or more, 70 or more, or 80 or more nt in length). In some cases, the guide RNA is 35 or more nt in length.

Adapter Nucleic Acids

As noted above, a method of the present disclosure involves contacting the sample with a type V CRISPR/Cas effector protein and one or more guide RNAs, where the contacting step generates a PAM-distal cleavage product comprising a 5' overhang; and ligating a double-stranded nucleic acid adapter to the cleavage product, to generate a ligation product. The double-stranded nucleic acid adapter comprises a 5' overhang that comprises a stretch of from 3 to 15 contiguous nucleotides that are complementary to a contiguous stretch of nucleotides of the same length in the 5' overhang of the PAM-distal cleavage product. The ligation product includes the target DNA, which can be sequenced.

An adapter nucleic acid includes any nucleic acid having a sequence, at least a portion of which is known, that can be joined to a target polynucleotide. Adapter nucleic acids can comprise DNA, RNA, nucleotide analogues, non-canonical nucleotides, labeled nucleotides, modified nucleotides, or combinations thereof. Adapter nucleic acids can be single-stranded, double-stranded, or partial duplex. In general, a partial-duplex adapter comprises one or more single-stranded regions and one or more double-stranded regions. A partial-duplex adapter can be described as a "double-stranded nucleic acid adapter comprising a 5' overhang" (i.e., a 5' single-stranded overhang).

An adapter nucleic acid for use in a method of the present disclosure is double stranded, and comprises a 5' overhang that comprises a stretch of from 3 to 15 contiguous nucleotides that are complementary to a contiguous stretch of nucleotides of the same length in the 5' overhang of the PAM-distal cleavage product. In some cases, the 5' overhang has a length of from 3 nucleotides to 20 nucleotides; for example, the 5' overhang of the adapter nucleic acid can have a length of 3 nucleotides (nt), 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, or 20 nt. In some cases, the 5' overhang has a length of from 8 nucleotides to 10 nucleotides. In some cases, the 5' overhang has a length of 8 nucleotides. In some cases, the 5' overhang has a length of 9 nucleotides. In some cases, the 5' overhang has a length of 10 nucleotides. The 5' overhang of the adapter nucleic acid can comprise a stretch of 3, 4, 5, 6, 7, 8, 9, 10, 11, 12, 13, 14, or 15 contiguous nucleotides that are complementary to a contiguous stretch of nucleotides of the same length in the 5' overhang of the PAM-distal cleavage product. In some cases, the 5' overhang of the adapter nucleic acid comprises a stretch of from 5 contiguous nucleotides to 10 contiguous nucleotides that are complementary to a contiguous stretch of nucleotides of the same length in the 5' overhang of the PAM-distal cleavage product. In some cases, the 5' overhang of the adapter nucleic acid comprises a stretch of from 8 contiguous nucleotides to 10 contiguous nucleotides that are complementary to a contiguous stretch of nucleotides of the same length in the 5' overhang of the PAM-distal cleavage product. In some cases, the 5' overhang of the adapter nucleic acid has a length of from 8 nucleotides to 10 nucleotides; and comprises a stretch of from 8 contiguous nucleotides to 10 contiguous nucleotides that are complementary to a contiguous stretch of nucleotides of the same length in the 5' overhang of the PAM-distal cleavage product.

The total length of the adapter nucleic acid (including the 5' overhang) can be from about 10 nucleotides to 100 nucleotides. For example, the total length of the adapter nucleic acid (including the 5' overhang) can be from about 10 nucleotides (nt) to 15 nt, from 15 nt to 20 nt, from 20 nt to 25 nt, from 25 nt to 30 nt, from 30 nt to 40 nt, from 40 nt to 50 nt, from 50 nt to 60 nt, from 60 nt to 70 nt, from 70 nt to 80 nt, from 80 nt to 90 nt, or from 90 nt to 100 nt. In some cases, the total length of the adapter nucleic acid (including the 5' overhang) is from about 10 nt to about 25 nt. In some cases, the total length of the adapter nucleic acid (including the 5' overhang) is from about 15 nt to about 20 nt. In some cases, the total length of the adapter nucleic acid (including the 5' overhang) is from about 15 nt to about 25 nt. In some cases, the total length of the adapter nucleic acid (including the 5' overhang) is from about 15 nt to about 30 nt. In some cases, the total length of the adapter nucleic acid (including the 5' overhang) is from about 25 nt to about 30 nt. In some cases, the total length of the adapter nucleic acid (including the 5' overhang) is from about 20 nt to about 50 nt. In some cases, the total length of the adapter nucleic acid (including the 5' overhang) is from about 25 nt to about 50 nt.

In some cases, the adapter nucleic acid comprises, in addition to the 5' overhang discussed above, a 3' overhang. In some cases, the adapter nucleic acid comprises, in addition to the 5' overhang discussed above, a 3' adenosine overhang.

The adapter nucleic acid is ligated to the PAM-distal cleavage product, to generate a ligation product comprising the adapter and the PAM-distal cleavage product. In some cases, the ligation product is further ligated to one or more additional adapters, e.g., an adapter that provides a bar code, an adapter that allows for next-generation sequencing, and the like. For example, the one or more additional adapters can include a nucleotide sequence specific for coupling to a sequencing platform; such an adapter may also include a barcode sequence. In some cases, the additional adapter comprises a nucleotide sequence that is at least 70% identical to a support-bound oligonucleotide conjugated to a solid support; in some cases, the solid support is coupled to a sequencing platform. In some cases, the additional adapter comprises a binding site for a sequencing primer. Ligation of various adapters to a type V CRISPR/Cas effector polypeptide cleavage product is depicted schematically in FIG. 3.

Double-stranded adapters can comprise two separate oligonucleotides hybridized to one another (also referred to as an "oligonucleotide duplex"), and hybridization may leave one or more blunt ends, one or more 3' overhangs, one or more 5' overhangs, one or more bulges resulting from mismatched and/or unpaired nucleotides, or any combination of these. In some embodiments, a single-stranded adapter comprises two or mores sequences that are able to hybridize with one another. When two such hybridizable sequences are contained in a single-stranded adapter, hybridization yields a hairpin structure (hairpin adapter). When two hybridized regions of an adapter are separated from one another by a non-hybridized region, a "bubble" structure results. Adapters comprising a bubble structure can consist of a single adapter oligonucleotide comprising internal hybridizations, or may comprise two or more adapter oligonucleotides hybridized to one another. Internal sequence hybridization, such as between two hybridizable sequences in an adapter, can produce a double-stranded structure in a single-stranded adapter oligonucleotide. Adapters of different kinds can be used in combination, such as a hairpin adapter and a double-stranded adapter, or adapters of different sequences. Hybridizable sequences in a hairpin adapter may or may not include one or both ends of the oligonucleotide. When neither of the ends are included in the hybridizable sequences, both ends are "free" or "overhanging." When only one end is hybridizable to another sequence in the adapter, the other end forms an overhang, such as a 3' overhang or a 5' overhang. When both the 5'-terminal nucleotide and the 3'-terminal nucleotide are included in the hybridizable sequences, such that the 5'-terminal nucleotide and the 3'-terminal nucleotide are complementary and hybridize with one another, the end is referred to as "blunt."

Adapters can contain one or more of a variety of sequence elements, including but not limited to, one or more amplification primer annealing sequences or complements thereof, one or more sequencing primer annealing sequences or complements thereof, one or more barcode sequences, one or more common sequences shared among multiple different adapters or subsets of different adapters, one or more restriction enzyme recognition sites, one or more overhangs complementary to one or more target polynucleotide overhangs, one or more probe binding sites (e.g. for attachment to a sequencing platform, such as a flow cell for massive parallel sequencing, such as developed by Illumina, Inc.), one or more random or near-random sequences (e.g. one or more nucleotides selected at random from a set of two or more different nucleotides at one or more positions, with each of the different nucleotides selected at one or more positions represented in a pool of adapters comprising the random sequence), and combinations thereof. Two or more sequence elements can be non-adjacent to one another (e.g. separated by one or more nucleotides), adjacent to one another, partially overlapping, or completely overlapping. For example, an amplification primer annealing sequence can also serve as a sequencing primer annealing sequence. Sequence elements can be located at or near the 3' end, at or near the 5' end, or in the interior of the adapter oligonucleotide. When an adapter oligonucleotide is capable of forming secondary structure, such as a hairpin, sequence elements can be located partially or completely outside the secondary structure, partially or completely inside the secondary structure, or in between sequences participating in the secondary structure. For example, when an adapter oligonucleotide comprises a hairpin structure, sequence elements can be located partially or completely inside or outside the hybridizable sequences (the "stem"), including in the sequence between the hybridizable sequences (the "loop"). In some cases, the first adapter oligonucleotides in a plurality of first adapter oligonucleotides having different barcode sequences comprise a sequence element common among all first adapter oligonucleotides in the plurality. In some cases, all second adapter oligonucleotides comprise a sequence element common among all second adapter oligonucleotides that is different from the common sequence element shared by the first adapter oligonucleotides. A difference in sequence elements can be any such that least a portion of different adapters do not completely align, for example, due to changes in sequence length, deletion or insertion of one or more nucleotides, or a change in the nucleotide composition at one or more nucleotide positions (such as a base change or base modification). In some cases, an adapter oligonucleotide comprises a 5' overhang, a 3' overhang, or both that is complementary to one or more target polynucleotides. Complementary overhangs can be one or more nucleotides in length, including but not limited to 1, 2, 3, 4, 5, 6, 7, 8, 9, 10, 11, 12, 13, 14, 15, or more nucleotides in length. Complementary overhangs may comprise a fixed sequence. Complementary overhangs may comprise a random sequence of one or more nucleotides, such that one or more nucleotides are selected at random from a set of two or more different nucleotides at one or more positions, with each of the different nucleotides selected at one or more positions represented in a pool of adapters with complementary overhangs comprising the random sequence. In some cases, an adapter overhang is complementary to a target polynucleotide overhang produced by restriction endonuclease digestion. In some embodiments, an adapter overhang consists of an adenine or a thymine.

The terms "joining" and "ligation" as used herein, with respect to two polynucleotides, such as an adapter nucleic acid and a PAM-distal cleavage product, refers to the covalent attachment of two separate polynucleotides to produce a single larger polynucleotide with a contiguous backbone. Methods for joining two polynucleotides are known in the art, and include without limitation, enzymatic and non-enzymatic (e.g. chemical) methods. Examples of ligation reactions that are non-enzymatic include the non-enzymatic ligation techniques described in U.S. Pat. Nos. 5,780,613 and 5,476,930, which are herein incorporated by reference. In some cases, an adapter nucleic acid is joined to a target polynucleotide (e.g., a PAM-distal cleavage product) by a ligase, for example a DNA ligase or RNA ligase. Multiple ligases, each having characterized reaction conditions, are known in the art, and include, without limitation NAD+-dependent ligases including tRNA ligase, Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof.

Ligation can be between polynucleotides having hybridizable sequences, such as complementary overhangs. Ligation can also be between two blunt ends. Generally, a 5' phosphate is utilized in a ligation reaction. The 5' phosphate can be provided by the target polynucleotide, the adapter oligonucleotide, or both. 5' phosphates can be added to or removed from polynucleotides to be joined, as needed. Methods for the addition or removal of 5' phosphates are known in the art, and include without limitation enzymatic and chemical processes. Enzymes useful in the addition and/or removal of 5' phosphates include kinases, phosphatases, and polymerases. In some cases, both of the two ends joined in a ligation reaction (e.g. an adapter end and a target polynucleotide end) provide a 5' phosphate, such that two covalent linkages are made in joining the two ends. In some cases, only one of the two ends joined in a ligation reaction (e.g. only one of an adapter end and a target polynucleotide end) provides a 5' phosphate, such that only one covalent linkage is made in joining the two ends. In some cases, only one strand at one or both ends of a target polynucleotide is joined to an adapter nucleic acid. In some cases, both strands at one or both ends of a target polynucleotide (e.g., a PAM-distal cleavage product) are joined to an adapter nucleic acid. In some cases, 3' phosphates are removed prior to ligation. In some cases, an adapter nucleic acid is added to only one end of a target polynucleotide (e.g., a PAM-distal cleavage product). When both strands at both ends are joined to an adapter oligonucleotide, joining can be followed by a cleavage reaction that leaves a 5' overhang that can serve as a template for the extension of the corresponding 3' end, which 3' end may or may not include one or more nucleotides derived from the adapter oligonucleotide. In some cases, a target polynucleotide (e.g., a PAM-distal cleavage product) is joined to a first adapter nucleic acid on one end and a second adapter oligonucleotide on the other end. In some cases, two ends of a target polynucleotide are joined to the opposite ends of a single adapter oligonucleotide. In some cases, the target polynucleotide and the adapter nucleic acid to which it is joined comprise blunt ends. In some cases, separate ligation reactions are carried out for each sample, using a different first adapter nucleic acid comprising at least one barcode sequence for each sample, such that no barcode sequence is joined to the target polynucleotides of more than one sample. A target polynucleotide that has an adapter nucleic acid joined to it is considered "tagged" by the joined adapter.

In some cases, the primers are spiked primers, as described in Example 2. In some cases, a method of the present disclosure comprises use of metagenomic sequencing with spiked primer enrichment (MSSPE), as described in Example 2.

Amplification

As noted above, a sample comprising a target DNA can be subjected to one or more nucleic acid amplification steps before the contacting step. The sample can be subjected to one or more amplification steps prior to the contacting step, with primers that provide for amplification of nucleic acids of, e.g., specific pathogens, categories of pathogens, two or more different pathogens, or two or more different categories of pathogens.

Oligonucleotide Primers

A sample comprising a target DNA can be amplified using a method comprising contacting the sample with one or more pairs of nucleic acid primers. For example, in some cases, the sample is contacted with a single pair of nucleic acid primers (also referred to herein as "oligonucleotide primers" or, simply, "primers"). In some cases, the sample is contacted with two or more different pairs of primers; e.g., the sample is contacted with 2, 3, 4, 5, 6, 7, 8, 9, or 10, or more than 10 (e.g., from 10 to 15, from 15 to 20, from 20 to 25, or from 25 to 30), different pairs of primers. The term "different pairs of primers" refers to primer pairs that differ from one another in nucleotide sequence. For example, a first primer pair differs from a second primer pair in nucleotide sequence, where the first and second primer pairs are "different pairs of primers."

In some cases, the two or more different primer pairs provide for amplification of DNA from two or more different pathogens. In some cases, the two or more different primer pairs provide for amplification of DNA from two or more (e.g., 2, 3, 4, 5, 6, 7, 8, 9, 10, or more than 10 (e.g., from 10 to 15, from 15 to 20, from 20 to 25, or from 25 to 30)), different pathogens. In some cases, the two or more pathogens are viral pathogens. In some cases, the two or more pathogens are bacterial pathogens. In some cases, the two or more pathogens are helminths. In some cases, the two or more pathogens are protozoa. In some cases, the two or more pathogens are fungal pathogens.

In some case, the two or more different primer pairs provide for amplification of DNA from two or more categories of pathogens. For example, in some cases, the two or more different primer pairs provide for amplification of DNA from: two or more different hemorrhagic fever viruses. As another example, in some cases, the two or more different primer pairs provide for amplification of DNA of two or more different blood-borne pathogens. As another example, in some cases, the two or more different primer pairs provide for amplification of DNA of two or more different tick-borne pathogens. As another example, in some cases, the two or more different primer pairs provide for amplification of DNA of two or more different mosquito-borne pathogens. As another example, in some cases, the two or more different primer pairs provide for amplification of DNA of two or more antibiotic-resistant pathogens.

For example, forward and reverse primers that can be used in connection with detection of viral pathogens (i.e., that can be used to amplify a target nucleic acid of a viral pathogen) are set out in SEQ ID Nos:71 to 6432). The primers include primers suitable for amplifying Chikungunya virus (CHIKV), Dengue virus (DENV), Ebola virus, Hepatitis C virus (HCV), Hepatitis E virus (HEV), human immunodeficiency virus (HIV), Lassa virus, Marburg virus, measles virus, RVF, West Nile Virus (WNV), Yellow fever virus (YFV), and Zika virus (ZIKV). As another example, forward and reverse primers that can be used in connection with tick-borne diseases (i.e., that can be used to amplify a target nucleic acid of a tick-borne pathogen) are set out in SEQ ID Nos: 6433 to 13607. As yet another example, primers suitable for use in connection with detection of antibiotic resistance genes (e.g., nucleic acids that encode antibiotic resistance factors) are depicted in SEQ ID Nos: 13608 to 17378. Examples of target nucleic acids in the context of antibiotic resistance are depicted in FIG. 8. Any of the forward primers can be paired with any of the reverse primers set out in the aforementioned figures, as long as the target nucleotide sequence to which the forward primer hybridizes is 5' of the target nucleotide sequence to which the reverse primer hybridizes.

In some cases, the primers are spiked primers, as described in Example 2. In some cases, a method of the present disclosure comprises use of metagenomic sequencing with spiked primer enrichment (MSSPE), as described in Example 2.

Amplification Methods

Various amplification methods and components will be known to one of ordinary skill in the art and any convenient method can be used (see, e.g., Zanoli and Spoto, Biosensors (Basel). 2013 March, 3(1): 18-43; Gill and Ghaemi, Nucleosides, Nucleotides, and Nucleic Acids, 2008, 27: 224-243; Craw and Balachandrana, Lab Chip, 2012, 12, 2469-2486; which are herein incorporated by reference in their entirety). Nucleic acid amplification can comprise polymerase chain reaction (PCR), reverse transcription PCR (RT-PCR), quantitative PCR (qPCR), reverse transcription qPCR (RT-qPCR), nested PCR, multiplex PCR, asymmetric PCR, touchdown PCR, random primer PCR, hemi-nested PCR, polymerase cycling assembly (PCA), colony PCR, ligase chain reaction (LCR), digital PCR, methylation specific-PCR (MSP), co-amplification at lower denaturation temperature-PCR (COLD-PCR), allele-specific PCR, intersequence-specific PCR (ISS-PCR), whole genome amplification (WGA), inverse PCR, and thermal asymmetric interlaced PCR (TAIL-PCR).

In some cases, the amplification is isothermal amplification. The term "isothermal amplification" indicates a method of nucleic acid (e.g., DNA) amplification (e.g., using enzymatic chain reaction) that can use a single temperature incubation thereby obviating the need for a thermal cycler. Isothermal amplification is a form of nucleic acid amplification which does not rely on the thermal denaturation of the target nucleic acid during the amplification reaction and hence may not require multiple rapid changes in temperature. Isothermal nucleic acid amplification methods can therefore be carried out inside or outside of a laboratory environment. By combining with a reverse transcription step, these amplification methods can be used to isothermally amplify RNA.

Examples of isothermal amplification methods include, but are not limited to, loop-mediated isothermal Amplification (LAMP), helicase-dependent Amplification (HDA), recombinase polymerase amplification (RPA), strand displacement amplification (SDA), nucleic acid sequence-based amplification (NASBA), transcription mediated amplification (TMA), nicking enzyme amplification reaction (NEAR), rolling circle amplification (RCA), multiple displacement amplification (MDA), Ramification (RAM), circular helicase-dependent amplification (cHDA), single primer isothermal amplification (SPIA), signal mediated amplification of RNA technology (SMART), self-sustained sequence replication (3SR), genome exponential amplification reaction (GEAR) and isothermal multiple displacement amplification (IMDA).

In some cases, the amplification is recombinase polymerase amplification (RPA) (see, e.g., U.S. Pat. Nos. 8,030, 000; 8,426,134; 8,945,845; 9,309,502; and 9,663,820, which are hereby incorporated by reference in their entirety). Recombinase polymerase amplification (RPA) uses two opposing primers (much like PCR) and employs three enzymes—a recombinase, a single-stranded DNA-binding protein (SSB) and a strand-displacing polymerase. The recombinase pairs oligonucleotide primers with homologous sequence in duplex DNA, SSB binds to displaced strands of DNA to prevent the primers from being displaced, and the strand displacing polymerase begins DNA synthesis where the primer has bound to the target DNA. Adding a reverse transcriptase enzyme to an RPA reaction can facilitate detection RNA as well as DNA, without the need for a separate step to produce cDNA. One example of components for an RPA reaction is as follows (see, e.g., U.S. Pat. Nos. 8,030, 000; 8,426,134; 8,945,845; 9,309,502; 9,663,820): 50 mM Tris pH 8.4, 80 mM Potassium actetate, 10 mM Magnesium acetate, 2 mM DTT, 5% PEG compound (Carbowax-20M), 3 mM ATP, 30 mM Phosphocreatine, 100 ng/μl creatine kinase, 420 ng/μl gp32, 140 ng/μl UvsX, 35 ng/μl UvsY, 2000M dNTPs, 300 nM each oligonucleotide, 35 ng/μl Bsu polymerase, and a nucleic acid-containing sample).

In a transcription-mediated amplification (TMA) method, an RNA polymerase is used to make RNA from a promoter engineered in the primer region; then a reverse transcriptase synthesizes cDNA from the primer. A third enzyme, e.g., Rnase H, can then be used to degrade the RNA target from cDNA without the heat-denatured step. This amplification technique is similar to Self-Sustained Sequence Replication (3SR) and Nucleic Acid Sequence Based Amplification (NASBA), but varies in the enzymes employed. As another example, helicase-dependent amplification (HDA) utilizes a thermostable helicase (Tte-UvrD) rather than heat to unwind dsDNA to create single-strands that are then available for hybridization and extension of primers by polymerase. As yet another example, a loop-mediated amplification (LAMP) method employs a thermostable polymerase with strand displacement capabilities and a set of four or more specific designed primers. Each primer is designed to have hairpin ends that, once displaced, snap into a hairpin to facilitate self-priming and further polymerase extension. In a LAMP reaction, though the reaction proceeds under isothermal conditions, an initial heat denaturation step is required for double-stranded targets. In addition, amplification yields a ladder pattern of various length products. As yet another example, a strand displacement amplification (SDA) combines the ability of a restriction endonuclease to nick the unmodified strand of its target DNA and an exonuclease-deficient DNA polymerase to extend the 3' end at the nick and displace the downstream DNA strand.

Target RNA

In some cases, a target DNA present in a sample is generated from an RNA template. Any known method of generating DNA from an RNA template can be used. For example, a reverse transcriptase can be used to generate a target DNA from a target RNA.

Sequencing

As noted above, a subject method of characterizing a target DNA in a sample comprises ligating an adapter nucleic acid with a PAM-distal cleavage product, generating a ligation product comprising the adapter and the PAM-distal cleavage product. The PAM-distal cleavage product includes at least a portion of the target DNA. Thus, the ligation product includes at least a portion of the target DNA. The nucleotide sequence of the at least a portion of the target DNA present in the ligation product can be determined. The nucleotide sequence can be determined using any of a variety of methods for determining the nucleotide sequence of DNA.

In some cases, the nucleotide sequence is determined using next generation sequencing.

The term "next generation sequencing" (NGS) refers to the so-called highly parallelized methods of performing nucleic acid sequencing and comprises the sequencing-by-synthesis or sequencing-by-ligation platforms currently employed by Illumina, Life Technologies, Pacific Biosciences and Roche, etc. Next generation sequencing methods also include, but are not limited to, nanopore sequencing methods such as those offered by Oxford Nanopore, and electronic detection-based methods such as the Ion Torrent technology commercialized by Life Technologies.

As would be apparent to those skilled in the art, the ligation product may be amplified using primers that hybridize to the adapter present in the ligation product, thereby producing amplification products. In some cases, the primers used to amplify the fragments have a 5' tail that provides compatibility with a particular sequencing platform. In certain cases, one or more of the primers used in this step may additionally contain a sample identifier (e.g., a bar code). If the primers have a sample identifier, then products from different samples can be pooled prior to sequencing. In some cases, this amplifying step may comprise appending a sample identifier sequence to the amplified fragments.

As would be apparent to those skilled in the art, the adapters and/or the primers used for amplification may be compatible with use in a next generation sequencing platform, e.g., Illumina's reversible terminator method, Roche's pyrosequencing method (454), Life Technologies' sequencing by ligation (the SOLiD platform), Life Technologies' Ion Torrent platform or Oxford Nanopore's MinIon system. Examples of such methods are described in the following references: Margulies et al. (Nature 2005 437: 376-80); Ronaghi et al. (Analytical Biochemistry 1996 242: 84-9); Shendure (Science 2005 309: 1728); Imelfort et al. (Brief Bioinform. 2009 10:609-18); Fox et al. (Methods Mol Biol. 2009; 553:79-108); Appleby et al. (Methods Mol Biol. 2009; 513:19-39) and Morozova (Genomics. 2008 92:255-64), which are incorporated by reference for the general descriptions of the methods and the particular steps of the methods, including all starting products, reagents, and final products for each of the steps. The present method may be used on any sequencing platform, including those that are based on sequencing-by-synthesis (i.e., by extending a primer that is hybridized to a template).

The DNA sequencing technology can utilize the Ion Torrent sequencing platform, which pairs semiconductor technology with a sequencing chemistry to directly translate chemically encoded information (A, C, G, T) into digital information (0, 1) on a semiconductor chip. Without wishing to be bound by theory, when a nucleotide is incorporated into a strand of DNA by a polymerase, a hydrogen ion is released as a byproduct. The Ion Torrent platform detects the release of the hydrogen atom as a change in pH. A detected change in pH can be used to indicate nucleotide incorporation. The Ion Torrent platform comprises a high-density array of micro-machined wells to perform this biochemical process in a massively parallel way. Each well holds a different library member, which may be clonally amplified. Beneath the wells is an ion-sensitive layer and beneath that an ion sensor. The platform sequentially floods the array with one nucleotide after another. When a nucleotide, for example a C, is added to a DNA template and is then incorporated into a strand of DNA, a hydrogen ion will be released. The charge from that ion will change the pH of the solution, which can be identified by Ion Torrent's ion sensor. If the nucleotide is not incorporated, no voltage change will be recorded and no base will be called. If there are two identical bases on the DNA strand, the voltage will be double, and the chip will record two identical bases called. Direct identification allows recordation of nucleotide incorporation in seconds. Library preparation for the Ion Torrent platform generally involves ligation of two distinct adaptors at both ends of a DNA fragment.

The DNA sequencing technology can utilize an Illumina sequencing platform, which generally employs cluster amplification of library members onto a flow cell and a sequencing-by-synthesis approach. Cluster-amplified library members are subjected to repeated cycles of polymerase-directed single base extension. Single-base extension can involve incorporation of reversible-terminator dNTPs, each dNTP labeled with a different removable fluorophore. The reversible-terminator dNTPs are generally 3' modified to prevent further extension by the polymerase. After incorporation, the incorporated nucleotide can be identified by fluorescence imaging. Following fluorescence imaging, the fluorophore can be removed and the 3' modification can be removed resulting in a 3' hydroxyl group, thereby allowing another cycle of single base extension. Library preparation for the Illumina platform generally involves ligation of two distinct adaptors at both ends of a DNA fragment.

The DNA sequencing technology that is used can be the Helicos True Single Molecule Sequencing (tSMS), which can employ sequencing-by-synthesis technology. In the tSMS technique, a polyA adaptor can be ligated to the 3' end of DNA fragments. The adapted fragments can be hybridized to poly-T oligonucleotides immobilized on the tSMS flow cell. The library members can be immobilized onto the flow cell at a density of about $10^8$ templates/cm$^2$. The flow cell can be then loaded into an instrument, e.g., HeliScope™ sequencer, and a laser can illuminate the surface of the flow cell, revealing the position of each template. A CCD camera can map the position of the templates on the flow cell surface. The library members can be subjected to repeated cycles of polymerase-directed single base extension. The sequencing reaction begins by introducing a DNA polymerase and a fluorescently labeled nucleotide. The polymerase can incorporate the labeled nucleotides to the primer in a template directed manner. The polymerase and unincorporated nucleotides can be removed. The templates that have directed incorporation of the fluorescently labeled nucleotide can be discerned by imaging the flow cell surface.

After imaging, a cleavage step can remove the fluorescent label, and the process can be repeated with other fluorescently labeled nucleotides until a desired read length is achieved. Sequence information can be collected with each nucleotide addition step.

The DNA sequencing technology can utilize a SOLiD™ technology (Applied Biosystems). The SOLiD platform generally utilizes a sequencing-by-ligation approach. Library preparation for use with a SOLiD platform generally comprises ligation of adapters to the 5' and 3' ends of the DNA fragments (e.g., ligation products) to be sequenced to generate a fragment library. Alternatively, internal adapters can be introduced by ligating adapters to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations can be prepared in microreactors containing beads, primers, template, and PCR components. Following PCR, the templates can be denatured. Beads can be enriched for beads with extended templates. Templates on the selected beads can be subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide can be removed and the process can then be repeated.

The DNA sequencing technology can utilize a single molecule, real-time (SMRT™) sequencing platform (Pacific Biosciences). In SMRT sequencing, the continuous incorporation of dye-labeled nucleotides can be imaged during DNA synthesis. Single DNA polymerase molecules can be attached to the bottom surface of individual zero-mode wavelength identifiers (ZMW identifiers) that obtain sequence information while phospholinked nucleotides are being incorporated into the growing primer strand. A ZMW generally refers to a confinement structure which enables observation of incorporation of a single nucleotide by DNA polymerase against a background of fluorescent nucleotides that rapidly diffuse in an out of the ZMW on a microsecond scale. By contrast, incorporation of a nucleotide generally occurs on a milliseconds timescale. During this time, the fluorescent label can be excited to produce a fluorescent signal, which is detected. Detection of the fluorescent signal can be used to generate sequence information. The fluorophore can then be removed, and the process repeated. Library preparation for the SMRT platform generally involves ligation of hairpin adaptors to the ends of DNA fragments.

The DNA sequencing technology can utilize nanopore sequencing (e.g. as described in Soni G V and Meller A. Clin Chem 53: 1996-2001 (2007)). Nanopore sequencing DNA analysis techniques are being industrially developed by a number of companies, including Oxford Nanopore Technologies (Oxford, United Kingdom). Nanopore sequencing is a single-molecule sequencing technology whereby a single molecule of DNA is sequenced directly as it passes through a nanopore. A nanopore can be a small hole, of the order of 1 nanometer in diameter. Immersion of a nanopore in a conducting fluid and application of a potential (voltage) across can result in a slight electrical current due to conduction of ions through the nanopore. The amount of current which flows is sensitive to the size and shape of the nanopore and to occlusion by, e.g., a DNA molecule. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence.

The DNA sequencing technology can utilize a chemical-sensitive field effect transistor (chemFET) array (e.g., as described in U.S. Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the Y end of the sequencing primer can be discerned by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Target Nucleic Acids

A target nucleic acid can be single stranded (ssDNA), a double stranded (dsDNA), or an RNA.

Where the target DNA is a ssDNA, the ssDNA can be used as a template for second strand synthesis, to generate a dsDNA. Where the target nucleic acid is an RNA, the RNA can be used as a template for reverse transcriptase, to generate a complementary DNA (cDNA); and the cDNA can be used as a template for second strand synthesis, to generate a dsDNA.

When the target DNA is single stranded, there is no preference or requirement for a PAM sequence in the target DNA. However, when the target DNA is dsDNA, a PAM is usually present adjacent to the target sequence of the target DNA (e.g., see discussion of the PAM elsewhere herein). The source of the target DNA can be the same as the source of the sample, e.g., as described below.

The source of the target nucleic acid can be from any source. In some cases, the target DNA is DNA of a pathogen. In some cases, the target nucleic acid is not from a pathogenic organism. In some cases, the target DNA is from a mammal. In some cases, the target nucleic acid is from a plant.

In some cases, the target nucleic acid is DNA or RNA of a pathogen (e.g., a pathogen that infects a human; a pathogen that infects a non-human mammal; a pathogen that infects a bird; a pathogen that infects a reptile; a pathogen that infects an amphibian; a pathogen that infects a fish; a pathogen that infects a plant; etc.).

In some cases, the target nucleic acid is a not from a pathogenic organism. For example, in some cases, the target nucleic acid is fetal DNA from a human.

In some cases, the target DNA is a viral DNA (e.g., a genomic DNA of a DNA virus). In some cases, the target DNA is bacterial DNA. In some cases, the target DNA is DNA of a protozoan. In some cases, the target DNA is DNA of a helminth. In some cases, the target DNA is DNA of a fungus.

The target nucleic acid can be from a bacterium, such as *Bacillus* (e.g., *B. anthracis*), Enterobacteriaceae (e.g., *Salmonella, Escherichia coli, Yersinia pestis, Klebsiella*, and *Shigella*), *Yersinia* (e.g., *Y. pestis* or *Y. enterocolitica*), *Staphylococcus* (e.g., *S. aureus*), *Streptococcus, Gonorrheae, Enterococcus* (e.g., *E. faecalis*), *Listeria* (e.g., *L. monocytogenes*), *Brucella* (e.g., *B. abortus, B. melitensis*, or *B. suis*), *Vibrio* (e.g., *V. cholerae*), *Corynebacterium diphtheria, Pseudomonas* (e.g., *P. pseudomallei* or *P. aerugi-*

*nosa*), *Burkholderia* (e.g., *B. mallei* or *B. pseudomallei*), *Shigella* (e.g., *S. dysenteriae*), *Rickettsia* (e.g., *R. rickettsii, R. prowazekii*, or *R. typhi*), *Francisella tularensis, Chlamydia psittaci, Coxiella burnetii, Mycoplasma* (e.g., *M. mycoides*), etc.

The target nucleic acid can be from a virus, such as Adenoviridae (e.g., adenovirus), Arenaviridae (e.g., Machupo virus), Bunyaviridae (e.g., Hantavirus or Rift Valley fever virus), Coronaviridae, Orthomyxoviridae (e.g., influenza viruses), Filoviridae (e.g., Ebola virus and Marburg virus), Flaviviridae (e.g., Japanese encephalitis virus and Yellow fever virus), Hepadnaviridae (e.g., hepatitis B virus), Herpesviridae (e.g., herpes simplex viruses), Papovaviridae (e.g., papilloma viruses), Paramyxoviridae (e.g., respiratory syncytial virus, measles virus, mumps virus, or parainfluenza virus), Parvoviridae, Picornaviridae (e.g., polioviruses), Poxviridae (e.g., variola viruses), Reoviridae (e.g., rotaviruses), Retroviridae (e.g., human T cell lymphotropic viruses (HTLV) and human immunodeficiency viruses (HIV)), Rhabdoviridae (e.g., rabies virus), and Togaviridae (e.g., encephalitis viruses, yellow fever virus, and rubella virus)). Where the virus is a ssDNA virus, the ssDNA can be used as a template for second strand synthesis, to generate a dsDNA. Where the virus is an RNA virus, the RNA can be used as a template for reverse transcriptase, to generate a complementary DNA (cDNA); and the cDNA can be used as a template for second strand synthesis, to generate a dsDNA.

The target nucleic acid can be from a protozoon, such as *Cryptosporidium parvum*, Encephalitozoa, *Plasmodium* (e.g., *Plasmodium falciparum*), *Toxoplasma gondii, Acanthamoeba, Entamoeba histolytica, Giardia lamblia, Trichomonas vaginalis, Leishmania*, or *Trypanosoma* (e.g., *T. brucei; T. cruzi*); etc.

The target nucleic acid can be from a helminth, such as cestodes (tapeworms), trematodes (flukes), or nematodes (roundworms, e.g., *Ascaris lumbricoides, Trichuris trichiura, Necator americanus*, or *Ancylostoma duodenale*); etc.

The target nucleic acid can be from a fungus, such as Aspergilli, Candidae, *Coccidioides immitis*, and Cryptococci.

Examples of possible target nucleic acids include, but are not limited to, viral nucleic acids such as: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), Epstein-Barr virus (EBV), cytomegalovirus (CMV), herpes lymphotropic virus, *Pityriasis Rosea*, kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 GI); Geminiviridae; Nanoviridae; Phycodnaviridae; Zika virus; and the like.

In some cases, the target nucleic acid is from a viral pathogen selected from among Adenoviruses, Alphaviruses (Togaviruses), Eastern equine encephalitis virus, Eastern equine encephalomyelitis virus, Venezuelan equine encephalomyelitis vaccine strain TC-83, Western equine encephalomyelitis virus, Arenaviruses, Lymphocytic choriomeningitis virus (non-neurotropic strains), Tacaribe virus complex, Bunyaviruses, Bunyamwera virus, Rift Valley fever virus vaccine strain MP-12, Calciviruses, Coronaviruses. Flaviviruses (Togaviruses)-Group B Arboviruses, Dengue virus serotypes 1, 2, 3, and 4, Yellow fever virus vaccine strain 17D, Hepatitis A, B, C, D, and E viruses, the Cytomegalovirus, Epstein Barr virus, Herpes simplex types 1 and 2, Herpes zoster, Human herpesvirus types 6 and 7, Influenza viruses types A, B, and C, Papovaviruses, Papilloma viruses, Newcastle disease virus, Measles virus, Mumps virus, Parainfluenza viruses types 1, 2, 3, and 4, polyomaviruses (JC virus, BK virus), Respiratory syncytial virus, Human parvovirus (B 19), Coxsackie viruses types A and B, Echoviruses, Polioviruses, Rhinoviruses, Alastrim (*Variola minor* virus), Smallpox (*Variola major* virus), Whitepox Reoviruses, Coltivirus, human Rotavirus, and Orbivirus (Colorado tick fever virus), Rabies virus, Vesicular stomatitis virus, Rubivirus (rubella), Semliki Forest virus, St. Louis encephalitis virus, Venezuelan equine encephalitis virus, Venezuelan equine encephalomyelitis virus, Arenaviruses (a.k.a. South American Hemorrhagic Fever virus), Flexal, Lymphocytic choriomeningitis virus (LCM) (neurotropic strains), Hantaviruses including Hantaan virus, Rift Valley fever virus, Japanese encephalitis virus, Yellow fever virus, Monkeypox virus, Human immunodeficiency virus (HIV) types 1 and 2, Human T cell lymphotropic virus (HTLV) types 1 and 2, Simian immunodeficiency virus (SIV), Vesicular stomatitis virus, Guanarito virus, Lassa fever virus, Junin virus, Machupo virus, Sabia, Crimean-Congo hemorrhagic fever virus, Ebola viruses, Marburg virus, Tick-borne encephalitis virus complex (flavi) including Central European tick-borne encephalitis, Far Eastern tick-borne encephalitis, Hanzalova, Hypr, Kumlinge, Kyasanur Forest disease, Omsk hemorrhagic fever, and Russian Spring Summer encephalitis viruses, Herpesvirus simiae (Herpes B or Monkey B virus), Cercopithecine herpesvirus 1 (Herpes B virus), Equine morbillivirus (Hendra and Hendra-like viruses), Nipah virus, *Variola major* virus (Smallpox virus), *Variola minor* virus (Alastrim), African swine fever virus, African horse sickness virus, Akabane virus, Avian influenza virus (highly pathogenic), Blue tongue virus, Camel pox virus, Classical swine fever virus, *Cowdria ruminantium* (heartwater), Foot and mouth disease virus, Goat pox virus, Japanese encephalitis virus, Lumpy skin disease virus, Malignant catarrhal fever virus, Menangle virus, Newcastle disease virus (VVND), Peste Des Petits Ruminants virus, Rinderpest virus, Sheep pox virus, Swine vesicular disease virus, and Vesicular stomatitis virus (exotic).

In some cases, the target nucleic acid is bacterial DNA, e.g., DNA of a pathogenic bacterium. In some embodiments, the bacterial pathogen is selected from among *Acinetobacter baumannii* (formerly *Acinetobacter calcoaceticus*); *Actinobacillus; Actinomyces pyogenes* (formerly *Corynebacterium pyogenes*); *Actinomyces israelii; Nocardia asteroides; N. brasiliensis; Aeromonas hydrophila; Amycolata autotrophica; Archanobacterium haemolyticum* (formerly *Corynebacterium haemolyticum*); *Arizona hinshawii*—all serotypes; *Bacillus anthracis; Bacteroides fragilis; Bartonella henselae; B. quintana; B. vinsonii; Bordetella* including *B. pertussis; Borrelia recurrentis; B. burgdorferi; Burkholderia* (formerly *Pseudomonas* species), *Campylobacter coli, C. fetus, C. jejuni, Chlamydia psittaci, C. trachomatis, C. pneumonia, Clostridium botulinum* (neurotoxin producing species), *Cl. chauvoei, Cl. haemolyticum, Cl. histolyticum, Cl. novyi, Cl. septicum, Cl. tetani, Cl. perfringens, Corynebacterium diphtheriae, C. pseudotuberculosis, C. renale, Dermatophilus congolensis, Edwardsiella tarda, Erysipelothrix rhusiopathiae, Escherichia coli*—all enteropathogenic, enterotoxigenic, enteroinvasive and strains bearing K1 antigen, including *E. coli* O157:H7; *Haemophilus ducreyi, H. influenzae; Helicobacter pylori, Klebsiella*—all species; *Legionella* including *L. pneumophila; Leptospira interrogans*—all serotypes; *Listeria, Moraxella, Mycobacterium*, including *M. avium* complex, *M. asiaticum, M. bovis* BCG vaccine strain, *M. chelonei, M. fortuitum, M. kansasii, M. leprae, M. malmoense, M. marinum, M. paratuberculosis, M. scrofulaceum, M. simiae, M. szulgai, M. ulcerans, M. xenopi; Mycoplasma; Neisseria gonorrhoeae, N. meningitides, Nocardia asteroides, N. brasiliensis, N. otitidiscaviarum, N. transvalensis; Proteus mirabilis; P. vulgaris; Rhodococcus equi; Salmonella* including *S. arizonae, S. cholerasuis, S. enteritidis, S. gallinarum-pullorum, S. meleagridis, S. paratyphi*, A, B, C, *S. typhi; S. typhimurium; Shigella* including *S. boydii, S. dysenteriae*, type 1, *S. flexneri, S. sonnei; Sphaerophorus necrophorus; Staphylococcus aureus; Streptobacillus moniliformis; Streptococcus* including *S. pneumoniae, S. pyogenes; Treponema pallidum, T. carateum; Vibrio cholerae, V. parahemolyticus, V. vulnificus; Yersinia enterocolitica; Bartonella; Brucella* including *B. abortus, B. canis, B. suis, B. melitensis; Burkholderia (Pseudomonas) mallei; B. pseudomallei; Coxiella burnetiid; Francisella tularensis; Mycobacterium bovis, M. tuberculosis*, Mycobacteria; *Pasteurella multocida* type B—"buffalo" and other virulent strains; *Rickettsia akari, R. australis, R. canada, R. conorii, R. prowazekii, R. rickettsii, R. siberica, R. tsutsugamushi, R. typhi (R. moosert)*; and *Yersinia pestis*.

In some cases, the target nucleic acid is a nucleic acid of a parasite, e.g., a parasite selected from among *Ancylostoma* human hookworms including *A. duodenale, A. ceylanicum; Ascaris* including *Ascaris lumbricoides suum; Babesia* including *B. divergens, B. microti; Brugia filaria* worms including *B. malayi, B. timori*; Coccidia; *Cryptosporidium* including *C. parvum; Cysticercus cellulosae* (hydatid cyst, larva of *T. solium); Echinococcus* including *E. granulosis, E. multilocularis, E. vogeli; Entamoeba histolytica; Enterobius; Fasciola* including *F. gigantica, F. hepatica, Giardia* including *G. lamblia; Heterophyes; Hymenolepis* including *H. diminuta, H. nana; Isospora; Leishmania* including *L. braziliensis, L. donovani, L. ethiopia, L. major, L. mexicana, L. peruvania, L. tropica; Loa loa filaria* worms, *Microsporidium; Naegleria fowleri*; Necator human hookworms including *N. americanus, Onchocerca filaria* worms including, *O. volvulus; Plasmodium cynomologi, P. falciparum, P. malariae, P. ovale, P. vivax; Sarcocystis* including *S. sui hominis; Schistosoma* including *S. haematobium, S. intercalatum, S. japonicum, S. mansoni, S. mekongi; Strongyloides* including *S. stercoralis; Taenia solium; Toxocara* including *T. canis; Toxoplasma* including *T. gondii; Trichinella spiralis; Trypanosoma* including *T. brucei brucei, T. brucei gambiense, T. brucei rhodesiense, T. cruzi*; and *Wuchereria bancrofti filaria* worms.

In some cases, the target nucleic acid is nucleic acid of a fungus, e.g., from a fungal pathogen selected from among *Aspergillus fumigates, Blastomyces dermatitidis, Cladosporium bantianum, Candida albicans, C. (Xylohypha) trichoides, Cryptococcus neoformans, Dactylaria galopava (Ochroconis gallopavum), Epidermophyton, Exophiala (Wangiella) dermatitidis, Fonsecaea pedrosoi, Microsporum, Paracoccidioides braziliensis, Penicillium marnefei, Pneumocystis carinii, Sporothrix schenckii, Trichophyton, Coccidioides immitis, Coccidioides posadasii, Histoplasma capsulatum*, and *H. capsulatum* var. *duboisii*.

In some cases, the drug resistant pathogen is selected from the group consisting of vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus.

Target nucleic acids can include, e.g., 16S ribosomal RNA (rRNA), e.g., where the target nucleic acid is a nucleic acid of a bacterium (e.g., *Anaplasma, Bartonella, Borrelia burgdoferi, Borrelia miyamotoi, Brucella, Chlamydophila, Coxiella, Francisella, Rickettsia*, etc.). Target nucleic acids can encompass the entire genome (e.g., where the target nucleic acid is a nucleic acid of a viral pathogen).

Target nucleic acids also include any nucleic acid from a bacterium, fungus, or parasite that is used for identification and genotyping.

In some cases, the target nucleic acid is a particular segment or coding region of a nucleic acid. For example, for certain viruses, a nucleic acid encoding a structural polyprotein can be the target nucleic acid. As another example, for certain viruses, an L segment nucleic acid can be the target nucleic acid. As another example, for certain viruses, a nucleic acid encoding an NS5 polypeptide can be the target nucleic acid.

For example, for Colorado tick fever virus, segment 1 can be the target nucleic acid. As another example, for Epstein-Barr Virus, a nucleic acid encoding nuclear protein can be the target nucleic acid. As another example, for Eastern Equine Encephalitis Virus, a nucleic acid encoding a structural polyprotein can be the target nucleic acid. As another example, for Hanta virus, Heartland virus, La Crosse Virus, Lymphocytic Choriomeningitis Virus, Sin Nombre Virus, an L segment nucleic acid can be the target nucleic acid.

In some cases, e.g., where the target nucleic acid is a nucleic acid of a fungus (e.g., *Apophysomyces, Aspergillus, Blastomyces, Candida, Coccidiodes, Cryptococcus, Cunninghamela, Fusarium, Histoplasma, Lichteimia, Murcor, Rhizopus*, and the like), an internal transcribed spacer 1 (ITS1) gene can be the target nucleic acid.

In some cases, e.g., where the target nucleic acid is a nucleic acid of a parasite (e.g., *Acanthamoeba, Angiostrongylus, Ascaris, Babesia, Balamuthia, Blastocytis, Brugia, Cyclospora, Echinococcus, Entamoeba, Fasciola, Giardia, Leishmania, Loa loa, Naegleria, Schistosoma, Strongyloides, Taenia, Toxoplasma, Trichinella, Trypanosoma, Plasmodium*, and the like), a target nucleic acid can be an 18S rRNA.

In some cases, e.g., where the target nucleic acid is an antibiotic resistance gene, the target nucleic acid can be a gene involved in one or more of: i) aminoglycoside resistance (e.g., an aac (acetylase) gene; an aph (phosphorylation) gene; an ant (adenylation gene); ii) beta-lactam resistance, e.g., where the gene is a beta-lactamase gene, such as beta-lactamase class A, beta-lactamase class B, beta-lactamase class C, or beta-lactamase class D); iii) macrolide-lincosamide-streptogramin B ($MLS_B$) resistance (e.g., an erm rRNA methylase; an APT-binding transporter, a major facilitator family transporter, an esterase, a hydrolase, a transferase, or a phosphorylase); iv) a multidrug transporter (e.g., a major facilitator superfamily (MFS) transporter, an ATP-binding cassette transporter, an resistance-nodulation-cell divisional (RND) transporter, or a small multidrug resistance (SMR) transporter, v) tetracycline resistance (e.g., tetracycline efflux resistance or ribosome protection resistance); and vi) vancomycin resistance (e.g., VanA type operon, VanB type operon, VanC type operon, VanD type operon, VanE type operon, or VanG type operon).

In some cases, e.g., where the target nucleic acid is an antibiotic resistance gene, the target nucleic acid can be a gene involved aminoglycoside resistance. In some cases, e.g., where the target nucleic acid is an antibiotic resistance gene, the target nucleic acid can be an acetyltransferase gene (e.g., aac2I, aac2Ia, aac2Ib, etc.). In some cases, e.g., where the target nucleic acid is an antibiotic resistance gene, the target nucleic acid can be a nucleotidyltransferase (adenylyltransferase) (e.g., aadD ant2Ia, ant2Ib, ant3Ia, aad9, aad9Ib, etc.). In some cases, e.g., where the target nucleic acid is an antibiotic resistance gene, the target nucleic acid can be a phosphotransferase (e.g., aph33Ia, aph33Ib, aph3IIIa, aph3Iva, etc.).

In some cases, e.g., where the target nucleic acid is an antibiotic resistance gene, the target nucleic acid can be a gene involved in beta-lactam resistance. For example, the target nucleic acid is in some instances a beta-lactamase class A gene (e.g., BL2a_1, BL2a_III, BL2_len, BL2b_rob, BL2c_bro, BL2_kpc, etc. As another example, the target nucleic acid is in some instances a beta-lactamase class B gene (e.g., BL3_ccra, BL3_imp, BL3_sim, BL3_cit, BL3_vim, etc.). As another example, the target nucleic acid is in some instances a beta-lactamase class C gene (e.g., BL1_ampc, BL1-asba, BL1_cmy2, BL1_ec, BL1_pao, etc. As another example, the target nucleic acid is in some instances a beta-lactamase class D gene (e.g., BL2d_lcr1, BL2d_moxa, BL2d_oxa1, BL2d_r39, etc.).

In some cases, e.g., where the target nucleic acid is an antibiotic resistance gene, the target nucleic acid can be a gene involved in macrolide-lincosamide-streptogramin B ($MLS_B$) resistance. For example, the target nucleic acid is in some instances an erm class rRNA methylase (e.g., ermA, ermB, ermC, ermD, ermE, ermF, ermG, ermH, ermN, ermO, ermQ, ermS, ermT, etc.). As another example, the target nucleic acid is in some instances an ATP transporter gene (e.g., CarA, MsrA, OleB, SrmB, TlrC, VgaA, or VgaB). As another example, the target nucleic acid is in some instances a major facilitator superfamily transporter gene (e.g., LmrA, LmrB, or MefA). As another example, the target nucleic acid is in some instances an esterase gene (e.g., EreA or EreB). As another example, the target nucleic acid is in some instances a hydrolase gene (e.g., VgbA or VgbB). As another example, the target nucleic acid is in some instances a transferase gene (e.g., LnuA, LnuB, VatA, VatB, VatC, VatD, or VatE. As another example, the target nucleic acid is in some instances a phosphorylase gene (e.g., MphA, MphB, or MphC).

In some cases, e.g., where the target nucleic acid is an antibiotic resistance gene, the target nucleic acid can be a multidrug transporter gene. For example, the target nucleic acid is in some instances an ABC transporter gene (e.g., lsa). As another example, the target nucleic acid is in some instances a major facilitator superfamily transporter gene (e.g., Bmr, EmeA, EmrD, PmrA, RosA, cm1_e1, cm1_e2, etc.). As another example, the target nucleic acid is in some instances an RND transporter gene (e.g., AcrA, AcrB, AdeA, AdeB, AmrA, AmrB, CeoA, SmeA, SmeB, MexA, MexB, TolC, AdeC, OprA, OprM, etc.). As another example, the target nucleic acid is in some instances an SMR transporter gene (e.g., EmrE or Qac).

In some cases, e.g., where the target nucleic acid is an antibiotic resistance gene, the target nucleic acid can be a gene involved in tetracycline resistance. For example, the target nucleic acid is in some instances a tetracycline efflux protein gene (e.g., otrB, tcr3, tet30, tet31, tet33, tet39, tetA, tetB, tetC, tetD, tetE, tetG, tetH, tetJ, tetK, tetL, tetPA, tetV, tetY, tetZ, etc.). As another example, the target nucleic acid is in some instances a ribosomal protection protein against tetracycline gene (e.g., otrA, tet, tet32, tet36, tetM, tetO, tetPB, tetQ, tetS, tetT, or tetW).

In some cases, e.g., where the target nucleic acid is an antibiotic resistance gene, the target nucleic acid can be a gene involved in vancomycin resistance. For example, the target nucleic acid is in some instances a VanA operon gene (e.g., VanA, VanHA, VanRA, etc.). As another example, the target nucleic acid is in some instances a VanB operon gene (e.g., VanB, VanHB, VanRB, VanSB, etc.). As another example, the target nucleic acid is in some instances a VanC operon gene (e.g., VanC, VanRC, VanSC, VanT, or VanXYC). As another example, the target nucleic acid is in some instances a VanD operon gene (e.g., VanD, VanHD, VanRD, VanSD, VanXD, or VanYD). As another example, the target nucleic acid is in some instances a VanE operon gene (e.g., VanE, VanRE, VanSE, VanTE, or VanXYE). As another example, the target nucleic acid is in some instances a VanG operon gene (e.g., VanG, VanRG, VanSG, VanTG, VanUG, VanWG, VanXYG, or VanYG).

In some cases, e.g., where the target nucleic acid is an antibiotic resistance gene, the target nucleic acid can be a gene listed in FIG. 8. Non-limiting examples of such antibiotic resistance genes include $bla_{tem}$, $bla_{shv}$, $bla_{rob}$, $bla_{oxa}$, blaZ, aadB, aacC1, aacC2, aacC3, aac6'-IIa, aacA4, aad(6'), vanA, vanB, vanC, msrA, sarA, aac(6') aph(2''), vat, vga, ermA, ermB, ermC, int, sul, aac2ia, aac2ib, aac2ic, aac2id, aac2i, aac3ia, aac3iia, aac3iib, aac3iii, aac3iv, aac3ix, aac3vi, aac3viii, aac3vii, aac3x, aac6i, aac6ia, aac6ib, aac6ic, aac6ie, aac6if, aac6ig, aac6iia, aac6iib, aad9, aad9ib, aadd, acra, acrb, adea, adeb, adec, amra, amrb, ant2ia, ant2ib, ant3ia, ant4iia, ant6ia, aph33ia, aph33ib, aph3ia, aph3ib, aph3ic, aph3iiia, aph3iva, aph3va, aph3vb, aph3via, aph3viia, aph4ib, aph6ia, aph6ib, aph6ic, aph6id, arna, baca, bcra, bcrc, bl1_acc, bl1_ampc, bl1_asba, bl1_ceps, bl1_cmy2, bl1_ec, bl1_fox, bl1_mox, bl1_och, bl1_jao, bl1_pse, bl1_sm, bl2a_1, bl2a_exo, bl2a_iii2, bl2a_iii, bl2a_kcc, bl2a_nps, bl2a_okp, bl2a_jc, bl2be_ctxm, bl2be_oxy1, bl2be_per, bl2be_shv2, bl2b_rob, bl2b_tem, bl2b_tem2, bl2b_tem, bl2b_tle, bl2b_ula, bl2c_bro, bl2c_pse1, bl2c_pse3, bl2d_lcr1, bl2d_moxa, bl2d_oxa10, bl2d_oxa1, bl2d_oxa2, bl2d_oxa5, bl2d_oxa9, bl2d_r39, bl2e_cbla, bl2e_cepa, bl2e_cfxa, bl2e_fpm, bl2e_y56, bl2f_nmca, bl2f_smel, bl2_ges, bl2_kpc, bl2_len, bl2_veb, bl3_ccra, bl3_cit, bl3_cpha, bl3_gim, bl3_imp, bl3_1, bl3_shw, bl3_sim, bl3_vim, ble, blt, bmr, cara, cata10, cata11, cata12, cata13, cata14, cata15, cata16, cata1, cata2, cata3, cata4, cata5, cata6, cata7, cata8, cata9, catb 1, catb2, catb3, catb4, catb5, ceoa, ceob, cml_e1, cml_e2, cml_e3, cml_e4, cml_e5, cml_e6, cml_e7, cml_e8, dfra10, dfra12, dfra13, dfra14, dfra15, dfra16, dfra17, dfra19, dfra1, dfra20, dfra21, dfra22, dfra23, dfra24, dfra25, dfra25, dfra25, dfra26, dfra5, dfra7, dfrb1, dfrb2, dfrb3, dfrb6, emea, emrd, emre, erea, ereb, erma, ermb, ermc, ermd, erme, ermf, ermg, ermh, ermn, ermo, ermq, ermr, erms, ermt, ermu, ermv, ermw, ermx, ermy, fosa, fosb, fosc, fosx, fusb, fush, ksga, lmra, lmrb, lnua, inub, isa, maca, macb, mdte, mdtf, mdtg, mdth, mdtk, mdtl, mdtm, mdtn, mdto, mdtp, meca, mecrl, mefa, mepa, mexa, mexb, mexc, mexd, mexe, mexf, mexh, mexi, mexw, mexx, mexy, mfpa, mpha, mphb, mphc, msra, norm, oleb, opcm, opra, oprd, oprj, oprm, oprn, otra, otrb, pbp1a, pbp1b, pbp2b, pbp2, pbp2x, pmra, qac, qaca, qacb, qnra, qnrb, qnrs, rosa, rosb, smea, smeb, smec, smed, smee, smef, srmb, sta, str, sul1, sul2, sul3, tcma, tcr3, tet30, tet31, tet32, tet33, tet34, tet36, tet37, tet38, tet39, tet40, teta, tetb, tetc, tetd, tete, tetg, teth, tetj, tetk, tetd, tetm, teto, tetpa, tetpb, tet, tetq, tets, tett, tetu, tetv, tetw, text, tety, tetz, tlrc, tmrb, tolc, tsnr, vana, vanb, vanc, vand, vane, yang, vanha, vanhb, vanhd, vanra, vanrb, vanrc, vanrd, vanre, vanrg, vansa, vansb, vansc, vansd, vanse, vansg, vant, vante, vantg, vanug, vanwb, vanwg, vanxa, vanxb, vanxd, vanxyc, vanxye, vanxyg, vanya, vanyb, vanyd, vanyg, vanz, vata, vatb, vatc, vatd, vate, vgaa, vgab, vgba, vgbb, vph, ykkc, and ykkd (see the Antibiotic Resistance Genes Database (ARDB) available online). For example, in some cases, the target nucleic acid can be, e.g., mecA (e.g., as found in methicillin-resistant *Staphylococcus aureus* (MRSA)).

Samples

A sample includes a nucleic acid. As noted above, nucleic acids include: i) dsDNAs; ii) ssDNA, where a dsDNA can be prepared from a ssDNA, e.g., by second strand synthesis using the ssDNA as a template; and iii) RNA, where a dsDNA can be prepared from an RNA, e.g., by reverse transcription using the RNA as a template to generate a cDNA, and second strand synthesis using the cDNA as a template. For simplicity, the discussion below refers to "DNA" or "DNAs"; however, the nucleic acid being detected can be a dsDNA that is prepared from a ssDNA (such as a ssDNA virus) or from an RNA (such as an RNA virus).

A subject sample includes nucleic acid (e.g., a plurality of nucleic acids). The term "plurality" is used herein to mean two or more. In some cases, a sample includes two or more (e.g., 3 or more, 5 or more, 10 or more, 20 or more, 50 or more, 100 or more, 500 or more, 1,000 or more, or 5,000 or more) nucleic acids (e.g., dsDNAs; or in the case of a ssDNA, a dsDNA prepared from a ssDNA, e.g., by second strand synthesis using the ssDNA as a template; or in the case of an RNA, a dsDNA prepared from an RNA, e.g., by reverse transcription using the RNA as a template to generate a cDNA, and second strand synthesis using the cDNA as a template). In some cases, the sample includes 5 or more DNAs (e.g., 10 or more, 20 or more, 50 or more, 100 or more, 500 or more, 1,000 or more, or 5,000 or more DNAs) that differ from one another in sequence. In some cases, the sample includes 10 or more, 20 or more, 50 or more, 100 or more, 500 or more, $10^3$ or more, $5 \times 10^3$ or more, $10^4$ or more, $5 \times 10^4$ or more, $10^5$ or more, $5 \times 10^5$ or more, $10^6$ or more $5 \times 10^6$ or more, or $10^7$ or more, DNAs. In some cases, the sample comprises from 10 to 20, from 20 to 50, from 50 to 100, from 100 to 500, from 500 to $10^3$, from $10^3$ to $5 \times 10^3$, from $5 \times 10^3$ to $10^4$, from $10^5$ to $5 \times 10^4$, from $5 \times 10^4$ to $10^5$, from $10^5$ to $5 \times 10^5$, from $5 \times 10^5$ to $10^6$, from $10^6$ to $5 \times 10^6$, or from $5 \times 10^6$ to $10^7$, or more than $10^7$, DNAs. In some cases, the sample comprises from 5 to $10^7$ DNAs (e.g., that differ from one another in sequence) e.g., from 5 to $10^6$, from 5 to $10^5$, from 5 to 50,000, from 5 to 30,000, from 10 to $10^6$, from 10 to $10^5$, from 10 to 50,000, from 10 to 30,000, from 20 to $10^6$, from 20 to $10^5$, from 20 to 50,000, or from 20 to 30,000 DNAs). In some cases, the sample includes 20 or more DNAs that differ from one another in sequence. In some cases, the sample includes DNAs from a cell lysate (e.g., a eukaryotic cell lysate, a mammalian cell lysate, a human cell lysate, a prokaryotic cell lysate, a plant cell lysate, and the like). For example, in some cases, the sample includes DNA from a cell such as a eukaryotic cell, e.g., a mammalian cell such as a human cell.

The term "sample" is used herein to mean any sample that includes DNA (e.g., in order to determine whether a target DNA is present among a population of DNAs). As noted above, nucleic acids include dsDNAs; or in the case of a ssDNA, a dsDNA prepared from a ssDNA, e.g., by second strand synthesis using the ssDNA as a template; or in the case of an RNA, a dsDNA prepared from an RNA, e.g., by reverse transcription using the RNA as a template to generate a cDNA, and second strand synthesis using the cDNA as a template. The sample can be derived from any source, e.g., the sample can be a synthetic combination of purified DNAs; the sample can be a cell lysate, a DNA-enriched cell lysate, or DNAs isolated and/or purified from a cell lysate. The sample can be from a patient (e.g., for the purpose of diagnosis). The sample can be from permeabilized cells. The sample can be from crosslinked cells. The sample can be in tissue sections. The sample can be from tissues prepared by crosslinking followed by delipidation and adjustment to make a uniform refractive index. Examples of tissue preparation by crosslinking followed by delipidation and adjustment to make a uniform refractive index have been described in, for example, Shah et al., Development (2016) 143, 2862-2867 doi:10.1242/dev.138560.

A "sample" can include a target DNA and a plurality of non-target DNAs. In some cases, the target DNA is present in the sample at one copy per 10 non-target DNAs, one copy per 20 non-target DNAs, one copy per 25 non-target DNAs, one copy per 50 non-target DNAs, one copy per 100 non-target DNAs, one copy per 500 non-target DNAs, one copy per $10^3$ non-target DNAs, one copy per $5\times10^3$ non-target DNAs, one copy per $10^4$ non-target DNAs, one copy per $5\times10^4$ non-target DNAs, one copy per $10^5$ non-target DNAs, one copy per $5\times10^5$ non-target DNAs, one copy per $10^6$ non-target DNAs, or less than one copy per $10^6$ non-target DNAs. In some cases, the target DNA is present in the sample at from one copy per 10 non-target DNAs to 1 copy per 20 non-target DNAs, from 1 copy per 20 non-target DNAs to 1 copy per 50 non-target DNAs, from 1 copy per 50 non-target DNAs to 1 copy per 100 non-target DNAs, from 1 copy per 100 non-target DNAs to 1 copy per 500 non-target DNAs, from 1 copy per 500 non-target DNAs to 1 copy per $10^3$ non-target DNAs, from 1 copy per $10^3$ non-target DNAs to 1 copy per $5\times10^3$ non-target DNAs, from 1 copy per $5\times10^3$ non-target DNAs to 1 copy per $10^4$ non-target DNAs, from 1 copy per $10^4$ non-target DNAs to 1 copy per $10^5$ non-target DNAs, from 1 copy per $10^5$ non-target DNAs to 1 copy per $10^6$ non-target DNAs, or from 1 copy per $10^6$ non-target DNAs to 1 copy per $10^7$ non-target DNAs.

Suitable samples include, but are not limited to, saliva, blood, serum, plasma, urine, aspirate, and biopsy samples. Thus, the term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., DNAs. The term "sample" encompasses biological samples such as a clinical sample such as blood, plasma, serum, aspirate, cerebrospinal fluid (CSF), a bronchoalveolar lavage sample, or sputum; and also includes tissue obtained by surgical resection, tissue obtained by biopsy, cells in culture, cell supernatants, cell lysates, tissue samples, organs, bone marrow, and the like. A "biological sample" includes biological fluids derived therefrom (e.g., cancerous cell, infected cell, etc.), e.g., a sample comprising DNAs that is obtained from such cells (e.g., a cell lysate or other cell extract comprising DNAs).

A sample can comprise, or can be obtained from, any of a variety of cells, tissues, organs, or acellular fluids. Suitable sample sources include eukaryotic cells, bacterial cells, and archaeal cells. Suitable sample sources include single-celled organisms and multi-cellular organisms. Suitable sample sources include single-cell eukaryotic organisms; a plant or a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell, tissue, or organ; a cell, tissue, or organ from an invertebrate animal (e.g. fruit fly, cnidarian, echinoderm, nematode, an insect, an arachnid, etc.); a cell, tissue, fluid, or organ from a vertebrate animal (e.g., fish, amphibian, reptile, bird, mammal); a cell, tissue, fluid, or organ from a mammal (e.g., a human; a non-human primate; an ungulate; a feline; a bovine; an ovine; a caprine; etc.). Suitable sample sources include nematodes, protozoans, and the like. Suitable sample sources include parasites such as helminths, malarial parasites, etc.

Suitable sample sources include a cell, tissue, or organism of any of the six kingdoms, e.g., Bacteria (e.g., Eubacteria); Archaebacteria; Protista; Fungi; Plantae; and Animalia. Suitable sample sources include plant-like members of the kingdom Protista, including, but not limited to, algae (e.g., green algae, red algae, glaucophytes, cyanobacteria); fungus-like members of Protista, e.g., slime molds, water molds, etc.; animal-like members of Protista, e.g., flagellates (e.g., *Euglena*), amoeboids (e.g., amoeba), sporozoans (e.g, Apicomplexa, Myxozoa, Microsporidia), and ciliates (e.g., *Paramecium*). Suitable sample sources include include members of the kingdom Fungi, including, but not limited to, members of any of the phyla: Basidiomycota (club fungi; e.g., members of *Agaricus, Amanita, Boletus, Cantherellus*, etc.); Ascomycota (sac fungi, including, e.g., *Saccharomyces*); Mycophycophyta (lichens); Zygomycota (conjugation fungi); and Deuteromycota. Suitable sample sources include members of the kingdom Plantae, including, but not limited to, members of any of the following divisions: Bryophyta (e.g., mosses), Anthocerotophyta (e.g., hornworts), Hepaticophyta (e.g., liverworts), Lycophyta (e.g., club mosses), Sphenophyta (e.g., horsetails), Psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable sample sources include members of the kingdom Animalia, including, but not limited to, members of any of the following phyla: Porifera (sponges); Placozoa; Orthonectida (parasites of marine invertebrates); Rhombozoa; Cnidaria (corals, anemones, jellyfish, sea pens, sea pansies, sea wasps); Ctenophora (comb jellies); Platyhelminthes (flatworms); Nemertina (ribbon worms); Ngathostomulida (jawed worms)p Gastrotricha; Rotifera; Priapulida; Kinorhyncha; Loricifera; *Acanthocephala*; Entoprocta; Nemotoda; Nematomorpha; Cycliophora; Mollusca (mollusks); Sipuncula (peanut worms); Annelida (segmented worms); Tardigrada (water bears); Onychophora (velvet worms); Arthropoda (including the subphyla: Chelicerata, Myriapoda, Hexapoda, and Crustacea, where the Chelicerata include, e.g., arachnids, Merostomata, and Pycnogonida, where the Myriapoda include, e.g., Chilopoda (centipedes), Diplopoda (millipedes), Paropoda, and Symphyla, where the Hexapoda include insects, and where the Crustacea include shrimp, krill, barnacles, etc.; Phoronida; Ectoprocta (moss animals); Brachiopoda; Echinodermata (e.g. starfish, sea daisies, feather stars, sea urchins, sea cucumbers, brittle stars, brittle baskets, etc.); Chaetognatha (arrow worms); Hemichordata (acorn worms); and Chordata. Suitable members of Chordata include any member of the following subphyla: Urochordata (sea squirts; including Ascidiacea, Thaliacea, and Larvacea); Cephalochordata (lancelets); Myxini (hagfish);

and Vertebrata, where members of Vertebrata include, e.g., members of Petromyzontida (lampreys), Chondrichthyces (cartilaginous fish), Actinopterygii (ray-finned fish), Actinista (coelocanths), Dipnoi (lungfish), Reptilia (reptiles, e.g., snakes, alligators, crocodiles, lizards, etc.), Aves (birds); and Mammalian (mammals). Suitable plants include any monocotyledon and any dicotyledon.

Suitable sources of a sample include cells, fluid, tissue, or organ taken from an organism; from a particular cell or group of cells isolated from an organism; etc. For example, where the organism is a plant, suitable sources include xylem, the phloem, the cambium layer, leaves, roots, etc. Where the organism is an animal, suitable sources include particular tissues (e.g., lung, liver, heart, kidney, brain, spleen, skin, fetal tissue, etc.), or a particular cell type (e.g., neuronal cells, epithelial cells, endothelial cells, astrocytes, hepatocytes, cardiac cells, macrophages, glial cells, islet cells, T lymphocytes, B lymphocytes, etc.).

In some cases, the source of the sample is a (or is suspected of being a diseased cell, fluid, tissue, or organ. In some cases, the source of the sample is a normal (non-diseased) cell, fluid, tissue, or organ. In some cases, the source of the sample is a (or is suspected of being a pathogen-infected cell, tissue, or organ. For example, the source of a sample can be an individual who may or may not be infected—and the sample could be any biological sample (e.g., blood, saliva, biopsy, plasma, serum, bronchoalveolar lavage, sputum, a fecal sample, cerebrospinal fluid, a fine needle aspirate, a swab sample (e.g., a buccal swab, a cervical swab, a nasal swab), interstitial fluid, synovial fluid, nasal discharge, tears, buffy coat, a mucous membrane sample, an epithelial cell sample (e.g., epithelial cell scraping), etc.) collected from the individual. In some cases, the sample is a cell-free liquid sample. In some cases, the sample is a liquid sample that can comprise cells.

Pathogens include viruses, fungi, helminths, protozoa, malarial parasites, *Plasmodium* parasites, *Toxoplasma* parasites, *Schistosoma* parasites, and the like. "Helminths" include roundworms, heartworms, and phytophagous nematodes (Nematoda), flukes (Tematoda), *Acanthocephala*, and tapeworms (Cestoda). Protozoan infections include infections from *Giardia* spp., *Trichomonas* spp., African trypanosomiasis, amoebic dysentery, babesiosis, balantidial dysentery, Chaga's disease, coccidiosis, malaria and toxoplasmosis. Examples of pathogens such as parasitic/protozoan pathogens include, but are not limited to: *Plasmodium falciparum, Plasmodium vivax, Trypanosoma cruzi* and *Toxoplasma gondin*. Fungal pathogens include, but are not limited to: *Cryptococcus neoformans, Histoplasma capsulatum, Coccidioides immitis, Blastomyces dermatitidis, Chlamydia trachomatis*, and *Candida albicans*. Pathogenic viruses include, e.g., immunodeficiency virus (e.g., HIV); influenza virus; dengue; West Nile virus; herpes virus; yellow fever virus; Hepatitis Virus C; Hepatitis Virus A; Hepatitis Virus B; papillomavirus; and the like. Pathogenic viruses can include DNA viruses such as: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), epstein-barr virus (EBV), cytomegalovirus (CMV), herpes lymphotropic virus, *Pityriasis Rosea*, kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 GI); Geminiviridae; Nanoviridae; Phycodnaviridae; and the like. Pathogens can include, e.g., DNAviruses [e.g.: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), Epstein-Barr virus (EBV), cytomegalovirus (CMV), herpes lymphotropic virus, *Pityriasis rosea*, Kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 GI); Geminiviridae; Nanoviridae; Phycodnaviridae; and the like], *Mycobacterium tuberculosis, Streptococcus agalactiae*, methicillin-resistant *Staphylococcus aureus, Legionella pneumophila, Streptococcus pyogenes, Escherichia coli, Neisseria gonorrhoeae, Neisseria meningitidis*, Pneumococcus, *Cryptococcus neoformans, Histoplasma capsulatum, Hemophilus influenzae* B, *Treponema pallidum*, Lyme disease spirochetes, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, Sendai virus, feline leukemia virus, Reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiense, Trypanosoma brucei, Schistosoma mansoni, Schistosoma japonicum, Babesia bovis, Eimeria tenella, Onchocerca volvulus, Leishmania tropica, Mycobacterium tuberculosis, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium*, and *M. pneumoniae*.

Detection

In some cases, a method of the present disclosure comprises detecting a target DNA in a sample. Type V CRISPR/Cas proteins, e.g., Cas12 proteins such as Cpf1 (Cas12a) and C2c1 (Cas12b) can promiscuously cleave non-targeted single stranded DNA (ssDNA) once activated by detection of a target DNA (double or single stranded). Once a type V CRISPR/Cas effector protein (e.g., a Cas12 protein such as Cas12a, Cas12b, Cas12c, Cas12d, Cas12e) is activated by a guide RNA, which occurs when the guide RNA hybridizes to a target sequence of a target DNA (i.e., the sample includes the targeted DNA), the protein becomes a nuclease that promiscuously cleaves ssDNAs (i.e., the nuclease cleaves non-target ssDNAs, i.e., ssDNAs to which the guide sequence of the guide RNA does not hybridize). Thus, when the target DNA is present in the sample (e.g., in some cases above a threshold amount), the result is cleavage of ssDNAs in the sample, which can be detected using any convenient detection method (e.g., using a labeled single stranded detector DNA).

Provided are compositions and methods for detecting a target DNA (double stranded or single stranded) in a sample. In some cases, a detector DNA is used that is single stranded (ssDNA) and does not hybridize with the guide sequence of the guide RNA (i.e., the detector ssDNA is a non-target ssDNA). Such methods can include (a) contacting the sample with: (i) a type V CRISPR/Cas effector protein (e.g., a Cas12 protein); (ii) a guide RNA comprising: a region that binds to the type V CRISPR/Cas effector protein, and a guide sequence that hybridizes with the target DNA; and (iii) a detector DNA that is single stranded and does not hybridize with the guide sequence of the guide RNA; and (b) measuring a detectable signal produced by cleavage of the single stranded detector DNA by the type V CRISPR/Cas effector protein, thereby detecting the target DNA. As noted above, once a subject Type V CRISPR/Cas effector protein (e.g., a Cas12 protein such as Cas12a, Cas12b, Cas12c, Cas12d, Cas12e) is activated by a guide RNA, which occurs when the sample includes a target DNA to which the guide RNA hybridizes (i.e., the sample includes the targeted target DNA), the Type V CRISPR/Cas effector protein (e.g., a Cas12 protein such as Cas12a, Cas12b, Cas12c, Cas12d, Cas12e) is activated and functions as an endoribonuclease that non-specifically cleaves ssDNAs (including non-target ssDNAs) present in the sample. Thus, when the targeted target DNA is present in the sample (e.g., in some cases above a threshold amount), the result is cleavage of ssDNA (including non-target ssDNA) in the sample, which can be detected using any convenient detection method (e.g., using a labeled detector ssDNA).

Also provided are compositions and methods for cleaving single stranded DNAs (ssDNAs) (e.g., non-target ssDNAs). Such methods can include contacting a population of nucleic acids, wherein said population comprises a target DNA and a plurality of non-target ssDNAs, with: (i) a type V CRISPR/Cas effector protein; and (ii) a guide RNA comprising: a region that binds to the type V CRISPR/Cas effector protein, and a guide sequence that hybridizes with the target DNA, wherein the type V CRISPR/Cas effector protein cleaves non-target ssDNAs of said plurality. Such a method can be used, e.g., to cleave foreign ssDNAs (e.g., viral DNAs) in a cell.

The contacting step of a subject method can be carried out in a composition comprising divalent metal ions. The contacting step can be carried out in an acellular environment, e.g., outside of a cell. The contacting step can be carried out inside a cell. The contacting step can be carried out in a cell in vitro. The contacting step can be carried out in a cell ex vivo. The contacting step can be carried out in a cell in vivo.

The guide RNA can be provided as RNA or as a nucleic acid encoding the guide RNA (e.g., a DNA such as a recombinant expression vector). The Type V CRISPR/Cas effector protein (e.g., a Cas12 protein such as Cas12a, Cas12b, Cas12c, Cas12d, Cas12e) can be provided as a protein or as a nucleic acid encoding the protein (e.g., an mRNA, a DNA such as a recombinant expression vector). In some cases, two or more (e.g., 3 or more, 4 or more, 5 or more, or 6 or more) guide RNAs can be provided by (e.g., using a precursor guide RNA array, which can be cleaved by the Type V CRISPR/Cas effector protein into individual ("mature") guide RNAs).

In some cases (e.g., when contacting with a guide RNA and a Type V CRISPR/Cas effector protein (e.g., a Cas12 protein such as Cas12a, Cas12b, Cas12c, Cas12d, Cas12e)), the sample is contacted for 2 hours or less (e.g., 1.5 hours or less, 1 hour or less, 40 minutes or less, 30 minutes or less, 20 minutes or less, 10 minutes or less, or 5 minutes or less, or 1 minute or less) prior to the measuring step. For example, In some cases, the sample is contacted for 40 minutes or less prior to the measuring step. In some cases, the sample is contacted for 20 minutes or less prior to the measuring step. In some cases, the sample is contacted for 10 minutes or less prior to the measuring step. In some cases, the sample is contacted for 5 minutes or less prior to the measuring step. In some cases, the sample is contacted for 1 minute or less prior to the measuring step. In some cases, the sample is contacted for from 50 seconds to 60 seconds prior to the measuring step. In some cases, the sample is contacted for from 40 seconds to 50 seconds prior to the measuring step. In some cases, the sample is contacted for from 30 seconds to 40 seconds prior to the measuring step. In some cases, the sample is contacted for from 20 seconds to 30 seconds prior to the measuring step. In some cases, the sample is contacted for from 10 seconds to 20 seconds prior to the measuring step.

A method of the present disclosure for detecting a target DNA (single-stranded or double-stranded) in a sample can detect a target DNA with a high degree of sensitivity. In some cases, a method of the present disclosure can be used to detect a target DNA present in a sample comprising a plurality of DNAs (including the target DNA and a plurality of non-target DNAs), where the target DNA is present at one or more copies per $10^7$ non-target DNAs (e.g., one or more copies per $10^6$ non-target DNAs, one or more copies per $10^5$ non-target DNAs, one or more copies per $10^4$ non-target DNAs, one or more copies per $10^3$ non-target DNAs, one or more copies per $10^2$ non-target DNAs, one or more copies per 50 non-target DNAs, one or more copies per 20 non-target DNAs, one or more copies per 10 non-target DNAs, or one or more copies per 5 non-target DNAs). In some cases, a method of the present disclosure can be used to detect a target DNA present in a sample comprising a plurality of DNAs (including the target DNA and a plurality of non-target DNAs), where the target DNA is present at one or more copies per $10^{18}$ non-target DNAs (e.g., one or more copies per $10^{15}$ non-target DNAs, one or more copies per $10^{12}$ non-target DNAs, one or more copies per $10^9$ non-target DNAs, one or more copies per $10^6$ non-target DNAs, one or more copies per $10^5$ non-target DNAs, one or more copies per $10^4$ non-target DNAs, one or more copies per $10^3$ non-target DNAs, one or more copies per $10^2$ non-target DNAs, one or more copies per 50 non-target DNAs, one or more copies per 20 non-target DNAs, one or more copies per 10 non-target DNAs, or one or more copies per 5 non-target DNAs).

In some cases, a method of the present disclosure can detect a target DNA present in a sample, where the target DNA is present at from one copy per $10^7$ non-target DNAs to one copy per 10 non-target DNAs (e.g., from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^5$ non-target DNAs to 1 copy per 10 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 10 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, a method of the present disclosure can detect a target DNA present in a sample, where the target DNA is present at from one copy per $10^{18}$ non-target DNAs to one copy per 10 non-target DNAs (e.g., from 1 copy per $10^{18}$ non-target DNAs to 1 copy per $10^2$ non-target DNAs, from 1 copy per $10^{15}$ non-target DNAs to 1 copy per $10^2$ non-target DNAs, from 1 copy per $10^{12}$ non-target DNAs to 1 copy per $10^2$ non-target DNAs, from 1 copy per $10^9$ non-target DNAs to 1 copy per $10^2$ non-target DNAs, from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 10 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 10 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, a method of the present disclosure can detect a target DNA present in a sample, where the target DNA is present at from one copy per $10^7$ non-target DNAs to one copy per 100 non-target DNAs (e.g., from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^5$ non-target DNAs to 1 copy per 100 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 100 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, the threshold of detection, for a subject method of detecting a target DNA in a sample, is 10 nM or less. The term "threshold of detection" is used herein to describe the minimal amount of target DNA that must be present in a sample in order for detection to occur. Thus, as an illustrative example, when a threshold of detection is 10 nM, then a signal can be detected when a target DNA is present in the sample at a concentration of 10 nM or more. In some cases, a method of the present disclosure has a threshold of detection of 5 nM or less. In some cases, a method of the present disclosure has a threshold of detection of 1 nM or less. In some cases, a method of the present disclosure has a threshold of detection of 0.5 nM or less. In some cases, a method of the present disclosure has a threshold of detection of 0.1 nM or less. In some cases, a method of the present disclosure has a threshold of detection of 0.05 nM or less. In some cases, a method of the present disclosure has a threshold of detection of 0.01 nM or less. In some cases, a method of the present disclosure has a threshold of detection of 0.005 nM or less. In some cases, a method of the present disclosure has a threshold of detection of 0.001 nM or less. In some cases, a method of the present disclosure has a threshold of detection of 0.0005 nM or less. In some cases, a method of the present disclosure has a threshold of detection of 0.0001 nM or less. In some cases, a method of the present disclosure has a threshold of detection of 0.00005 nM or less. In some cases, a method of the present disclosure has a threshold of detection of 0.00001 nM or less. In some cases, a method of the present disclosure has a threshold of detection of 10 pM or less. In some cases, a method of the present disclosure has a threshold of detection of 1 pM or less. In some cases, a method of the present disclosure has a threshold of detection of 500 fM or less. In some cases, a method of the present disclosure has a threshold of detection of 250 fM or less. In some cases, a method of the present disclosure has a threshold of detection of 100 fM or less. In some cases, a method of the present disclosure has a threshold of detection of 50 fM or less. In some cases, a method of the present disclosure has a threshold of detection of 500 aM (attomolar) or less. In some cases, a method of the present disclosure has a threshold of detection of 250 aM or less. In some cases, a method of the present disclosure has a threshold of detection of 100 aM or less. In some cases, a method of the present disclosure has a threshold of detection of 50 aM or less. In some cases, a method of the present disclosure has a threshold of detection of 10 aM or less. In some cases, a method of the present disclosure has a threshold of detection of 1 aM or less.

In some cases, the threshold of detection (for detecting the target DNA in a subject method), is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM) (where the concentration refers to the threshold concentration of target DNA at which the target DNA can be detected). In some cases, a method of the present disclosure has a threshold of detection in a range of from 800 fM to 100 pM. In some cases, a method of the present disclosure has a threshold of detection in a range of from 1 pM to 10 pM. In some cases, a method of the present disclosure has a threshold of detection in a range of from 10 fM to 500 fM, e.g., from 10 fM to 50 fM, from 50 fM to 100 fM, from 100 fM to 250 fM, or from 250 fM to 500 fM.

In some cases, the minimum concentration at which a target DNA can be detected in a sample is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, the minimum concentration at which a target DNA can be detected in a sample is in a range of from 800 fM to 100 pM. In some cases, the minimum concentration at which a target DNA can be detected in a sample is in a range of from 1 pM to 10 pM.

In some cases, the threshold of detection (for detecting the target DNA in a subject method), is in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM) (where the concentration refers to the threshold concentration of target DNA at which the target DNA can be detected). In some cases, a method of the present disclosure has a threshold of detection in a range of from 1 aM to 800 aM. In some cases, a method of the present disclosure has a threshold of detection in a range of from 50 aM to 1 pM. In some cases, a method of the present disclosure has a threshold of detection in a range of from 50 aM to 500 fM.

In some cases, the minimum concentration at which a target DNA can be detected in a sample is in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, the minimum concentration at which a target DNA can be detected in a sample is in a range of from 1 aM to 500 pM. In some cases, the minimum concentration at which a target DNA can be detected in a sample is in a range of from 100 aM to 500 pM.

In some cases, a subject composition or method exhibits an attomolar (aM) sensitivity of detection. In some cases, a subject composition or method exhibits a femtomolar (fM) sensitivity of detection. In some cases, a subject composition or method exhibits a picomolar (pM) sensitivity of detection. In some cases, a subject composition or method exhibits a nanomolar (nM) sensitivity of detection.

Kits

The present disclosure provides a kit for carrying out a method of the present disclosure (e.g., a method of characterizing a target DNA present in a sample).

In some cases, a kit of the present disclosure comprises:
A) a type V CRISPR/Cas effector protein;
B) one or more guide RNAs, where the one or more guide RNAs comprise: i) a region that binds to the type V CRISPR/Cas effector protein; and ii) a guide sequence that hybridizes with the target DNA; and
C) a double-stranded nucleic acid adapter, where the adapter comprises a 5' overhang that comprises a stretch of from 3 to 15 contiguous nucleotides that are complementary to a contiguous stretch of nucleotides of the same length in the 5' overhang of a PAM-distal cleavage product generated by action of the type V CRISPR/Cas effector protein and the one or more guide RNAs on the target DNA.

In some cases, the kit also includes one or more reagents for determining the nucleotide sequence of a ligation product formed by ligating the adapter and the PAM-distal cleavage product.

In some cases, the kit also includes one or more reagents for amplifying the target DNA. For example, in some cases, the kit comprises one or more sets of primer pairs.

In some cases, one or more components of a kit of the present disclosure is lyophilized.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-48 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A method for characterizing a target DNA present in a sample, the method comprising:
A) contacting the sample with:
(a) a type V CRISPR/Cas effector protein; and
(b) one or more guide RNAs, wherein the one or more guide RNAs comprise: i) a region that binds to the type V CRISPR/Cas effector protein; and ii) a guide sequence that hybridizes with the target DNA, wherein said contacting generates a protospacer adjacent motif (PAM)-distal cleavage product comprising a 5' overhang;
B) ligating a double-stranded nucleic acid adapter to the cleavage product, wherein the adapter comprises a 5' overhang that comprises a stretch of from 3 to 15 contiguous nucleotides that are complementary to a contiguous stretch of nucleotides of the same length in the 5' overhang of the PAM-distal cleavage product, wherein said ligating generates a ligation product comprising the adapter and the PAM-distal cleavage product; and
C) determining the nucleotide sequence of the PAM-distal cleavage product present in the ligation product.

Aspect 2. The method of aspect 1, wherein the type V CRISPR/Cas effector protein is a Cas12 protein.

Aspect 3. The method of aspect 1, wherein the type V CRISPR/Cas effector protein is a Cas12a (Cpf1) protein.

Aspect 4. The method of aspect 1, wherein the type V CRISPR/Cas effector protein is a Cas12b (C2c1) protein.

Aspect 5. The method of aspect 1, wherein the type V CRISPR/Cas effector protein is a Cas12d protein.

Aspect 6. The method of aspect 1, wherein the type V CRISPR/Cas effector protein is a Cas14a protein.

Aspect 7. The method of any one of aspects 1-6, wherein the target DNA is single stranded.

Aspect 8. The method of any one of aspects 1-6, wherein the target DNA is double stranded.

Aspect 9. The method of any one of aspects 1-8, wherein the target DNA is viral DNA.

Aspect 10. The method of aspect 9, wherein the target DNA is papovavirus, hepadnavirus, herpesvirus, adenovirus, poxvirus, or parvovirus DNA.

Aspect 11. The method of any one of aspects 1-8, wherein the target DNA is bacterial DNA.

Aspect 12. The method of any one of aspects 1-8, wherein the target DNA is tick-borne pathogen DNA.

Aspect 13. The method of any one of aspects 1-8, wherein the target DNA is multiple drug resistant bacterial DNA.

Aspect 14. The method of any one of aspects 1-8, wherein the target DNA is DNA of a eukaryotic pathogen.

Aspect 15. The method of aspect 14, wherein the eukaryotic pathogen is a pathogenic protozoan, a pathogenic fungus, or a pathogenic helminth.

Aspect 16. The method of aspect 14, wherein the pathogenic protozoan is a *Plasmodium* spp., a *Trypanosoma* spp., a *Trichomonas* spp., an amoeba, a *Giardia* spp., or a *Toxoplama* spp.

Aspect 17. The method of aspect 15, wherein the pathogenic fungus is an *Aspergillus* spp., a *Candida* spp., an *Epidermophyton* spp., a *Histoplasma* spp., or a *Trichphtyon* spp.

Aspect 18. The method of aspect 15, wherein the pathogenic helminth is a nematode or a platyhelminth.

Aspect 19. The method of aspect 18, wherein the pathogenic helminth is an *Ascaris* spp., an *Echinococcus* spp., a *Schistosoma* spp., a *Strongyloides* spp., a *Taenia* spp., or a *Trichinella* spp.

Aspect 20. The method of any one of aspects 1-8, wherein the target DNA is fetal DNA.

Aspect 21. The method of any one of aspects 1-20, comprising contacting the sample with 2 or more guide RNAs, wherein the 2 or more guide RNAs differ from one another in the guide sequence.

Aspect 22. The method of aspect 21, comprising contacting the sample with from 2 to 10 guide RNAs.

Aspect 23. The method of any one of aspects 1-22, wherein the sample comprises a cell.

Aspect 24. The method of any one of aspects 1-22, wherein the sample is a cell lysate.

Aspect 25. The method of any one of aspects 1-22, wherein the sample is a cell-free sample.

Aspect 26. The method of any one of aspects 1-22, wherein the sample is blood, serum, plasma, bronchoalveolar lavage, sputum, urine, cerebrospinal fluid, feces, or a biopsy sample.

Aspect 27. The method of any one of aspects 1-26, comprising amplifying the target DNA prior to said contacting step.

Aspect 28. The method of aspect 27, wherein said amplifying comprises contacting the sample with 2 or more sets of primer pairs.

Aspect 29. The method of aspect 28, wherein the 2 or more sets of primer pairs provides for amplification of DNA of a plurality of different pathogens.

Aspect 30. The method of aspect 27, wherein said amplifying comprises isothermal amplification.

Aspect 31. The method of any one of aspects 27-30, wherein said amplification comprises contacting the sample with 1 or more pairs of forward and reverse primers, wherein the 1 or more pairs of forward and reverse primers are selected from the forward and reverse primers depicted in any one of SEQ ID Nos: 71 to 6432.

Aspect 32. The method of any one of aspects 27-30, wherein said amplification comprises contacting the sample with 1 or more pairs of forward and reverse primers, wherein the 1 or more pairs of forward and reverse primers are selected from the forward and reverse primers depicted in any one of SEQ ID Nos: 6433 to 13607.

Aspect 33. The method of any one of aspects 27-30, wherein said amplification comprises contacting the sample with 1 or more pairs of forward and reverse primers, wherein the 1 or more pairs of forward and reverse primers are selected from the forward and reverse primers depicted in SEQ ID Nos:13608 to 17378.

Aspect 34. The method of aspect 1, wherein the adapter comprises a 3' deoxyadenosine overhang.

Aspect 35. The method of any one of aspects 1-34, wherein sequence determination is carried out by nanopore sequencing.

Aspect 36. The method of any one of aspects 1-34, wherein the target DNA is present in the sample at a concentration as low as 200 fM.

Aspect 37. The method of any one of aspects 1-36, further comprising contacting the sample with a detector DNA that is single stranded and does not hybridize with the guide sequence of the guide RNA; and measuring a detectable signal produced by cleavage of the single stranded detector DNA by the type V CRISPR/Cas effector protein, thereby detecting the target DNA Aspect 38. The method of aspect 37, wherein the single stranded detector DNA comprises a fluorescence-emitting dye pair.

Aspect 39. The method of aspect 38, wherein the fluorescence-emitting dye pair is a fluorescence resonance energy transfer (FRET) pair.

Aspect 40. The method of aspect 39, wherein the fluorescence-emitting dye pair is a quencher/fluor pair.

Aspect 41. The method of any one of aspects 1-40, wherein the single stranded detector DNA comprises a modified nucleobase, a modified sugar moiety, and/or a modified nucleic acid linkage.

Aspect 42. A kit for characterizing a target DNA present in a sample, the system comprising:

A) a type V CRISPR/Cas effector protein;

B) one or more guide RNAs, wherein the one or more guide RNAs comprise: i) a region that binds to the type V CRISPR/Cas effector protein; and ii) a guide sequence that hybridizes with the target DNA; and C) a double-stranded nucleic acid adapter, wherein the adapter comprises a 5' overhang that comprises a stretch of from 3 to 15 contiguous nucleotides that are complementary to a contiguous stretch of nucleotides of the same length in the 5' overhang of protospacer adjacent motif (PAM)-distal cleavage product generated by action of the type V CRISPR/Cas effector protein and the one or more guide RNAs on the target DNA.

Aspect 43. The kit of aspect 42, further comprising one or more reagents for determining the nucleotide sequence of a ligation product formed by ligating the adapter and the PAM-distal cleavage product.

Aspect 44. The kit of aspect 42 or 43, further comprising one or more reagents for amplifying the target DNA.

Aspect 45. The kit of aspect 44, comprising one or more sets of primer pairs.

Aspect 46. The kit of aspect 45, wherein the one or more pairs of forward and reverse primers are selected from the forward and reverse primers depicted in any one of SEQ ID Nos: 71 to 6432.

Aspect 47. The kit of aspect 45, wherein the one or more pairs of forward and reverse primers are selected from the forward and reverse primers depicted in any one of SEQ ID Nos: 6433 to 13607.

Aspect 48. The kit of aspect 45, wherein the one or more pairs of forward and reverse primers are selected from the forward and reverse primers depicted in SEQ ID Nos:13608 to 17378.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or see, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Primers for detecting antibiotic resistant bacteria (e.g., detecting antibiotic resistance genes) were designed as follows:

1) Start with the 11,376 gene references (unique accession numbers) in the ARDB database; 2) Use CD-HIT to narrow the references down to 1,079 gene references (each with <95% identity to each other); 3) Design primers using automated algorithm (600 bp fragment size, 300 bp overlap, 50 nt selection window); 4) Remove primers with Tm>2 SD, homopolymeric; 5) Remove any reverse primers that overlap with forward primers.

Figure 9A:
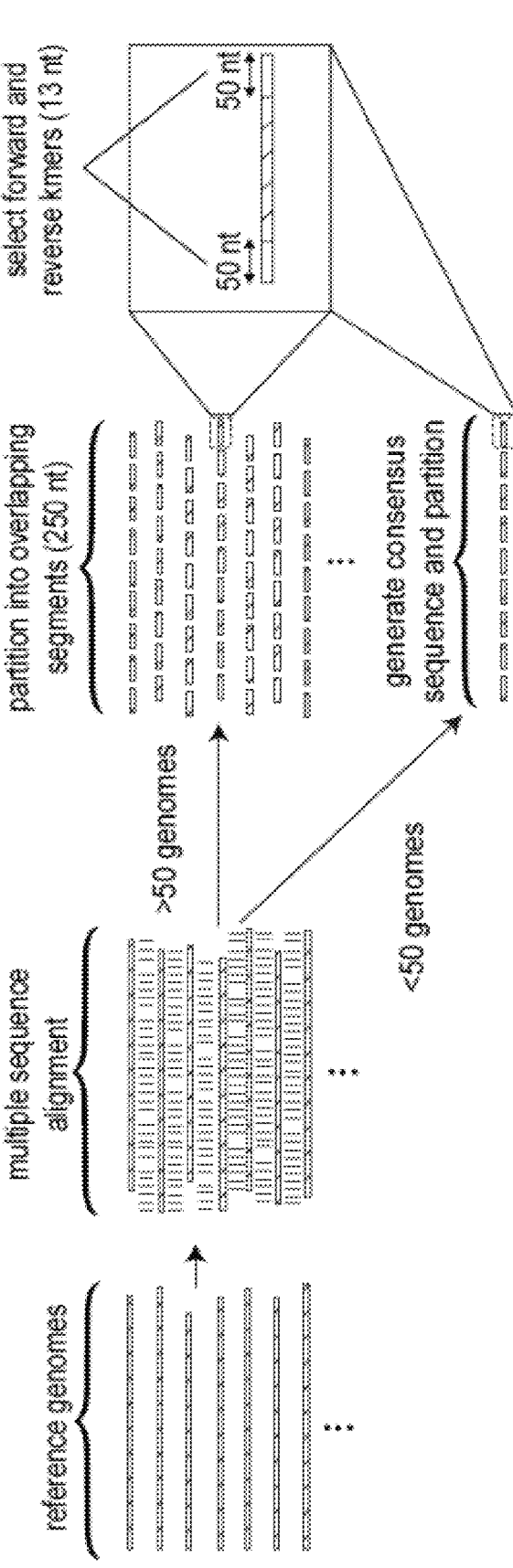
FIG. 9A-9B provides a schematic depiction of a method of designing primers suitable for amplifying target nucleic acids encoding antibiotic resistance factors.
Figure 9B:
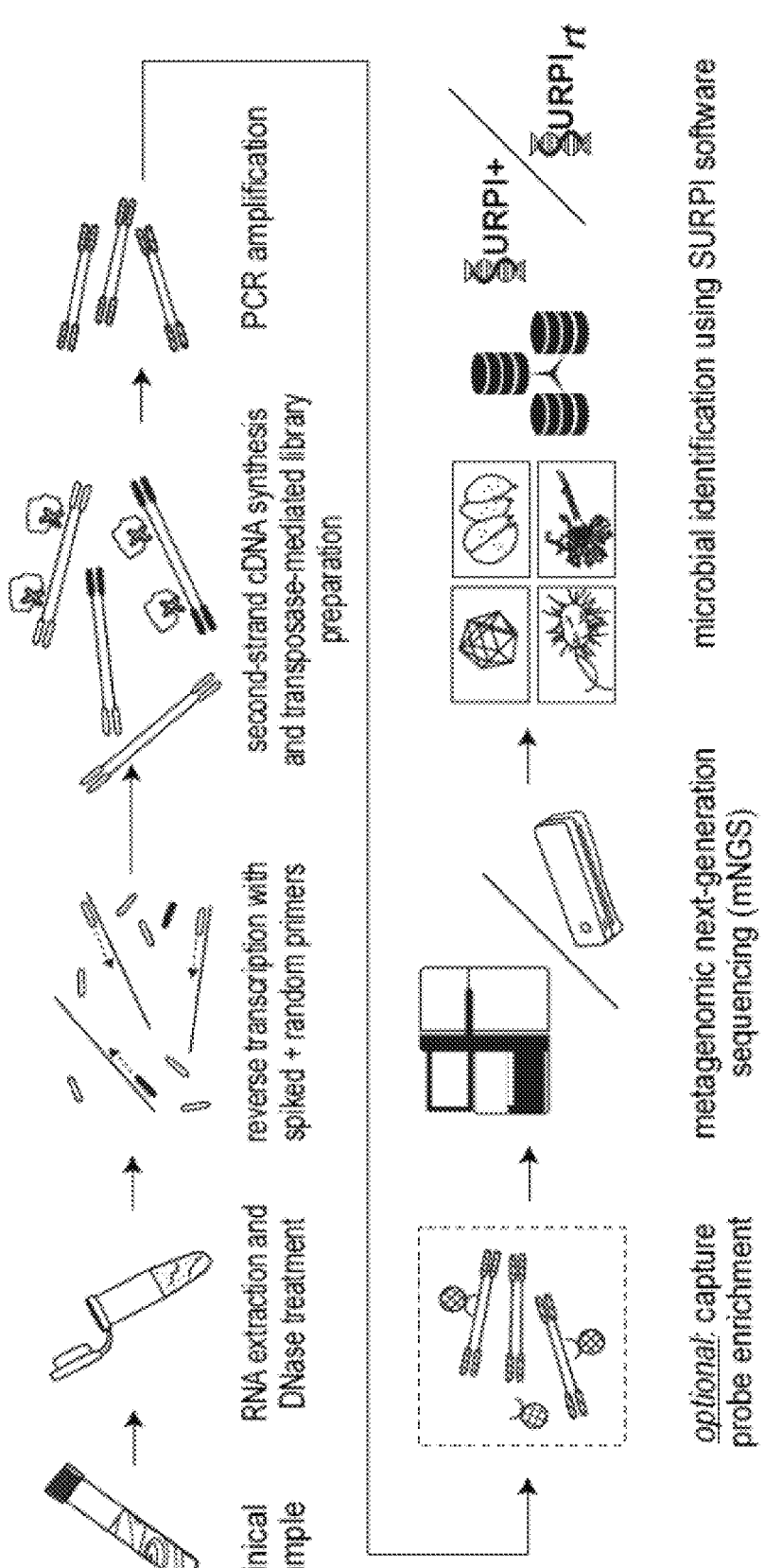

This method is depicted schematically in FIG. 9A-9B.

The genes that were targeted are denoted as follows: (position highlighted in bold, with the corresponding position in the bacterial genome in bold and italics): >gi|108796981|ref|NC008146l|_gi|108797245|ref|YP_637442.1|_aac2i_305541_306162.

Example 2: Metagenomic Sequencing with Spiked Primer Enrichment (MSSPE)

Clinical Sample Collection

Viral cultures of ZIKV (Uganda strain), DENV (type 1), and MS2 bacteriophage were purchased from American Type Culture Collection (ATCC, Manassas VA, USA). Ebola cultures Kikwit strain in TRIzol LS (Thermo Fisher Scientific, Waltham, MA, USA) was used. Clinical ZIKV serum samples were collected by Central Laboratory of Epidemiology (CLE), IMSS in Mexico City, Mexico. Real-time quantitative reverse transcription PCR (RT-PCR) testing was used for ZIKV detection and viral titer determination by standard curve analysis (Lanciotti et al. (2008) *Emerg Infect Dis* 14:1232; Sardi et al. (2016) *J Clin Microbiol* 54:2348). Forward and reverse primers (ZIKV 1086 and ZIKV 1162c, respectively) and Carboxyfluorescein (FAM)-labelled probes (ZIKV 1107-FAM) were used as previously described (Lanciotti et al. (2008) supra). Clinical Ebola samples collected from patients in the 2014 Boende and 2018 North Kivu province outbreaks were used. Clinical HIV and hepatitis C plasma samples were obtained from the UCSF Clinical Microbiology Laboratory (San Francisco, USA). The CSF sample from a patient with POWV meningoencephalitis was provided by Boston Children's Hospital. The CSF sample from a patient from SLEV meningoencephalitis was provided by University of California, Los Angeles (UCLA) Medical Center (Chiu et al. (2017) *Emerg Infect Dis* 23:1694). Negative plasma sample matrix used as a "no template" control (NTC) was obtained from Golden West Biologicals Inc. (Temecula, CA, USA).

MSSPE Viral Spiked Primer Design

Multiple sequence alignment (MSA) of viral genomes (downloaded from NCBI GenBank as of September 2017) was performed using MAFFT at default parameters (algorithm="Auto", scoring matrix="200 PAM/k=2", gap open penalty=1.53, offset value=0.123) (Katoh et al. (2014) *Methods Mol Biol* 1079:131-146). An in-house bioinformatics pipeline named "MSSPE-design" was developed on an Ubuntu Linux computational server for automated design of spiked primers. Briefly, the MSA-aligned genomes were partitioned into overlapping 500 nucleotide (nt) segments with 250 nt overlap using PYFASTA (http://pypi.python.org/pypi/pyfasta/). Forward or reverse 13 nt primers were selected from 50 nt regions at the ends of each segment by iteratively ranking candidate 13mer ("kmer") sequences in reverse order by frequency, selecting the top kmer shared by the most segments and not containing any ambiguous nucleotides, and then removing segments sharing that 13mer before repeating the process on the remaining segments. To decrease overall spiked primer costs, the iterations were repeated until the number of remaining segments containing a shared kmer was below a pre-designated threshold (ranging from n=1 for viruses with only a limited number of genomes/genome segments such as CCHF to n=10 for viruses comprising thousands of genomes and multiple genotypes such as DENV). Spiked primers were filtered by removal of primers with melting temperatures (Tm) greater than 2 standard deviations from the mean or that were predicted to self-dimerize or cross-dimerize with a ΔG value of −9 kcals/mol or more negative.

Spiked primers were ordered and synthesized by Integrated DNA Technologies Inc. (IDT, Coralville, Iowa, USA). Forward or reverse spiked primer oligonucleotides targeting individual viruses were synthesized on a 10 nmole scale in 96-well plates with standard desalting and 6 nm of each individual oligonucleotide were mixed and then resuspended to a final volume of 500 μL in IDTE pH 8.0. Spiked primer panels (ArboV, HFV, and AHV) were designed by mixing the spiked primers for each individual virus in equimolar ratios and then diluting with TE (Tris-EDTA) buffer to the desired concentration.

Construction of Metagenomic Sequencing Libraries

Viral RNA was extracted from 200 μL of contrived or clinical patient samples using the EZ1 Advanced XL BioRobot and EZ1 Virus Mini Kit (Qiagen, Redwood City, CA), with the exception of EBOV RNA, which was extracted manually in the viral hemorrhagic fever reference laboratory in INRB, Kinshasa using the Direct-zol RNA MiniPrep Kit (Zymo Research, Irvine, CA). 25 μL of nucleic acid extract was treated with DNase (3 μL Turbo DNase, 1 μL Baseline, 5 μL Turbo buffer and 16 μL nuclease-free water), and incubated on an Eppendorf ThermoMixer at 37° C., 600 rpm for 30 min. The Zymo RNA Clean and Concentrator kit (Zymo Research, Irvine, CA) was used to clean up DNase-treated RNA, and the final RNA was eluted in 32 μL water. The RNA was then mixed with random hexamer (RH) alone (1 μM) or spiked primer plus RH in a 10:1 ratio of spiked primer to RH, and heated to 65° C. for 5 min. The reverse transcription master mix (10 μL SuperScript III buffer, L dNTP of 12.5 mM, 2.5 μL DTT of 0.1M, 1 μL SuperScript III enzyme) was added to each sample and incubated at 25° C. for 5 min, followed by 42° C. for 30 min and 94° C. for 2 min. After cooling to 10° C., a second-strand synthesis master mix (3.7 μL Sequenase buffer, 0.225 μL Sequenase enzyme and 1.1 μL water) was added to each reaction, followed by a slow 2 min ramp to 37° C. and 8 min incubation. The resulting cDNA was cleaned up using the Zymo DNA Clean and Concentrator kit (Zymo Research, Irvine, CA), with the addition of 10 μL linear acrylamide to each sample, and eluted in 10 μL water. Using the Illumina Nextera XT kit, 2.5 μL sample cDNA was incubated at 55° C. for 5 mins in tagmentation mix (10 μL TD buffer and 5 μL ATM enzyme), and immediately neutralized with 2.5 μL NT buffer. 12.5 μL of tagmented DNA was then transferred to reaction tube containing indexing mix (7.5 μL Nextera XT NPM, 2.5 μL N-7xx primer and 2.5 μL S-5xx primer), followed by PCR amplification (72° C. for 3 min, 95° C. for 30 s, followed by 16 cycles of denaturation (95° C. for 10 s), annealing (55° C. for 30 s), and extension (72° C. for 30 s), with a final extension at 72° C. for 5 min). After PCR, 3 μL of PCR product was analyzed by 2% gel electrophoresis to check for library size and band intensity. If no band or only a very faint band was observed on the gel, another round of recovery PCR was performed. For recovery PCR, the library was washed using 0.9×AMPure XT beads (Beckman Coulter, Carlsb ad, CA, USA) and 5 μL clean library was mixed with 45 μL master mix (10 μL buffer, 2.5 μL of 10 uM Nextera general primers (forward 5'AATGATACGGCGAC-CACCGA3' (SEQ ID NO:17), reverse 5'CAAGCAGAA-GACGGCATACG3' (SEQ ID NO:18)), 1 μL dNTP, 0.5 μL Phusion DNA polymerase enzyme and 31 μL water), followed by a 95° C. incubation for 30 s and 10 cycles of PCR (95° C. for 30 s denaturation, 60° C. for 30 s annealing, and 72° C. for 30 s extension), with a final extension at 72° C. for 5 min. The final cDNA library was eluted in 20 μL EB buffer after a wash step using 0.9×AMPure beads.

Metagenomic Sequencing

The cDNA libraries were quantified using the Qubit fluorometer (Thermo Fisher Scientific) and the sizes of the libraries were measured using Agilent Bioanalyzer (Agilent Technologies, Santa Clara, CA). Illumina sequencing was performed on a MiSeq instrument using 150 nt single-end runs according to the manufacturer's protocol. For nanopore, amplified cDNA libraries from Nextera library preparation were end-repaired and ligated with adapter and motor proteins using the 1D Ligation Sequencing Kit (Oxford Nanopore Technologies). Metagenomic libraries for nanopore sequencing were run on R9.4 or R9.5 flow cells, using either a MinION MK1B or GridION X5 instrument (Oxford Nanopore Technologies).

Capture Probe Enrichment for ZIKV Samples

The xGen Lockdown Kit (IDT Technologies, Redwood City, CA) was used for capture probe enrichment of ZIKV. Briefly, barcoded amplified cDNA libraries corresponding to each sample were mixed in equimolar proportions to generate a 500 ng pooled library. The pooled library was then added to a hybridization mix containing ZIKV xGen Lockdown probes, and the hybridization reaction was performed by incubation at 65° C. for 16 h, followed by streptavidin bead capture for 45 min. Beads containing captured cDNA were re-suspended in an amplification reaction mix (25 μL KAPA HiFi HotStart ReadyMix, 1.25 μL xGen primer and 3.75 μL water), and post-capture PCR was performed (98° C. for 45 s, followed by 10 cycles of denaturing (98° C. for 15 s), annealing (60° C. for 30 s), and extension (72° C. for 30 s), with a final extension at 72° C. for 1 min). PCR amplicons were purified using 1.5× volume of AMPure XP beads and finally eluted in 20 μL EB buffer. Purified PCR products were analyzed by 2% gel electrophoresis to check library size, and DNA concentration was estimated using the Qubit fluorometer. The capture probe enriched library was run on an Illumina MiSeq instrument using 150 nt single-end runs according to the manufacturer's protocol.

Tiling Multiplex PCR Enrichment for ZIKV

Tiling multiplex PCR for ZIKV enrichment was performed according to the "Primal" protocol described by Quick et. al (2017) Nat Protoc 12:1261, except for libraries prepared using both MSSPE and tiling multiplex PCR, for which an AMPure bead wash of 1.2× was performed immediately after cDNA synthesis (before adding multiplexed primers) to remove residual ZIKV MSSPE primers (4 M) that had been added during the reverse transcription step. After visualization of a PCR band of the expected size (400 nt) by 2% gel electrophoresis, barcoded sequencing libraries were prepared using the NEBNext Ultra II DNA Library Preparation Kit (New England BioLabs, Inc., Ipswich, MA), and sequenced on an Illumina MiSeq instrument using 250 nt paired-end runs according to the manufacturer's protocol.

Bioinformatics Pipelines for Viral Detection and Reference Genome Alignment

Sequencing data from Illumina MiSeq or HiSeq instruments were analyzed for viruses using the SURPI+ ("sequence based ultra-rapid pathogen identification") computational pipeline (UCSF), a modified version of a previously published bioinformatics analysis pipeline for pathogen identification from mNGS sequence data (Naccache et al. (2014) Genome Res 24:1180). Specifically, the SURPI+ pipeline modifications include (i) updated reference databases based on the NCBI nt database (March 2015 build), (ii) a filtering algorithm for exclusion of false-positive hits from database misannotations, and (iii) taxonomic classification for species-level identification. Viral reads were mapped to reference genome and percent coverage determined an in-house developed SURPIviz graphical visualization interface or Geneious software v10 (Kearse et al. (2012) Bioinformatics 28:1647). For virus detection from nanopore reads, an in-house developed pipeline called SURPIrt (SURPI "real-time", unpublished), which identifies viral reads by Bowtie2 alignment (Langmead, 2012 #47) to the NCBI Viral RefSeq database or the viral portion of the NCBI nt database, was used. Viral reads obtained by nanopore sequencing were mapped to reference genomes using GraphMap (Sovic et al. (2016) Nat Commun 7:11307).

Quantification and Statistical Analysis

The RPM (reads per million) metric was calculated as the number of viral species-specific reads divided by the number of preprocessed reads (reads remaining after adapter trimming, low-quality filtering, and low-complexity filtering of raw reads) for Illumina sequencing, or the number of viral species-specific reads divided by the number of base called reads for nanopore sequencing. The fold change for MSSPE enrichment was defined as the RPM obtained for a target virus using MSSPE divided by the RPM obtained using RH priming only. The median fold change is given instead of the mean fold change if the data contained outliers. The percent increase in genome coverage is the genome coverage obtained using RH alone subtracted from that obtained using MSSPE. Chi-squared test was used to compare two proportions, and p value less than 0.05 is considered statistically significant.

Results

A general method was developed for viral enrichment and genome recovery from clinical samples for use in diagnostics, public health surveillance, and outbreak investigation. The method is (i) applicable for any targeted virus, regardless of its degree of representation in reference databases (e.g. from 60 to 3,571 reference genomes/genome segments) (FIG. 10A), (ii) preserves broad metagenomic sensitivity for comprehensive detection of known and novel pathogens (viral and non-viral) and co-infections, (iii) does not affect overall turnaround times for sample processing, and (iv) enriches mNGS libraries sufficiently to allow robust viral genome recovery from low-titer clinical samples. An automated computational algorithm was designed that took as input an arbitrary set of reference genomes and constructed a minimal panel of short, 13-nt spiked primers covering these genomes (FIG. 10A), to be added during the cDNA synthesis (reverse transcription step of mNGS library preparation (FIG. 10B). Spiked primers were designed for 14 viruses, in total comprising 6,102 primers and including vector-borne and/or hemorrhagic fever viruses of public health significance.

Figure 10A:
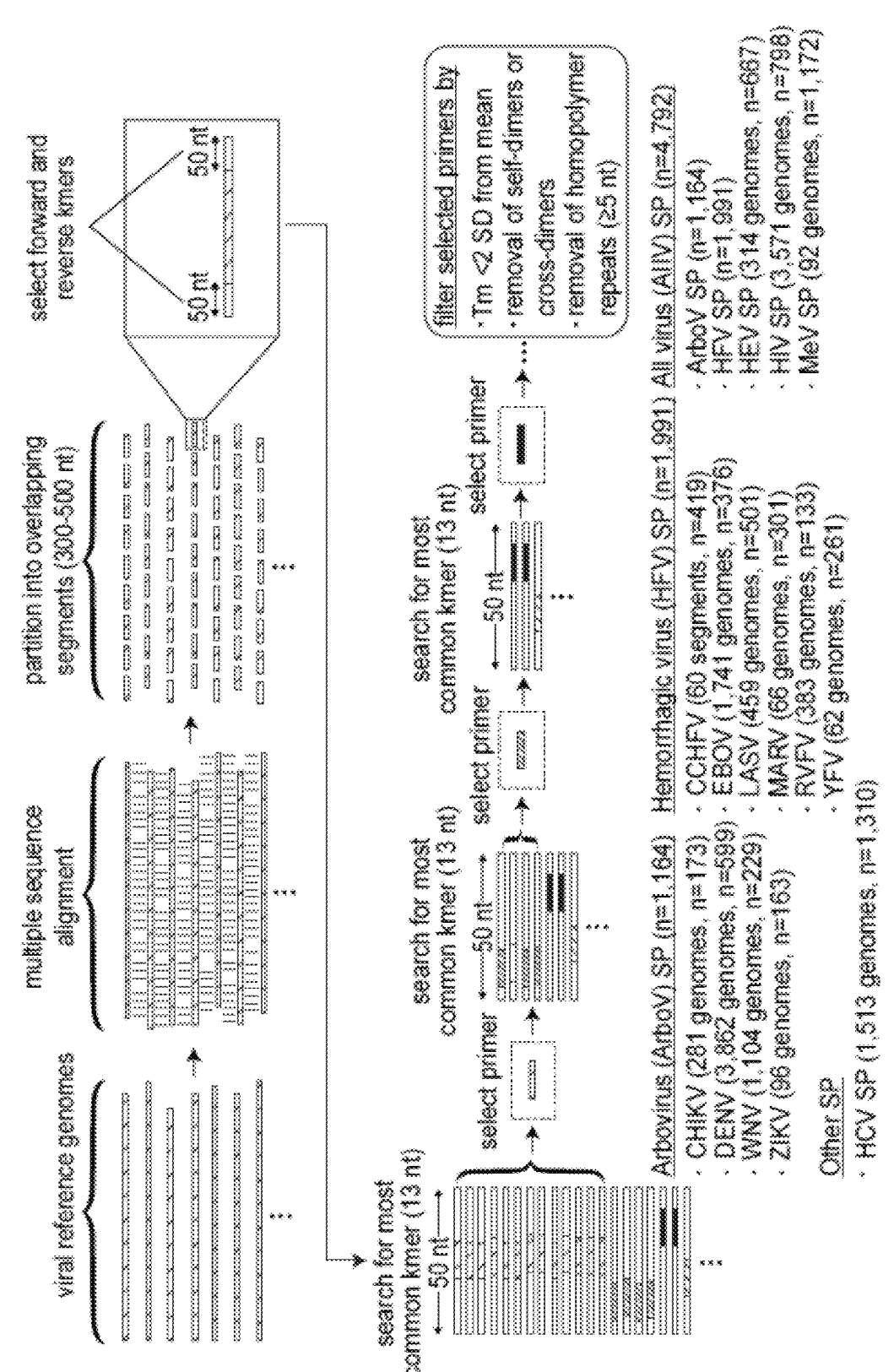
Figure 10B:
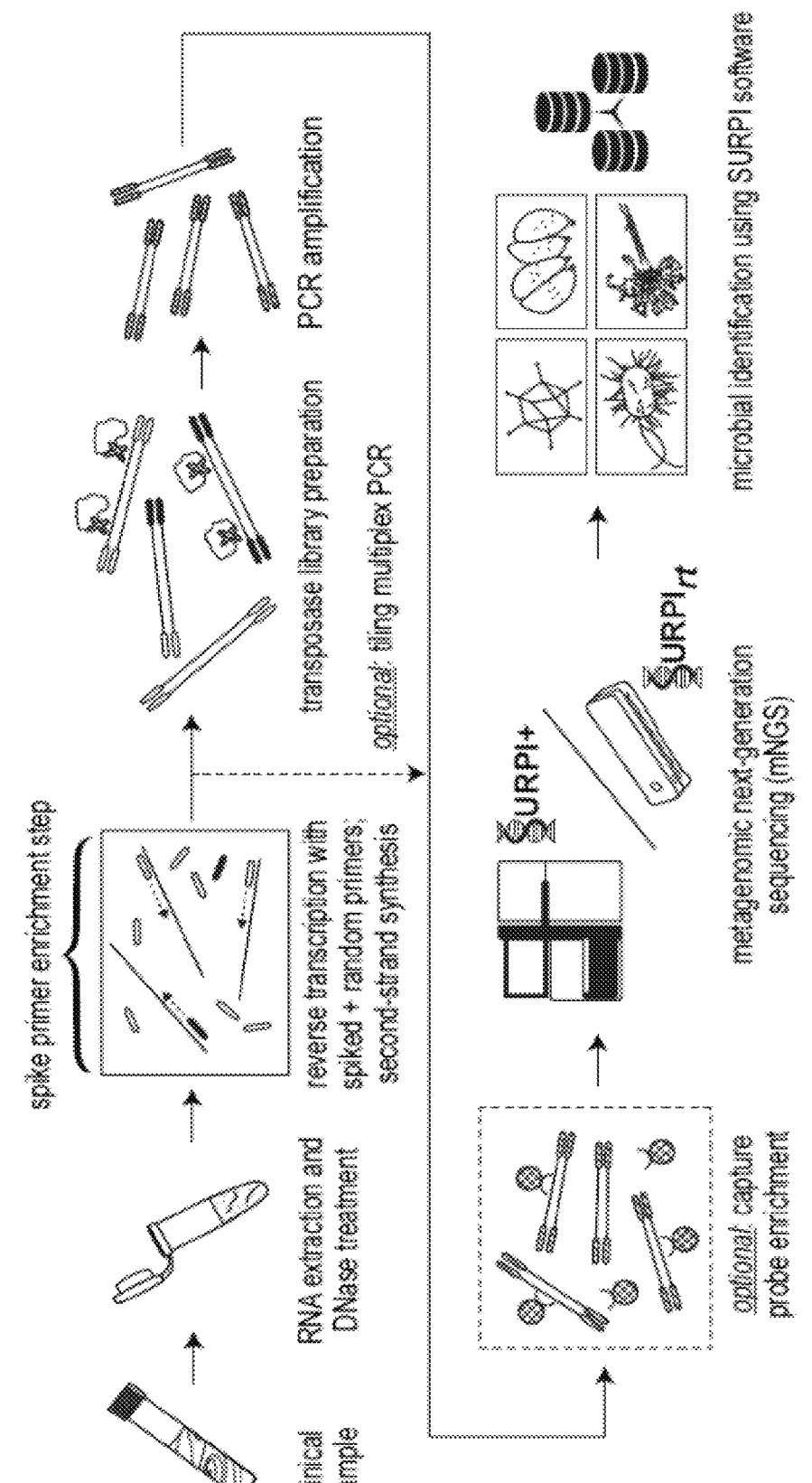

FIG. 10A depicts an algorithm for design of viral spiked primers. A set of viral reference genomes (60 to 3,571) were aligned using MAFFT multiple sequence alignment software (Katoh et al. (2014) supra), followed by partitioning of each genome into 300-500 nucleotide (nt) overlapping segments. Forward and reverse 13 nt primers ("kmers") were selected and filtered according to specific criteria (rounded rectangular box). Using this algorithm, primers were designed for 14 RNA viruses. Spiked primer panels for arboviruses (ArboV SP; n=4), hemorrhagic fever viruses (HFV SP; n=6), and all virus (AllV SP; n=13, excluding HCV) were also constructed. FIG. 10B depicts a metagenomic sequencing workflow. MSSPE primers are added ("spiked") to the reaction mix during the reverse transcription step of cDNA synthesis, without adding to the overall turnaround time for the library preparation and sequencing analysis protocols. The MSSPE workflow is compatible with subsequent enrichment using tiling multiplex PCR and/or capture probes (dotted lines). Metagenomic sequence data is analyzed for pathogen identification using SURPI software (Naccache et al. (2014) supra).

The performance of the spiked primer panels was evaluated on the MinION portable nanopore sequencing platform (Oxford Nanopore Technologies, Oxford, UK). The results are shown in the table provided in FIG. 11. As shown in FIG. 11, overall levels of ZIKV, EBOV, and DENV enrichment at viral titers ranging from 10-1,000 copies/mL were comparable for the two platforms (median enrichment of 7.8× on the MinION and 9.2× on the Illumina MiSeq). The use of spiked primer panels enabled detection of ZIKV and EBOV down to 10 copies/mL, near the limits of detection for virus-specific PCR (Cherpillod et al. (2016) *J Clin Virol* 77:9; Corman et al. (2016) *Bull World Health Organ* 94:880), whereas no ZIKV or EBOV reads were obtained by mNGS using RH primers alone.

It was hypothesized that the increased proportion of viral reads obtained using the MSSPE method would improve genome coverage. Using ZIKV spiked primers on plasma samples spiked with 1,000 copies/mL of ZIKV more than doubled the genome coverage obtained using RH primers only, from 35.8% to 72.8%. The performance of virus-specific primers for genome sequencing of ZIKV, DENV, EBOV, HIV-1 (divergent and recombinant strains from Cameroon and DRC, Africa), and HCV (genotypes 2, 4, and 6 from California, United States) was evaluated. The data are presented in the table provided in FIG. 12. As shown in the table presented in FIG. 12, on average, a 49% (±13.9% SD) increase in genome coverage was achieved using spiked primer relative to RH primers only for contrived ZIKV, DENV, HIV and EBOV samples at titers of 100-1,000 copies/mL, and a 42% (±15.0% SD) increase in genome coverage for clinical HIV-1 and HCV samples at titers ranging from 100-10,000 copies/mL. Similarly, a 36.5% (±16.8% SD) increase in genome coverage was obtained using spiked primer panels (ArboV, HFV, and AllV) for contrived and clinical samples of ZIKV, DENV, and EBOV. No significant gains in genome coverage were observed at a titer of 10 copies/mL, a finding attributed to insufficient sequencing depth. In addition, we tested the MSSPE method using EBOV and DENV spiked for genome recovery on the MinION nanopore sequencer. With contrived samples at a titer of 1,000 copies/mL, comparable percentage increases in genome coverage were achieved on both ONT MinION nanopore and Illumina MiSeq sequencing platforms.

To assess the utility of MSSPE for pathogen discovery, it was tested whether spiked primers could enrich for sequences from emerging flaviviruses in clinical samples from infected patients. Of note, flaviviruses had not been specifically targeted in the initial spiked primer design. ZIKV spiked primers were used to enrich for St. Louis encephalitis (SLEV), whereas ArboV panel spiked primers were used to enrich for Powassan virus (POWV) in patient cerebrospinal fluid (CSF) samples. As shown in the table presented in FIG. 13, use of ZIKV spiked primers enriched the number of reads to SLEV by ~3×, with a corresponding increase in 17.5% genome coverage. In CSF from a patient with tick-borne POWV meningoencephalitis, the use of ArboV spiked primers enriched for POWV reads by 15× over RH primers alone, and improved viral genome coverage by 43%. FIG. 13.

An HIV clinical sample was initially found to harbor Usutu virus (USUV), a flavivirus, by MSSPE using HIV-1 spiked primers. Interestingly, the degree of enrichment for USUV using these HIV-1 spiked primers over RH primers alone was 6×; subsequent analysis of the HIV-1 spiked primers found that 18 of them aligned incidentally to the USUV genome with 0 or 1 mismatches (92.3% or 100% identity). Running the same sample on the Illumina MiSeq at a limited throughput of ~1 million raw reads resulted in detection of no USUV reads with RH primers alone, but 6 reads with the use of ArboV primers. Deeper sequencing on the Illumina HiSeq of ~123 million reads revealed that the degree of enrichment of USUV reads using the ArboV panel was 7× (FIG. 13), with a corresponding increase in genome coverage of 25.6%.

Head-to-head comparisons were performed of MSSPE with both capture probe (Naccache et al. (2016) *Emerg Infect Dis* 22:1788) and tiling multiplex PCR (Quick et al. (2017) *Nat Protoc* 12:1261) methods for enrichment of viral reads from ZIKV-positive clinical samples at low titers (310-28,200 copies/mL). The degree of improvement in genome coverage using MSSPE was comparable to capture probe and tiling multiplex PCR methods. However, a small amount of cross-contamination was observed using capture probe and multiplex PCR, versus no cross-contamination using MSSPE. Tiling multiplex PCR for ZIKV was negative when testing a contrived ZIKV sample containing the 1947 prototype Uganda strain, likely due to sequence divergence from the Asian lineage reference genomes from the 2014-2016 ZIKV outbreak in the Americas that were used in the initial multiplex PCR primer design (Quick et al. (2017) supra).

The performance of MSSPE followed by subsequent tiling multiplex PCR or capture probe enrichment on low-titer contrived and clinical ZIKV samples (666-3,340 copies/mL) was evaluated. The use of spiked primers further increased the number of ZIKV reads by 3×-5× and corresponding genome coverage by 25%-80% (average 58.5±21.5%), as compared to RH primers alone. MSSPE was critical for ZIKV genome recovery in the two samples tested by tiling multiplex PCR, as multiplex PCR with the standard RH priming failed to yield a distinct band on gel electrophoresis, likely due to low abundance of virus in the samples.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

SEQUENCE LISTING

The patent contains a lengthy sequence listing. A copy of the sequence listing is available in electronic form from the USPTO web site (https://seqdata.uspto.gov/docdetail?docId=US12644145B2). An electronic copy of the sequence listing will also be available from the USPTO upon request and payment of the fee set forth in 37 CFR 1.19(b)(3).

---

What is claimed is:

1. A method for characterizing a target DNA present in a sample, the method comprising:

A1) amplifying nucleic acids in the sample using recombinase polymerase amplification;

A2) contacting the sample with:

(a) a type V CRISPR/Cas effector protein; and (b) one or more guide RNAs, wherein the one or more guide RNAs comprise:

i) a region that binds to the type V CRISPR/Cas effector protein; and ii) a guide sequence that hybridizes with the target DNA, wherein said contacting generates a protospacer adjacent motif (PAM)-distal cleavage product comprising a 5' overhang;

B) ligating a double-stranded nucleic acid adapter to the cleavage product, wherein the adapter comprises a 3' deoxyadenosine overhang and a 5' overhang that comprises a stretch of from 3 to 15 contiguous nucleotides that are complementary to a contiguous stretch of nucleotides of the same length in the 5' overhang of the PAM-distal cleavage product, wherein said ligating generates a ligation product comprising the adapter and the PAM-distal cleavage product; and C) determining the nucleotide sequence of the PAM-distal cleavage product present in the ligation product.

2. The method of claim 1, wherein the type V CRISPR/Cas effector protein is a Cas protein selected from the group consisting of a Cas12 protein, a Cas12a (Cpf1) protein, a Cas12b (C2c1) protein, a Cas12d protein, and a Cas14a protein.

3. The method of claim 1, wherein the target DNA is single stranded.

4. The method of claim 1, wherein the target DNA is double stranded.

5. The method of claim 1, wherein the target DNA is viral DNA.

6. The method of claim 5, wherein the target DNA is papovavirus, hepadnavirus, herpesvirus, adenovirus, poxvirus, or parvovirus DNA.

7. The method of claim 1, wherein the target DNA is bacterial DNA.

8. The method of claim 1, wherein the target DNA is from tick-borne pathogen DNA.

9. The method of claim 1, wherein the target DNA is from multiple drug resistant bacterial DNA.

10. The method of claim 1, wherein the target DNA is DNA of a eukaryotic pathogen.

11. The method of claim 10, wherein the eukaryotic pathogen is a pathogenic protozoan, a pathogenic fungus, or a pathogenic helminth.

12. The method of claim 10, wherein the pathogenic protozoan is a *Plasmodium* spp., a *Trypanosoma* spp., a *Trichomonas* spp., an amoeba, a *Giardia* spp., or a *Toxoplama* spp.

13. The method of claim 11, wherein the pathogenic fungus is an *Aspergillus* spp., a *Candida* spp., an *Epidermophyton* spp., a *Histoplasma* spp., or a *Trichphtyon* spp.

14. The method of claim 11, wherein the pathogenic helminth is a nematode or a platyhelminth.

15. The method of claim 11, wherein the pathogenic helminth is selected from the group consisting of an *Ascaris* spp., an *Echinococcus* spp., a *Schistosoma* spp., a *Strongyloides* spp., a *Taenia* spp., and a *Trichinella* spp.

16. The method of claim 1, wherein the target DNA is fetal DNA.

17. The method of claim 1, comprising contacting the sample with 2 or more guide RNAs, wherein the 2 or more guide RNAs differ from one another in the guide sequence.

18. The method of claim 1, wherein the sample comprises a cell.

19. The method of claim 1, wherein the sample is a cell lysate.

20. The method of claim 1, wherein the sample is a cell-free sample.

21. The method of claim 1, wherein the sample is blood, serum, plasma, bronchoalveolar lavage, sputum, urine, cerebrospinal fluid, feces, or a biopsy sample.

22. The method of claim 1, wherein said amplifying comprises contacting the sample with 2 or more sets of primer pairs.

23. The method of claim 1, wherein said amplifying comprises contacting the sample with 1 or more pairs of forward and reverse primers, wherein the 1 or more pairs of forward and reverse primers have sequences selected from the group consisting of SEQ ID Nos: 71 to 6432.

24. The method of claim 1, wherein said amplifying comprises contacting the sample with 1 or more pairs of forward and reverse primers, wherein the 1 or more pairs of forward and reverse primers have sequences selected from the group consisting of SEQ ID Nos: 6433 to 13607.

25. The method of claim 1, wherein said amplifying comprises contacting the sample with 1 or more pairs of forward and reverse primers, wherein the 1 or more pairs of forward and reverse primers have sequences selected from the group consisting of SEQ ID Nos:13608 to 17378.

26. The method of claim 1, wherein sequence determination is carried out by nanopore sequencing.

27. The method of claim 1, wherein the target DNA is present in the sample at a concentration as low as 200 fM.

28. The method of claim 1, further comprising contacting the sample with a detector DNA that is single stranded and does not hybridize with the guide sequence of the guide RNA; and measuring a detectable signal produced by cleavage of the single stranded detector DNA by the type V CRISPR/Cas effector protein, thereby detecting the target DNA.

29. The method of claim 28, wherein the single stranded detector DNA comprises a fluorescence-emitting dye pair.

30. The method of claim 29, wherein the fluorescence-emitting dye pair is a fluorescence resonance energy transfer (FRET) pair.

31. The method of claim 30, wherein the fluorescence-emitting dye pair is a quencher/fluor pair.

32. The method of claim 28, wherein the single stranded detector DNA comprises a modified nucleobase, a modified sugar moiety, and/or a modified nucleic acid linkage.

\* \* \* \* \*